(12) United States Patent
Wang et al.

(10) Patent No.: US 12,084,492 B2
(45) Date of Patent: Sep. 10, 2024

(54) ANTI-AMYLOID BETA PROTOFIBRIL/OLIGOMER ANTIBODIES AND USES THEREOF

(71) Applicant: MABWELL THERAPEUTICS, INC., San Diego, CA (US)

(72) Inventors: Yubin Wang, San Diego, CA (US); Lei Huang, San Diego, CA (US); Xin Du, La Jolla, CA (US)

(*) Notice: Subject to any disclaimer, the term of this patent is extended or adjusted under 35 U.S.C. 154(b) by 0 days.

(21) Appl. No.: 18/417,299

(22) Filed: Jan. 19, 2024

(65) Prior Publication Data
US 2024/0247054 A1 Jul. 25, 2024

Related U.S. Application Data

(60) Provisional application No. 63/440,345, filed on Jan. 20, 2023.

(51) Int. Cl.
| | |
|---|---|
| *G01N 31/00* | (2006.01) |
| *A61P 25/28* | (2006.01) |
| *C07K 16/18* | (2006.01) |
| *G01N 33/53* | (2006.01) |
| *G01N 33/68* | (2006.01) |
| *A61K 39/00* | (2006.01) |

(52) U.S. Cl.
CPC .............. *C07K 16/18* (2013.01); *A61P 25/28* (2018.01); *G01N 33/6857* (2013.01); *A61K 2039/505* (2013.01); *C07K 2317/21* (2013.01); *C07K 2317/24* (2013.01); *C07K 2317/565* (2013.01); *C07K 2317/70* (2013.01)

(58) Field of Classification Search
None
See application file for complete search history.

(56) References Cited

U.S. PATENT DOCUMENTS

| | | | |
|---|---|---|---|
| 8,025,878 | B2 | 9/2011 | Gellerfors et al. |
| 9,573,994 | B2 | 2/2017 | Nerelius et al. |
| 2017/0355756 | A1* | 12/2017 | Julien ............... C07K 16/18 |

FOREIGN PATENT DOCUMENTS

| | | | | |
|---|---|---|---|---|
| EP | 2210901 | A1 | 7/2010 | |
| WO | WO-2008068048 | A2 * | 6/2008 | ............ A61P 31/10 |
| WO | 2009051220 | A1 | 4/2009 | |
| WO | 2009065054 | A2 | 5/2009 | |
| WO | 2011151076 | A2 | 12/2011 | |
| WO | 2017157961 | A1 | 9/2017 | |
| WO | 2022020680 | A1 | 1/2022 | |

OTHER PUBLICATIONS

Mariuzza (Annu. Rev. Biophys. Biophys. Chem., 16: 139-159, 1987) (Year: 1987).*
Wang et al (Alzheimer's & Dementia, Drug Development, First published: Dec. 25, 2023 (https://doi.org/10.1002/alz.075643) (Year: 2023).*
Perneczky R, Jessen F, Grimmer T, et al. Anti-amyloid antibody therapies in Alzheimer's disease. Brain. 2023; 146(3):842-849. doi:10.1093/brain/awad005.
Van Dyck CH, Swanson CJ, Aisen P, et al. Lecanemab in Early Alzheimer's Disease. N Engl J Med. 2023;388(1):9-21. doi:10.1056/NEJMoa2212948.
Söderberg L, Johannesson M, Nygren P, et al. Lecanemab, Aducanumab, and Gantenerumab—Binding Profiles to Different Forms of Amyloid-Beta Might Explain Efficacy and Side Effects in Clinical Trials for Alzheimer's Disease. Neurotherapeutics. 2023;20(1):195-206. doi:10.1007/s13311-022-01308-6.
Tucker S, Möller C, Tegerstedt K, et al. The murine version of BAN2401 (mAb158) selectively reduces amyloid-β protofibrils in brain and cerebrospinal fluid of tg-ArcSwe mice. J Alzheimers Dis. 2015;43(2):575-588. doi:10.3233/JAD-140741.
Sevigny J, Chiao P, Bussière T, et al. The antibody aducanumab reduces Aβ plaques in Alzheimer's disease. Nature. 2016;537(7618):50-56. doi:10.1038/nature19323.
Demattos RB, Lu J, Tang Y, et al. A plaque-specific antibody clears existing β-amyloid plaques in Alzheimer's disease mice. Neuron. 2012;76(5):908-920. doi:10.1016/j.neuron.2012.10.029.
Bohrmann B, Baumann K, Benz J, et al. Gantenerumab: a novel human anti-Aβ antibody demonstrates sustained cerebral amyloid-β binding and elicits cell-mediated removal of human amyloid-β. J Alzheimers Dis. 2012;28(1):49-69. doi:10.3233/JAD-2011-110977.
Pradier, Laurent et al, "SAR228810: an antibody for protofibrillar amyloid [beta] peptide designed to reduce the risk of amyloid-related imaging abnormalities (ARIA)", Alzheimer's Research & Therapy, vol. 10, Article No. 117, Nov. 28, 2018 (Nov. 28, 2018), DOI: 10.1186/s13195-018-0447-7.
International Search Report PCT/US2024/012126 mailed May 22, 2024.

* cited by examiner

*Primary Examiner* — Lisa V Cook
(74) *Attorney, Agent, or Firm* — PERDUE IP LAW, APC; Donna O. Perdue

(57) ABSTRACT

The present disclosure provides anti-amyloid β (Aβ) antibodies and antibody fragments that preferentially bind soluble amyloid Aβ protofibril/oligomer and trigger ADPC in microglial cells, anti-amyloid β (Aβ) antibodies and antibody fragments that reduce soluble amyloid Aβ protofibril/oligomer levels and insoluble amyloid Aβ plaque in brain tissue, and the use of anti-Aβ protofibril/oligomer antibodies and antibody fragments in therapy, prophylaxis, diagnosis, screening, and monitoring of conditions associated with Aβ protein aggregation, in particular Alzheimer's disease (AD).

12 Claims, 17 Drawing Sheets
Specification includes a Sequence Listing.

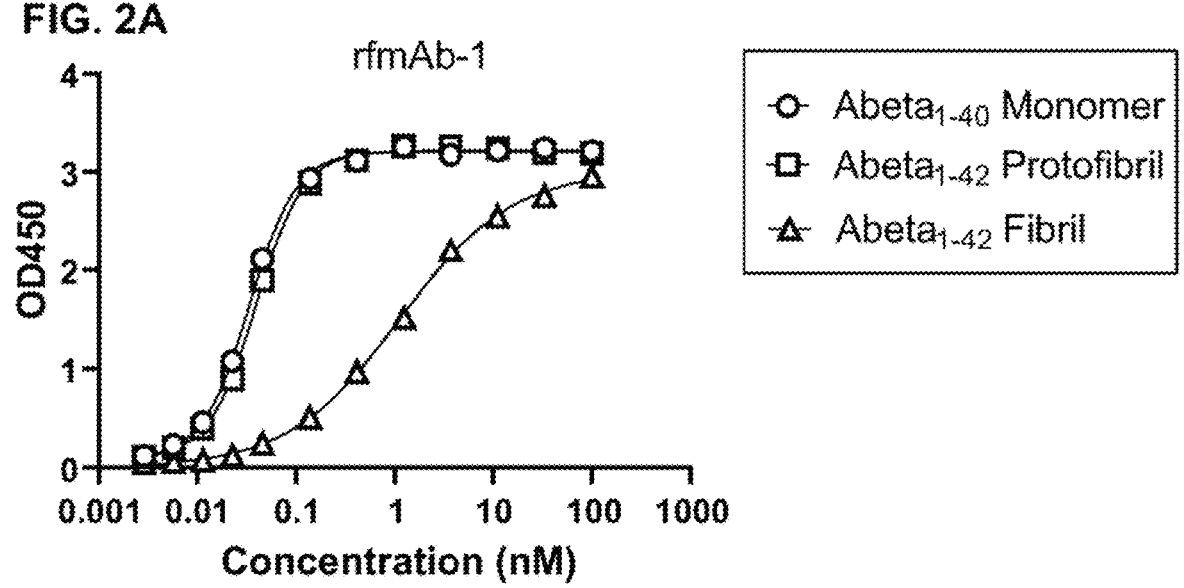
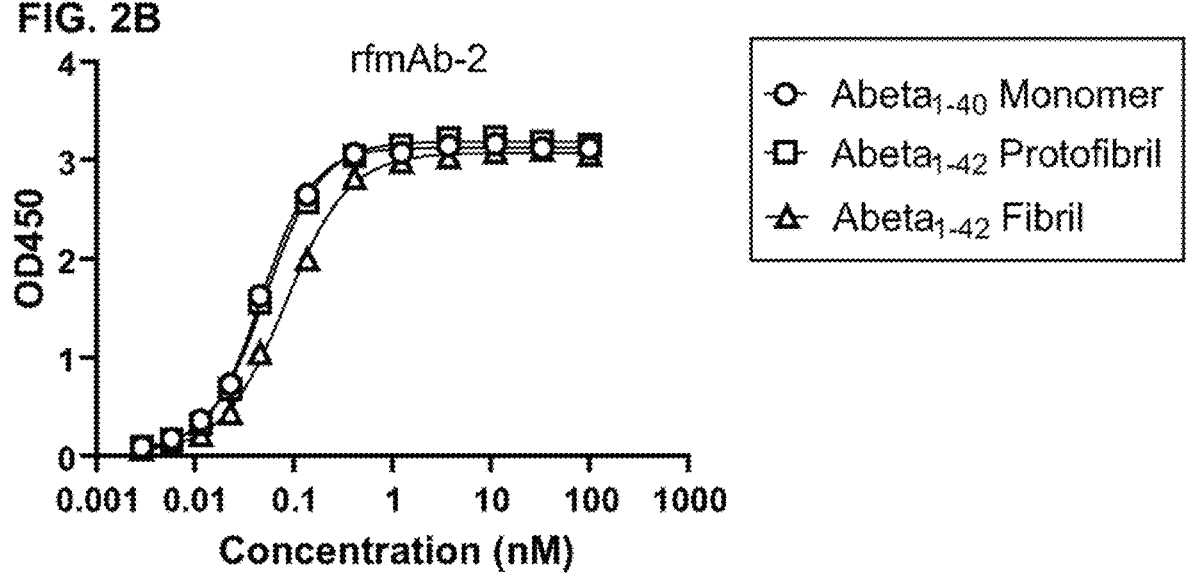

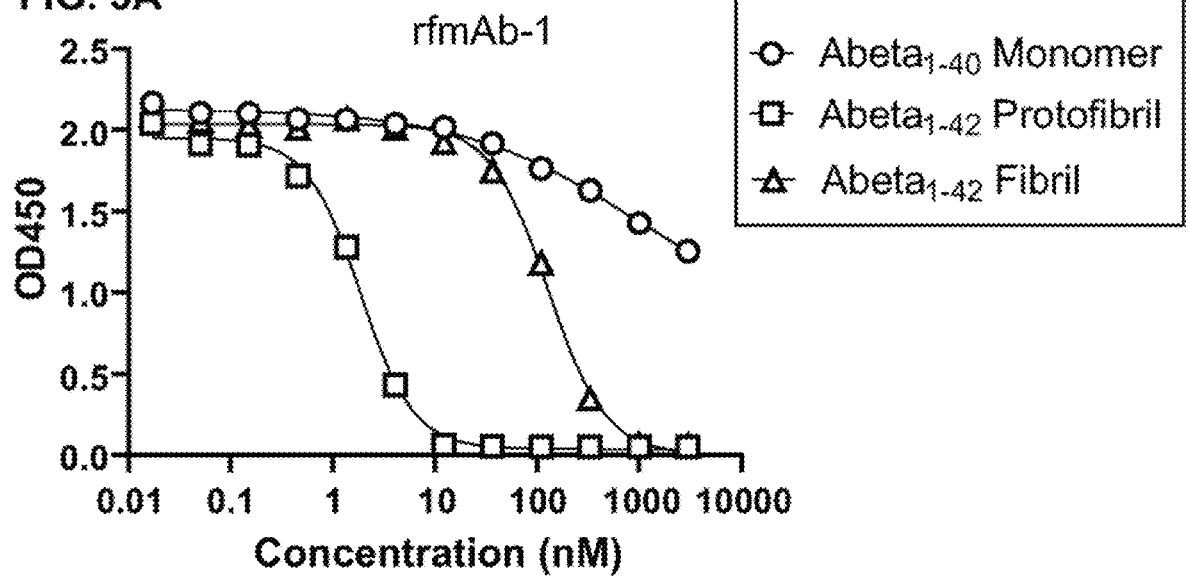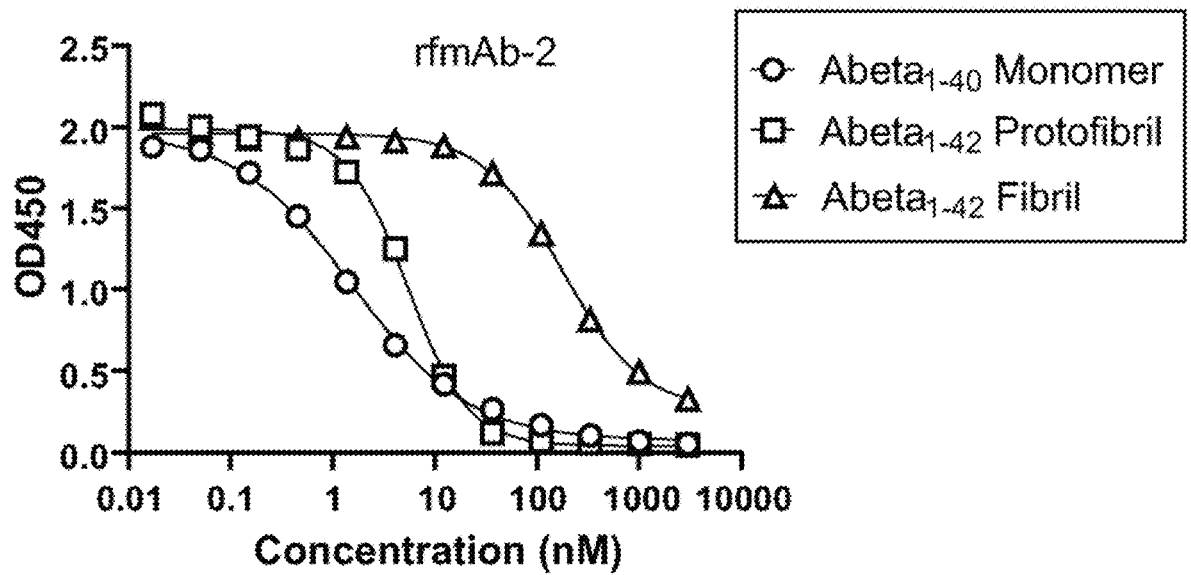

| Parameter | rfmAb-1 | 17P04 | 18P01 |
|---|---|---|---|
| T½ (hr) | 140.9 | 199.7 | 183.2 |
| AUC_0-t (uM*hr) | 47.2 | 120.8 | 38.6 |
| AUC_0-inf (uM*hr) | 59.3 | 157 | 54.7 |
| %Extrap | 20.3 | 23 | 29.4 |
| Cmax (uM) | 0.8 | 0.9 | 0.6 |
| Tmax (hr) | 8 | 48 | 4 |

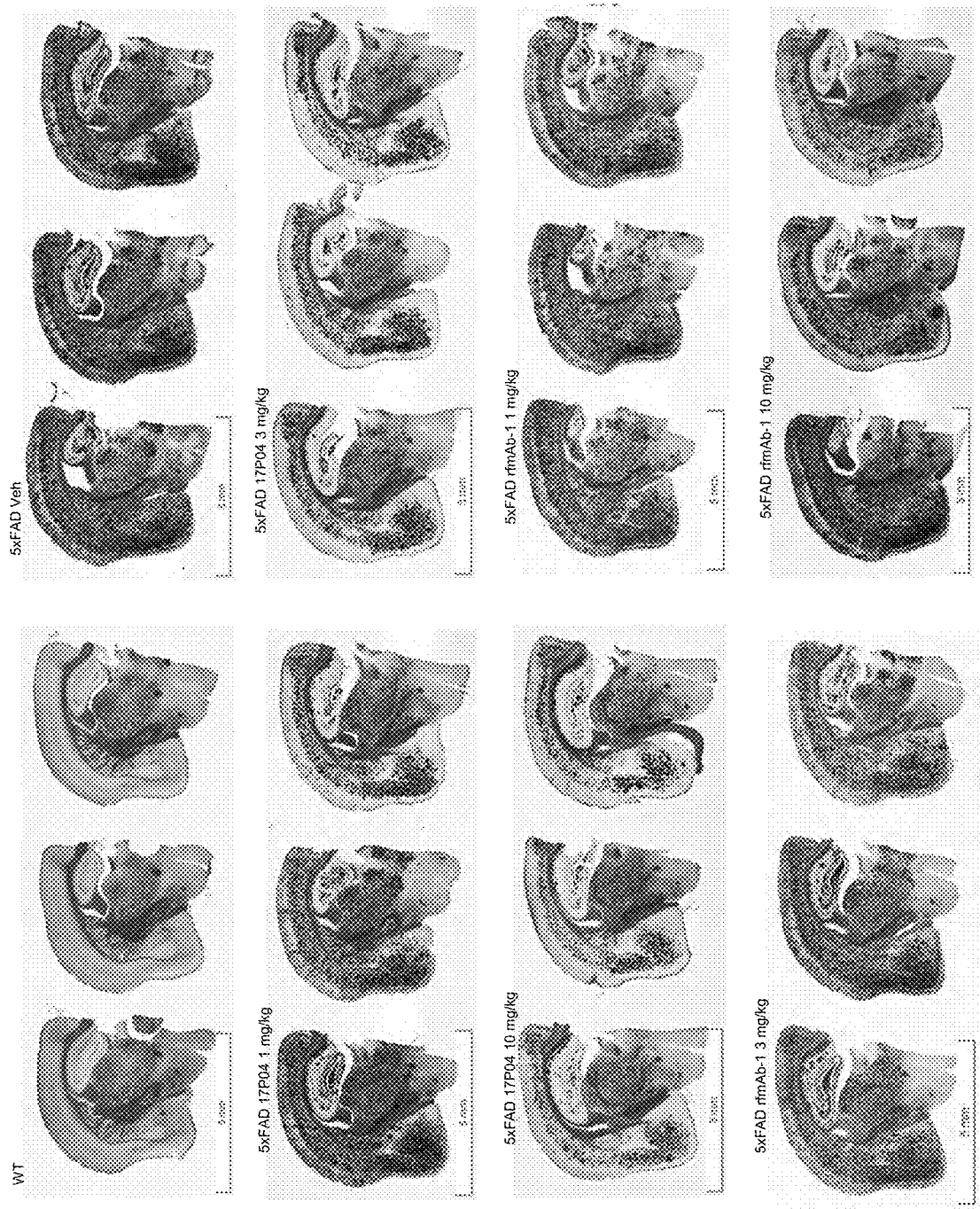

SEQUENCE LISTING

```
Sequence total quantity: 170
SEQ ID NO: 1          moltype = AA  length = 117
FEATURE               Location/Qualifiers
source                1..117
                      mol_type = protein
                      organism = Mus musculus
```

```
                            note = Monoclonal antibody 06E17A VH heavy chain variable
                                region
SEQUENCE: 1
EVQLVESGGG LVKPGGSLRL SCAASGFSFS NAWMSWVRQA PGKGLEWVGR IKSKTDGGTI      60
DYAAPVKGRF TISRDDSKNT LYLQMNSLKT EDTAVYYCTT GYGEGYWGQG TLVTVSS        117

SEQ ID NO: 2            moltype = AA  length = 8
FEATURE                 Location/Qualifiers
source                  1..8
                        mol_type = protein
                        organism = Mus musculus
                        note = 06E17A HC CDR1
SEQUENCE: 2
GFSFSNAW                                                                8

SEQ ID NO: 3            moltype = AA  length = 10
FEATURE                 Location/Qualifiers
source                  1..10
                        mol_type = protein
                        organism = Mus musculus
                        note = 06E17A HC CDR2
SEQUENCE: 3
IKSKTDGGTI                                                             10

SEQ ID NO: 4            moltype = AA  length = 8
FEATURE                 Location/Qualifiers
source                  1..8
                        mol_type = protein
                        organism = Mus musculus
                        note = 06E17A HC CDR3
SEQUENCE: 4
TTGYGEGY                                                                8

SEQ ID NO: 5            moltype = DNA  length = 351
FEATURE                 Location/Qualifiers
source                  1..351
                        mol_type = genomic DNA
                        organism = Mus musculus
                        note = Antibody 06E17A VH heavy chain variable region
SEQUENCE: 5
gaggtgcagc tggtggagtc tgggggaggc ttggtaaagc ctgggggctc ccttagactc      60
tcctgtgcag cctctggatt tagtttcagt aacgcctgga tgagctgggt ccgccaggct     120
ccagggaagg ggctggagtg ggttggccgt attaaaagca aaactgatgg tggacaata      180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
ggctacggtg aaggctactg gggccaggga accctggtca ccgtctcctc a             351

SEQ ID NO: 6            moltype = AA  length = 110
FEATURE                 Location/Qualifiers
source                  1..110
                        mol_type = protein
                        organism = Mus musculus
                        note = Monoclonal antibody 06E17A VL light chain variable
                            region
SEQUENCE: 6
QSVLTQPPSA SGTPGQRVTI SCSGSSSNIK SNTVNWYQQL PGTAPKLLIY RNNQRPSGVP      60
DRFSGSKSGT SASLAISGLQ SEDEADYYCA AWDDSLKGVV FGGGTDLTVL                110

SEQ ID NO: 7            moltype = AA  length = 8
FEATURE                 Location/Qualifiers
source                  1..8
                        mol_type = protein
                        organism = Mus musculus
                        note = 06E17A LC CDR1
SEQUENCE: 7
SSNIKSNT                                                                8

SEQ ID NO: 8            moltype =    length =
SEQUENCE: 8
000

SEQ ID NO: 9            moltype = AA  length = 11
FEATURE                 Location/Qualifiers
source                  1..11
                        mol_type = protein
                        organism = Mus musculus
                        note = 06E17A LC CDR3
SEQUENCE: 9
AAWDDSLKGV V                                                           11
```

```
SEQ ID NO: 10            moltype = DNA   length = 330
FEATURE                  Location/Qualifiers
source                   1..330
                         mol_type = genomic DNA
                         organism = Mus musculus
                         note = Antibody 06E17A VL light chain variable region
SEQUENCE: 10
cagtctgtgc tgactcagcc accctcagcg tctgggaccc ccgggcagag ggtcaccatc   60
tcttgttctg gaagcagctc caacatcaaa agtaatactg tcaactggta ccagcagctc  120
ccaggaacgg cccccaaact cctcatctat aggaataatc agcggccctc aggggtccct  180
gaccgattct ctggctccaa gtctggcacc tcagcctccc tggccatcag tgggctccag  240
tctgaggatg aggctgatta ttactgtgca gcatgggatg acagcctgaa gggtgtggta  300
ttcggcggag ggaccgatct gaccgtccta                                    330

SEQ ID NO: 11            moltype = AA   length = 121
FEATURE                  Location/Qualifiers
source                   1..121
                         mol_type = protein
                         organism = Mus musculus
                         note = Monoclonal antibody 15M13A VH heavy chain variable
                          region
SEQUENCE: 11
QVTLKESGPG ILQPSQTLSL TCSFSGFSLS TFGMGVGWIR QPSGKGLEWL AHIWWDDDKY   60
YNPALKSRLT ISKDTSKNQV FLKIANVDTA DTATYYCARL GYYPYWFFDV WGTGTTVTVS  120
S                                                                  121

SEQ ID NO: 12            moltype = AA   length = 10
FEATURE                  Location/Qualifiers
source                   1..10
                         mol_type = protein
                         organism = Mus musculus
                         note = 15M13A HC CDR1
SEQUENCE: 12
GFSLSTFGMG                                                          10

SEQ ID NO: 13            moltype = AA   length = 7
FEATURE                  Location/Qualifiers
source                   1..7
                         mol_type = protein
                         organism = Mus musculus
                         note = 15M13A HC CDR2
SEQUENCE: 13
IWWDDDK                                                              7

SEQ ID NO: 14            moltype = AA   length = 13
FEATURE                  Location/Qualifiers
source                   1..13
                         mol_type = protein
                         organism = Mus musculus
                         note = 15M13A HC CDR3
SEQUENCE: 14
ARLGYYPYWF FDV                                                      13

SEQ ID NO: 15            moltype = DNA   length = 363
FEATURE                  Location/Qualifiers
source                   1..363
                         mol_type = genomic DNA
                         organism = Mus musculus
                         note = Antibody 15M13A VH heavy chain variable region
SEQUENCE: 15
caggttactc tgaaagagtc tggccctggg atattgcagc cctcccagac cctcagtctg   60
acttgttctt tctctgggtt ttcactgagc acttttggta tgggtgtagg ctggattcgt  120
cagccttcag ggaagggtct ggagtggctg gcacacattt ggtgggatga tgataagtac  180
tataacccag ccctgaagag tcggctcaca atctccaagg atacctccaa aaaccaggta  240
ttcctcaaga tcgccaatgt ggacactgca gatactgcca catactactg tgctcgactg  300
ggttactacc cctactggtt cttcgatgtc tggggcacag ggaccacggt caccgtctcc  360
tca                                                                363

SEQ ID NO: 16            moltype = AA   length = 110
FEATURE                  Location/Qualifiers
source                   1..110
                         mol_type = protein
                         organism = Mus musculus
                         note = Monoclonal antibody 15M13A VL light chain variable
                          region
SEQUENCE: 16
QSVLTQPPSV SAAPGQKVTI SCSGSSSNIG NHYVSWYQQL PGTAPKLLIY DNNKRPSGIP   60
DRFSGSKSGT SATLGITGLQ TGDEADYYCG TWDTSLSAVV FGGGTKLTVL             110
```

```
SEQ ID NO: 17            moltype = AA   length = 8
FEATURE                  Location/Qualifiers
source                   1..8
                         mol_type = protein
                         organism = Mus musculus
                         note = 15M13A LC CDR1
SEQUENCE: 17
SSNIGNHY                                                              8

SEQ ID NO: 18            moltype =     length =
SEQUENCE: 18
000

SEQ ID NO: 19            moltype = AA   length = 11
FEATURE                  Location/Qualifiers
source                   1..11
                         mol_type = protein
                         organism = Mus musculus
                         note = 15M13A LC CDR3
SEQUENCE: 19
GTWDTSLSAV V                                                         11

SEQ ID NO: 20            moltype = DNA   length = 330
FEATURE                  Location/Qualifiers
source                   1..330
                         mol_type = genomic DNA
                         organism = Mus musculus
                         note = Antibody 15M13A VL light chain variable region
SEQUENCE: 20
cagtctgtgt tgacgcagcc gccctcagtg tctgcggccc caggacagaa ggtcaccatc    60
tcctgctctg gaagcagctc caacattggg aatcattatg tatcctggta ccagcagctc   120
ccaggaacag cccccaaact cctcatttat gacaataata agcgaccctc tgggattcct   180
gaccgattct ctggctccaa gtctggcacg tcagccaccc tgggcatcac cggactcag   240
actggggacg aggccgatta ttactgcgga acatgggata ccagcctgag tgctgtggta   300
ttcggcggag ggaccaagct gaccgtccta                                    330

SEQ ID NO: 21            moltype = AA   length = 121
FEATURE                  Location/Qualifiers
source                   1..121
                         mol_type = protein
                         organism = Mus musculus
                         note = Monoclonal antibody 17D08A VH heavy chain variable
                          region
SEQUENCE: 21
EVQLVESGGG LVQPGGSLKL SCAASGFTFS GSAIHWVRQA SGKGLEWVGR IRSKVNSYAT    60
AYAASVKGRF TISRDDSKNT AYLQMNSLKT EDTAVYYCTR HAPNFDAFDI WGQGTMVTVS   120
S                                                                  121

SEQ ID NO: 22            moltype = AA   length = 8
FEATURE                  Location/Qualifiers
source                   1..8
                         mol_type = protein
                         organism = Mus musculus
                         note = 17D08A HC CDR1
SEQUENCE: 22
GFTFSGSA                                                              8

SEQ ID NO: 23            moltype = AA   length = 10
FEATURE                  Location/Qualifiers
source                   1..10
                         mol_type = protein
                         organism = Mus musculus
                         note = 17D08A HC CDR2
SEQUENCE: 23
IRSKVNSYAT                                                           10

SEQ ID NO: 24            moltype = AA   length = 12
FEATURE                  Location/Qualifiers
source                   1..12
                         mol_type = protein
                         organism = Mus musculus
                         note = 17D08A HC CDR3
SEQUENCE: 24
TRHAPNFDAF DI                                                        12

SEQ ID NO: 25            moltype = DNA   length = 363
FEATURE                  Location/Qualifiers
source                   1..363
```

```
                              mol_type = genomic DNA
                              organism = Mus musculus
                              note = Antibody 17D08A VH heavy chain variable region
SEQUENCE: 25
gaggtgcagt tggtggagtc cggggggaggc ttggtccagc ctggggggtc cctgaaactc      60
tcctgtgcag cctctgggtt caccttcagt ggctctgcta tacactgggt ccgccaggct     120
tccgggaaag gctgagtg ggttggccgt attagaagca aagttaacag ttacgcgaca       180
gcatatgctg cgtcggtgaa aggcaggttc accatctcca gagatgattc aaagaatacg     240
gcgtatctgc aaatgaatag cctgaaaacc gaggacacgg ccgtgtatta ctgtactaga     300
catcccccta actttgatgc ttttgatatc tggggccaag gacaatggt caccgtctct      360
tca                                                                   363

SEQ ID NO: 26                 moltype = AA  length = 110
FEATURE                       Location/Qualifiers
source                        1..110
                              mol_type = protein
                              organism = Mus musculus
                              note = Monoclonal antibody 17D08A VL light chain variable
                                region
SEQUENCE: 26
QSVLTQPPSV SAAPGQKVTI SCSGYSSNIG NHYVSWYQQL PGTAPKFFIY DNNKRPSGIP      60
DRFSGSKSGT SATLGITGLQ TGDEADYYCG TWDSSLITYV FGTGTKVTVL                110

SEQ ID NO: 27                 moltype = AA  length = 8
FEATURE                       Location/Qualifiers
source                        1..8
                              mol_type = protein
                              organism = Mus musculus
                              note = 17D08A LC CDR1
SEQUENCE: 27
SSNIGNHY                                                                8

SEQ ID NO: 28                 moltype =   length =
SEQUENCE: 28
000

SEQ ID NO: 29                 moltype = AA  length = 11
FEATURE                       Location/Qualifiers
source                        1..11
                              mol_type = protein
                              organism = Mus musculus
                              note = 17D08A LC CDR3
SEQUENCE: 29
GTWDSSLITY V                                                           11

SEQ ID NO: 30                 moltype = DNA  length = 330
FEATURE                       Location/Qualifiers
source                        1..330
                              mol_type = genomic DNA
                              organism = Mus musculus
                              note = Antibody 17D08A VL light chain variable region
SEQUENCE: 30
cagtctgtgt tgacgcagcc gccctcagtg tctgcggccc caggacagaa ggtcaccatc      60
tcctgctctg gatacagctc caacattggg aatcattatg tatcctggta ccagcagctc     120
ccaggaacag cccccaaatt tttttatttat gacaataata agcgaccctc agggattcct    180
gaccgattct ctggctccaa gtctggcacg tcagccaccc tgggcatcac cggactccag     240
actggggacg aggccgatta ttactgcgga acatgggata gcagcctgat tacttatgtc     300
ttcggaactg ggaccaaggt caccgtccta                                      330

SEQ ID NO: 31                 moltype = AA  length = 116
FEATURE                       Location/Qualifiers
source                        1..116
                              mol_type = protein
                              organism = Mus musculus
                              note = Monoclonal antibody 17H05A VH heavy chain variable
                                region
SEQUENCE: 31
EVQLVESGGG SVQPGGSLRL SCAASGFTFS SYWMHWVRQV PGKGLVWVSR INSDGSITSY       60
ADSVKGRFTI SRDNAKNTLY LQMNSLRAEN TAVYYCARGG GSLDYWGQGT LVTVSS         116

SEQ ID NO: 32                 moltype = AA  length = 8
FEATURE                       Location/Qualifiers
source                        1..8
                              mol_type = protein
                              organism = Mus musculus
                              note = 17H05A HC CDR1
SEQUENCE: 32
GFTFSSYW                                                                8
```

| SEQ ID NO: 33 | moltype = AA length = 8 |
| --- | --- |
| FEATURE | Location/Qualifiers |
| source | 1..8 |
| | mol_type = protein |
| | organism = Mus musculus |
| | note = 17H05A HC CDR2 |

SEQUENCE: 33
INSDGSIT                                                                          8

| SEQ ID NO: 34 | moltype = AA length = 9 |
| --- | --- |
| FEATURE | Location/Qualifiers |
| source | 1..9 |
| | mol_type = protein |
| | organism = Mus musculus |
| | note = 17H05A HC CDR3 |

SEQUENCE: 34
ARGGGSLDY                                                                         9

| SEQ ID NO: 35 | moltype = DNA length = 348 |
| --- | --- |
| FEATURE | Location/Qualifiers |
| source | 1..348 |
| | mol_type = genomic DNA |
| | organism = Mus musculus |
| | note = Antibody 17H05A VH heavy chain variable region |

SEQUENCE: 35
```
gaggtgcagc tggtggagtc cggggggaggc tcagttcagc ctggggggtc cctgagactc    60
tcctgtgcag cctctggatt caccttcagt agttactgga tgcactgggt ccgccaagtt   120
ccagggaagg ggctggtgtg gtctcacgt attaatagtg atgggagtat cacaagctac    180
gcggactccg tgaagggccg attcaccatc tccagagaca cgccaagaa cacgctgtat    240
ctgcaaatga acagtctgag agccgaaaac acggctgtgt attactgtgc aagagggggt   300
gggagtcttg actactgggg ccagggaacc ctggtcaccg tctcctca                348
```

| SEQ ID NO: 36 | moltype = AA length = 110 |
| --- | --- |
| FEATURE | Location/Qualifiers |
| source | 1..110 |
| | mol_type = protein |
| | organism = Mus musculus |
| | note = Monoclonal antibody 17H05A VL light chain variable region |

SEQUENCE: 36
```
QSVLTQPPSV SAAPGQKVTI SCSGSSSNIG NYYVSWYQQL PGTAPKLLIY DNHKRPSGIP    60
DRFSGSKSGT SATLGITGLQ TGDEADYYCG TWDSSLSAVV FGGGTKLTVL              110
```

| SEQ ID NO: 37 | moltype = AA length = 8 |
| --- | --- |
| FEATURE | Location/Qualifiers |
| source | 1..8 |
| | mol_type = protein |
| | organism = Mus musculus |
| | note = 17H05A LC CDR1 |

SEQUENCE: 37
SSNIGNYY                                                                          8

| SEQ ID NO: 38 | moltype = length = |
| --- | --- |

SEQUENCE: 38
000

| SEQ ID NO: 39 | moltype = AA length = 11 |
| --- | --- |
| FEATURE | Location/Qualifiers |
| source | 1..11 |
| | mol_type = protein |
| | organism = Mus musculus |
| | note = 17H05A LC CDR3 |

SEQUENCE: 39
GTWDSSLSAV V                                                                     11

| SEQ ID NO: 40 | moltype = DNA length = 330 |
| --- | --- |
| FEATURE | Location/Qualifiers |
| source | 1..330 |
| | mol_type = genomic DNA |
| | organism = Mus musculus |
| | note = Antibody 17H05A VL light chain variable region |

SEQUENCE: 40
```
cagtctgtgt tgacgcagcc gccctcagtg tctgcggccc caggacagaa ggtcaccatc    60
tcctgctctg gaagcagctc caacattggg aattattatg tatcctggta ccagcagctc   120
ccaggaacag cccccaaact cctcatttat gacaatcata agcgaccctc aggattcct    180
gaccgattct ctggctccaa gtctggcacg tcagccaccc tgggcatcac cggactccag   240
actggggacg aggccgatta ttactgcgga acatgggata gtagcctgag tgctgtggta   300
ttcggcggag ggaccaagct gaccgtccta                                     330
```

| | | |
|---|---|---|
| SEQ ID NO: 41<br>FEATURE<br>source | moltype = AA length = 121<br>Location/Qualifiers<br>1..121<br>mol_type = protein<br>organism = Mus musculus<br>note = Monoclonal antibody 17P04A VH heavy chain variable<br>region | |
| SEQUENCE: 41<br>EVQLVESGGG LVKPGGSLRL SCAASGFTLS SFSMNWVRQA PGKGLEWVSS ISSRRTYIYY<br>ADSAKGRFTF SRDNAKNSLY LQMNSLRAED SAVYYCARGG YIGSPNAYDI WGQGTMVTVS<br>S | | 60<br>120<br>121 |
| SEQ ID NO: 42<br>FEATURE<br>source | moltype = AA length = 8<br>Location/Qualifiers<br>1..8<br>mol_type = protein<br>organism = Mus musculus<br>note = 17P04A HC CDR1 | |
| SEQUENCE: 42<br>GFTLSSFS | | 8 |
| SEQ ID NO: 43<br>FEATURE<br>source | moltype = AA length = 8<br>Location/Qualifiers<br>1..8<br>mol_type = protein<br>organism = Mus musculus<br>note = 17P04A HC CDR2 | |
| SEQUENCE: 43<br>ISSRRTYI | | 8 |
| SEQ ID NO: 44<br>FEATURE<br>source | moltype = AA length = 14<br>Location/Qualifiers<br>1..14<br>mol_type = protein<br>organism = Mus musculus<br>note = 17P04A HC CDR3 | |
| SEQUENCE: 44<br>ARGGYIGSPN AYDI | | 14 |
| SEQ ID NO: 45<br>FEATURE<br>source | moltype = DNA length = 363<br>Location/Qualifiers<br>1..363<br>mol_type = genomic DNA<br>organism = Mus musculus<br>note = Antibody 17P04A VH heavy chain variable region | |
| SEQUENCE: 45<br>gaggtgcaac tggtggagtc tgggggaggc ctggtcaagc ctggggggtc cctgagactc<br>tcctgtgcag cctctggatt caccctcagt agttttagca tgaactgggt ccgccaggct<br>ccagggaagg gctggagtg gtctcatcc attagtagtc gtaggactta catatactac<br>gcagactcag cgaagggccg attcaccttc tccagagaca cgccaagaa ctcactgtat<br>ctgcaaatga acagcctgag agccgaggac tcggctgtgt attactgtgc gagaggggga<br>tatattggga gccccaatgc ctatgatatc tggggccaag ggacaatggt caccgtctct<br>tca | | 60<br>120<br>180<br>240<br>300<br>360<br>363 |
| SEQ ID NO: 46<br>FEATURE<br>source | moltype = AA length = 109<br>Location/Qualifiers<br>1..109<br>mol_type = protein<br>organism = Mus musculus<br>note = Monoclonal antibody 17P04A VL light chain variable<br>region | |
| SEQUENCE: 46<br>QTVVTQEPSL TVSPGGTVTL TCASSTGAVT SDYYPNWFQQ KPGQAPRALI YSASTKHSWT<br>PARFSGSLLG GKAALTLSGV QPEDEADYYC LLYYGGAWVF GGGTKLTVL | | 60<br>109 |
| SEQ ID NO: 47<br>FEATURE<br>source | moltype = AA length = 9<br>Location/Qualifiers<br>1..9<br>mol_type = protein<br>organism = Mus musculus<br>note = 17P04A LC CDR1 | |
| SEQUENCE: 47<br>TGAVTSDYY | | 9 |
| SEQ ID NO: 48<br>SEQUENCE: 48<br>000 | moltype = length = | |
| SEQ ID NO: 49 | moltype = AA length = 9 | |

```
FEATURE                 Location/Qualifiers
source                  1..9
                        mol_type = protein
                        organism = Mus musculus
                        note = 17P04A LC CDR3
SEQUENCE: 49
LLYYGGAWV                                                                 9

SEQ ID NO: 50           moltype = DNA   length = 327
FEATURE                 Location/Qualifiers
source                  1..327
                        mol_type = genomic DNA
                        organism = Mus musculus
                        note = Antibody 17P04A VL light chain variable region
SEQUENCE: 50
cagactgtgg tgactcagga gccctcactg actgtgtccc caggaggggac agtcactctc        60
acctgtgctt ccagcactgg agcagtcacc agtgattact atccaaactg gttccagcag       120
aaacctggac aagcacccag ggcactgatt tatagtgcaa gcaccaaaca ctcctggacc       180
cctgcccggt tctcaggctc cctccttggg ggcaaagctg ccctgacact gtcaggtgtg       240
cagcctgagg acgaggctga ctattactgc ctgctctact atggtggtgc ttgggtgttc       300
ggcggaggga ccaagctgac cgtccta                                           327

SEQ ID NO: 51           moltype = AA   length = 116
FEATURE                 Location/Qualifiers
source                  1..116
                        mol_type = protein
                        organism = Mus musculus
                        note = Monoclonal antibody 18F06A VH heavy chain variable
                         region
SEQUENCE: 51
EVQLVESGGG LVQPGGSLRL SCAASGFTFS SYWMHWVRQA PGKGLVWVSR INRDGSTTSY         60
ADSVKGRFTI SRDNAKNTLY LQMNRLRAED TAVYYCARGG GAFDIWGQGT MVTVSS            116

SEQ ID NO: 52           moltype = AA   length = 8
FEATURE                 Location/Qualifiers
source                  1..8
                        mol_type = protein
                        organism = Mus musculus
                        note = 18F06A HC CDR1
SEQUENCE: 52
GFTFSSYW                                                                  8

SEQ ID NO: 53           moltype = AA   length = 8
FEATURE                 Location/Qualifiers
source                  1..8
                        mol_type = protein
                        organism = Mus musculus
                        note = 18F06A HC CDR2
SEQUENCE: 53
INRDGSTT                                                                  8

SEQ ID NO: 54           moltype = AA   length = 9
FEATURE                 Location/Qualifiers
source                  1..9
                        mol_type = protein
                        organism = Mus musculus
                        note = 18F06A HC CDR3
SEQUENCE: 54
ARGGGAFDI                                                                 9

SEQ ID NO: 55           moltype = DNA   length = 348
FEATURE                 Location/Qualifiers
source                  1..348
                        mol_type = genomic DNA
                        organism = Mus musculus
                        note = Antibody 18F06A VH heavy chain variable region
SEQUENCE: 55
gaggtgcagc tggtggagtc cgggggaggc ttagttcagc ctggggggtc cctgagactc         60
tcctgtgcag cctctggatt cacccttcagt agctactgga tgcactgggt ccgccaagct       120
ccagggaagg ggctggtgtg ggtctcacgt attaataggg atgggagtac acaagctac         180
gcggactccg tgaagggccg attcaccatc tccagagaca acgccaagaa cacgctgtat       240
ctgcaaatga acaggctgag agccgaggac acggctgtgt attactgtgc aagaggaggg       300
ggtgcttttg atatctgggg ccaagggaca atggtcaccg tctcttca                    348

SEQ ID NO: 56           moltype = AA   length = 110
FEATURE                 Location/Qualifiers
source                  1..110
                        mol_type = protein
                        organism = Mus musculus
```

```
                            note = Monoclonal antibody 18F06A VL light chain variable
                               region
SEQUENCE: 56
QSVLTQPPSV SAAPGQKVTI SCSGSSSNIG NYYVSWYQQL PGTAPKLLIY DNNKRPSGIP      60
DRFSASKSGT SATLGITGLQ TGDEADYYCG TWDDSLSAVV FGGGTKLTVL                110

SEQ ID NO: 57           moltype = AA  length = 8
FEATURE                 Location/Qualifiers
source                  1..8
                        mol_type = protein
                        organism = Mus musculus
                        note = 18F06A LC CDR1
SEQUENCE: 57
SSNIGNYY                                                                8

SEQ ID NO: 58           moltype =    length =
SEQUENCE: 58
000

SEQ ID NO: 59           moltype = AA  length = 11
FEATURE                 Location/Qualifiers
source                  1..11
                        mol_type = protein
                        organism = Mus musculus
                        note = 18F06A LC CDR3
SEQUENCE: 59
GTWDDSLSAV V                                                           11

SEQ ID NO: 60           moltype = DNA  length = 330
FEATURE                 Location/Qualifiers
source                  1..330
                        mol_type = genomic DNA
                        organism = Mus musculus
                        note = Antibody 18F06A VL light chain variable region
SEQUENCE: 60
cagtctgtgt tgacgcagcc gccctcagtg tctgcggccc caggacagaa ggtcaccatc      60
tcctgctctg gaagcagctc caacattggg aattattatg tatcctggta ccaacaactc     120
ccaggaacag ccccccaaact cctcatttat gacaataata gcgaccctc agggattcct     180
gaccgattct ctgcctccaa gtctggcacg tcagccaccc tgggcatcac cggactccag     240
actggggacg aggccgatta ttactgcgga acatgggatg acagcctgag tgctgtggta     300
ttcggcggag ggaccaagct gaccgtccta                                      330

SEQ ID NO: 61           moltype = AA  length = 121
FEATURE                 Location/Qualifiers
source                  1..121
                        mol_type = protein
                        organism = Mus musculus
                        note = Monoclonal antibody 18P01A VH heavy chain variable
                           region
SEQUENCE: 61
EVQLVESGGG LVQPGGSLKL SCAVSGFTFS GSAMHWVRQA SGKGLEWVGR IRSKANSYAT      60
AYAASVKGRF TISRDDSKNT AFLQMNSLKT EDTAVYYCTS HAPNFDAFDI WGQGTMVTVS     120
S                                                                    121

SEQ ID NO: 62           moltype = AA  length = 8
FEATURE                 Location/Qualifiers
source                  1..8
                        mol_type = protein
                        organism = Mus musculus
                        note = 18P01A HC CDR1
SEQUENCE: 62
GFTFSGSA                                                                8

SEQ ID NO: 63           moltype = AA  length = 10
FEATURE                 Location/Qualifiers
source                  1..10
                        mol_type = protein
                        organism = Mus musculus
                        note = 18P01A HC CDR2
SEQUENCE: 63
IRSKANSYAT                                                             10

SEQ ID NO: 64           moltype = AA  length = 12
FEATURE                 Location/Qualifiers
source                  1..12
                        mol_type = protein
                        organism = Mus musculus
                        note = 18P01A HC CDR3
SEQUENCE: 64
```

TSHAPNFDAF DI                                                                       12

SEQ ID NO: 65           moltype = DNA   length = 363
FEATURE                 Location/Qualifiers
source                  1..363
                        mol_type = genomic DNA
                        organism = Mus musculus
                        note = Antibody 18P01A VH heavy chain variable region
SEQUENCE: 65
gaggtgcagc tggtggagtc cggggggaggc ttggtccagc ctggggggtc cctgaaactc      60
tcctgtgcag tctctgggtt caccttcagt ggctctgcta tgcactgggt ccgccaggct     120
tccgggaaag gctggagtg gttggccgt attagaagca aagctaacag ctacgcgaca       180
gcatatgctg cgtcggtgaa aggcaggttc accatctcca gagatgattc aaagaacacg    240
gcgttttttgc aaatgaacag cctgaaaacc gaggacacgg ccgtgtatta ctgtactagc   300
catgccccta attttgatgc ttttgatatc tggggccaag ggacgatggt caccgtctct   360
tca                                                                   363

SEQ ID NO: 66           moltype = AA   length = 110
FEATURE                 Location/Qualifiers
source                  1..110
                        mol_type = protein
                        organism = Mus musculus
                        note = Monoclonal antibody 18P01A VL light chain variable
                         region
SEQUENCE: 66
QSVLTQPPSV SAAPGQKVTI SCSGSSSNIG NHYVSWYQQL PGTAPKFFIY DNSKRPSGIP     60
DRFSGSKSGT SATLGITGLQ TGDEADYYCG TWDSSLSTYV FGTGTKVTVL               110

SEQ ID NO: 67           moltype = AA   length = 8
FEATURE                 Location/Qualifiers
source                  1..8
                        mol_type = protein
                        organism = Mus musculus
                        note = 18P01A LC CDR1
SEQUENCE: 67
SSNIGNHY                                                                8

SEQ ID NO: 68           moltype =    length =
SEQUENCE: 68
000

SEQ ID NO: 69           moltype = AA   length = 11
FEATURE                 Location/Qualifiers
source                  1..11
                        mol_type = protein
                        organism = Mus musculus
                        note = 18P01A LC CDR3
SEQUENCE: 69
GTWDSSLSTY V                                                           11

SEQ ID NO: 70           moltype = DNA   length = 330
FEATURE                 Location/Qualifiers
source                  1..330
                        mol_type = genomic DNA
                        organism = Mus musculus
                        note = Antibody 18P01A VL light chain variable region
SEQUENCE: 70
cagtctgtgt tgacgcagcc gccctcagtg tctgcggccc caggacagaa ggtcaccatc     60
tcctgctctg gaagcagctc caacattggg aatcattatg tatcctggta ccagcagctc   120
ccaggaacag ccccccaaatt cttcatttat gacaatagta agcgaccctc agggattcct   180
gaccgattct ctggctccaa gtctggcacg tcagccaccc tgggcatcac cggactccag   240
actggggacg aggccgatta ttactgcgga acatgggata gcagcctgag tacttatgtc   300
ttcggaactg ggaccaaggt caccgtccta                                     330

SEQ ID NO: 71           moltype = AA   length = 121
FEATURE                 Location/Qualifiers
source                  1..121
                        mol_type = protein
                        organism = Mus musculus
                        note = Monoclonal antibody 20007A VH heavy chain variable
                         region
SEQUENCE: 71
EVQLVESGGG LVQPGGSLKL SCAVSGFTFS GSAIHWVRQA SGKGLEWVGR IRSKVNSYAT      60
VYAASVKGRF TISRDDSKNT AFLQMNSLKT EDTAVYYCTS HAPIFDAFDI WGQGTMVTVS    120
S                                                                    121

SEQ ID NO: 72           moltype = AA   length = 8
FEATURE                 Location/Qualifiers
source                  1..8

```
                        mol_type = protein
                        organism = Mus musculus
                        note = 20007A HC CDR1
SEQUENCE: 72
GFTFSGSA                                                               8

SEQ ID NO: 73           moltype = AA  length = 10
FEATURE                 Location/Qualifiers
source                  1..10
                        mol_type = protein
                        organism = Mus musculus
                        note = 20007A HC CDR2
SEQUENCE: 73
IRSKVNSYAT                                                            10

SEQ ID NO: 74           moltype = AA  length = 12
FEATURE                 Location/Qualifiers
source                  1..12
                        mol_type = protein
                        organism = Mus musculus
                        note = 20007A HC CDR3
SEQUENCE: 74
TSHAPIFDAF DI                                                         12

SEQ ID NO: 75           moltype = DNA  length = 363
FEATURE                 Location/Qualifiers
source                  1..363
                        mol_type = genomic DNA
                        organism = Mus musculus
                        note = Antibody 20007A VH heavy chain variable region
SEQUENCE: 75
gaggtgcagc tggtggagtc cgggggaggc ttggtccagc ctgggggtc cctaaaactc       60
tcctgtgcag tctctgggtt caccttcagt ggctctgcta tacactgggt ccgccaggct    120
tccgggaaag gctggagtg ggttggccgt attagaagca agtaatag ttacgcgaca        180
gtatatgctg cgtcggtgaa aggcaggttc accatctcca gagatgattc aaagaacacg    240
gcgtttttgc aaatgaacag cctgaaaacc gaggacacgg ccgtgtatta ctgtactagc    300
catgccccta ttttgatgc ttttgatatc tggggccaag ggacgatggt caccgtctct    360
tca                                                                  363

SEQ ID NO: 76           moltype = AA  length = 110
FEATURE                 Location/Qualifiers
source                  1..110
                        mol_type = protein
                        organism = Mus musculus
                        note = Monoclonal antibody 20007A VL light chain variable
                        region
SEQUENCE: 76
QSVLTQPPSV SAAPGQKVTI SCSGSSSNIG NHYVSWYQQL PGTAPKFLIY DNSKRPSGIP     60
DRFSGSKSGT SATLGITGLQ TGDEADYYCG TWDSSLSTYF FGTGTKVTVL              110

SEQ ID NO: 77           moltype = AA  length = 8
FEATURE                 Location/Qualifiers
source                  1..8
                        mol_type = protein
                        organism = Mus musculus
                        note = 20007A LC CDR1
SEQUENCE: 77
SSNIGNHY                                                               8

SEQ ID NO: 78           moltype =   length =
SEQUENCE: 78
000

SEQ ID NO: 79           moltype = AA  length = 11
FEATURE                 Location/Qualifiers
source                  1..11
                        mol_type = protein
                        organism = Mus musculus
                        note = 20007A LC CDR3
SEQUENCE: 79
GTWDSSLSTY F                                                          11

SEQ ID NO: 80           moltype = DNA  length = 330
FEATURE                 Location/Qualifiers
source                  1..330
                        mol_type = genomic DNA
                        organism = Mus musculus
                        note = Antibody 20007A VL light chain variable region
SEQUENCE: 80
```

```
cagtctgtgt tgacgcagcc gccctcagtg tctgcggccc caggacagaa ggtcaccatc    60
tcctgctctg gaagcagctc caacattggg aatcattatg tatcctggta ccagcagctc   120
ccaggaacag cccccaaatt cctcatttat gacaatagta agcgaccctc agggattcct   180
gaccgattct ctggctccaa gtctggcacg tcagccaccc tgggcatcac cggactccag   240
actgggacg aggccgatta ttactgcgga acatgggata gcagcctgag tacttatttc   300
ttcggaactg ggaccaaggt caccgtccta                                     330

SEQ ID NO: 81           moltype = AA   length = 116
FEATURE                 Location/Qualifiers
source                  1..116
                        mol_type = protein
                        organism = Mus musculus
                        note = Monoclonal antibody 20011A VH heavy chain variable
                         region
SEQUENCE: 81
EVQLVESGGG LVQPGGSLRL SCAASGFTFS SYWMHWVRQA PGKGLAWVAR INSDGSSTSY    60
ADSVKGRFTI SRDNAKNTLY LQMNSLRAED TAVYYCARGG GLFDYWGQGT LVTVSS       116

SEQ ID NO: 82           moltype = AA   length = 8
FEATURE                 Location/Qualifiers
source                  1..8
                        mol_type = protein
                        organism = Mus musculus
                        note = 20011A HC CDR1
SEQUENCE: 82
GFTFSSYW                                                               8

SEQ ID NO: 83           moltype = AA   length = 8
FEATURE                 Location/Qualifiers
source                  1..8
                        mol_type = protein
                        organism = Mus musculus
                        note = 20011A HC CDR2
SEQUENCE: 83
INSDGSST                                                               8

SEQ ID NO: 84           moltype = AA   length = 9
FEATURE                 Location/Qualifiers
source                  1..9
                        mol_type = protein
                        organism = Mus musculus
                        note = 20011A HC CDR3
SEQUENCE: 84
ARGGGLFDY                                                              9

SEQ ID NO: 85           moltype = DNA   length = 348
FEATURE                 Location/Qualifiers
source                  1..348
                        mol_type = genomic DNA
                        organism = Mus musculus
                        note = Antibody 20011A VH heavy chain variable region
SEQUENCE: 85
gaggtgcagc tggtggagtc cggggggaggc ttagttcagc ctgggggtc cctgagactc    60
tcctgtgcag cctctggatt caccttcagt agctactgga tgcactgggt ccgccaagct   120
ccagggaagg ggctggagtg ggtcgcacgt attaatagtg atggagtag cacaagctac    180
gcggactccg tgaagggccg attcaccatc tccagagaca acgccaagaa cacgctgtat   240
ctgcaaatga acagtctgag agccgaggac acggctgtgt attactgtgc aagaggaggg   300
ggattatttg actactgggg ccagggaacc ctggtcaccg tctcctca                348

SEQ ID NO: 86           moltype = AA   length = 110
FEATURE                 Location/Qualifiers
source                  1..110
                        mol_type = protein
                        organism = Mus musculus
                        note = Monoclonal antibody 20011A VL light chain variable
                         region
SEQUENCE: 86
QSVLTQPPSV SAAPGQKVTI SCSGSSSNIG NHYVSWYQQL PGTAPKLLIY DNNKRPSGIP    60
DRFSGSKSGT SATLGITGLQ TGDEADYYCG TWDSSLGAVL FGGGTKLTVL              110

SEQ ID NO: 87           moltype = AA   length = 8
FEATURE                 Location/Qualifiers
source                  1..8
                        mol_type = protein
                        organism = Mus musculus
                        note = 20011A LC CDR1
SEQUENCE: 87
SSNIGNHY                                                               8
```

```
SEQ ID NO: 88           moltype =    length =
SEQUENCE: 88
000

SEQ ID NO: 89           moltype = AA   length = 11
FEATURE                 Location/Qualifiers
source                  1..11
                        mol_type = protein
                        organism = Mus musculus
                        note = 20O11A LC CDR3
SEQUENCE: 89
GTWDSSLGAV L                                                            11

SEQ ID NO: 90           moltype = DNA   length = 330
FEATURE                 Location/Qualifiers
source                  1..330
                        mol_type = genomic DNA
                        organism = Mus musculus
                        note = Antibody 20O11A VL light chain variable region
SEQUENCE: 90
cagtctgtgt tgacgcagcc gccctcagtt tctgcggccc caggacagaa ggtcaccatc    60
tcctgctctg gaagcagctc caacattggg aatcattatg tatcctggta ccagcagctc   120
ccaggaacag ccccaaaact cctcatttat gacaataata gcgaccctc agggattcct    180
gaccgattct ctggctccaa gtctggcacg tcagccaccc tgggcatcac cggactccag   240
actgggacg aggccgatta ttactgcgga acatgggata gcagcctggg tgctgtgcta    300
ttcggcggag ggaccaagct gaccgtccta                                    330

SEQ ID NO: 91           moltype = AA   length = 116
FEATURE                 Location/Qualifiers
source                  1..116
                        mol_type = protein
                        organism = Mus musculus
                        note = Monoclonal antibody 21F12A VH heavy chain variable
                         region
SEQUENCE: 91
EVQLAESGGG SVQPGGSLRL SCAASGFTFS SYWMHWVRQV PGKGLVWVSR INSDGSTTTY     60
ADSVKGRFTI SRDNAKNTLY LQMNSLRAED TAVYYCARGG GSLDYWGQGT LVTVSS        116

SEQ ID NO: 92           moltype = AA   length = 8
FEATURE                 Location/Qualifiers
source                  1..8
                        mol_type = protein
                        organism = Mus musculus
                        note = 21F12A HC CDR1
SEQUENCE: 92
GFTFSSYW                                                              8

SEQ ID NO: 93           moltype = AA   length = 8
FEATURE                 Location/Qualifiers
source                  1..8
                        mol_type = protein
                        organism = Mus musculus
                        note = 21F12A HC CDR2
SEQUENCE: 93
INSDGSTT                                                              8

SEQ ID NO: 94           moltype = AA   length = 9
FEATURE                 Location/Qualifiers
source                  1..9
                        mol_type = protein
                        organism = Mus musculus
                        note = 21F12A HC CDR3
SEQUENCE: 94
ARGGGSLDY                                                             9

SEQ ID NO: 95           moltype = DNA   length = 348
FEATURE                 Location/Qualifiers
source                  1..348
                        mol_type = genomic DNA
                        organism = Mus musculus
                        note = Antibody 21F12A VH heavy chain variable region
SEQUENCE: 95
gaggtgcagc tggcggagtc cggggagggc tcagttcagc ctggggggtc cctgagactc     60
tcctgtgcag cctctggatt cacttcagt agttactgga tgcactgggt ccgccaagtt    120
ccagggaagg ggctggtgtg ggtctcacg attaatagtg atgggagtac cacaacctac    180
gcggactccg tgaagggccg attcaccatc tccagagaca acgccaagaa cacgctgtat   240
ctgcaaatga acagtctgag agccgaggac acggctgtgt attactgtgc aagagggggt   300
gggagtcttg actactgggg ccaggaacc ctggtcaccg tctcctca                  348
```

```
SEQ ID NO: 96              moltype = AA   length = 110
FEATURE                    Location/Qualifiers
source                     1..110
                           mol_type = protein
                           organism = Mus musculus
                           note = Monoclonal antibody 21F12A VL light chain variable
                            region
SEQUENCE: 96
QSVLTQPPSV SAAPGQKVTI SCSGSSSNIG NYYVSWYQQL PGTAPKLLIY DNNKRPSGIP    60
DRFSGSKSGT SATLGITGLR TGDEADYYCG TWDSSLSAVV FGGGTKLTVL              110

SEQ ID NO: 97              moltype = AA   length = 8
FEATURE                    Location/Qualifiers
source                     1..8
                           mol_type = protein
                           organism = Mus musculus
                           note = 21F12A LC CDR1
SEQUENCE: 97
SSNIGNYY                                                              8

SEQ ID NO: 98              moltype =   length =
SEQUENCE: 98
000

SEQ ID NO: 99              moltype = AA   length = 11
FEATURE                    Location/Qualifiers
source                     1..11
                           mol_type = protein
                           organism = Mus musculus
                           note = 21F12A LC CDR3
SEQUENCE: 99
GTWDSSLSAV V                                                         11

SEQ ID NO: 100             moltype = DNA   length = 330
FEATURE                    Location/Qualifiers
source                     1..330
                           mol_type = genomic DNA
                           organism = Mus musculus
                           note = Antibody 21F12A VL light chain variable region
SEQUENCE: 100
cagtctgtgt tgacgcagcc gccctcagtg tctgcggccc caggacagaa ggtcaccatc    60
tcctgctctg gaagcagctc caacattggg aattattatg tatcctggta ccagcaactc   120
ccaggaacag cccccaaaact cctcatttat gacaataata gcgaccctc agggattcct   180
gaccgattct ctggctccaa gtctggcacg tcagccaccc tgggcatcac cggactccga   240
actggggacg aggccgatta ttactgcgga acatgggata gcagcctgag tgctgtggta   300
ttcggcggag ggaccaagct gaccgtccta                                    330

SEQ ID NO: 101             moltype = AA   length = 116
FEATURE                    Location/Qualifiers
source                     1..116
                           mol_type = protein
                           organism = Mus musculus
                           note = Monoclonal antibody 21G10A VH heavy chain variable
                            region
SEQUENCE: 101
EVQLVESGGG SVQPGGSLRL SCAASGFTFS SYWMHWVRQA PGKGLVWVSR INSDGSITTY    60
ADSVKGRFTI SRDNAKNTLY LQMNSLRAED TAVYYCARGG GSLDYWGQGT LVTVSS       116

SEQ ID NO: 102             moltype = AA   length = 8
FEATURE                    Location/Qualifiers
source                     1..8
                           mol_type = protein
                           organism = Mus musculus
                           note = 21G10A HC CDR1
SEQUENCE: 102
GFTFSSYW                                                              8

SEQ ID NO: 103             moltype = AA   length = 8
FEATURE                    Location/Qualifiers
source                     1..8
                           mol_type = protein
                           organism = Mus musculus
                           note = 21G10A HC CDR2
SEQUENCE: 103
INSDGSIT                                                              8

SEQ ID NO: 104             moltype = AA   length = 9
FEATURE                    Location/Qualifiers
source                     1..9
```

```
                              mol_type = protein
                              organism = Mus musculus
                              note = 21G10A HC CDR3
SEQUENCE: 104
ARGGGSLDY                                                                9

SEQ ID NO: 105                moltype = DNA   length = 348
FEATURE                       Location/Qualifiers
source                        1..348
                              mol_type = genomic DNA
                              organism = Mus musculus
                              note = Antibody 21G10A VH heavy chain variable region
SEQUENCE: 105
gaggtgcagc tggtggagtc cggggggaggc tcagttcagc tgggggggtc cctgagactc    60
tcctgtgcag cctctggatt caccttcagt agttactgga tgcactgggt ccgccaagct   120
ccagggaagg ggctggtgtg gtctcacgt attaatagtg atgggagtat cacaacctac    180
gcggactccg tgaagggccg attcaccatc tccagagaca cgccaagaa cacgctgtat    240
ctgcaaatga acagtctgag agccgaggac acggctgtgt attactgtgc aagagggggt   300
gggagtcttg actactgggg ccagggaacc ctggtcaccg tctcctca                348

SEQ ID NO: 106                moltype = AA   length = 110
FEATURE                       Location/Qualifiers
source                        1..110
                              mol_type = protein
                              organism = Mus musculus
                              note = Monoclonal antibody 21G10A VL light chain variable
                              region
SEQUENCE: 106
QSVLTQPPSV SAAPGQKVTI SCSGSSSNIG NYYVSWYQQL PGTAPKLLIY DNNKRPSGIP    60
DRFSGSKSGT SATLGITGLQ TGDEADYYCG TWDSSLSAVV FGGGTKLTVL              110

SEQ ID NO: 107                moltype = AA   length = 8
FEATURE                       Location/Qualifiers
source                        1..8
                              mol_type = protein
                              organism = Mus musculus
                              note = 21G10A LC CDR1
SEQUENCE: 107
SSNIGNYY                                                                 8

SEQ ID NO: 108                moltype =    length =
SEQUENCE: 108
000

SEQ ID NO: 109                moltype = AA   length = 11
FEATURE                       Location/Qualifiers
source                        1..11
                              mol_type = protein
                              organism = Mus musculus
                              note = 21G10A LC CDR3
SEQUENCE: 109
GTWDSSLSAV V                                                            11

SEQ ID NO: 110                moltype = DNA   length = 330
FEATURE                       Location/Qualifiers
source                        1..330
                              mol_type = genomic DNA
                              organism = Mus musculus
                              note = Antibody 21G10A VL light chain variable region
SEQUENCE: 110
cagtctgtgt tgacgcagcc gccctcagtg tctgcggccc caggacagaa ggtcaccatc     60
tcctgctctg gaagcagctc caacattggg aattattatg tatcctggta ccagcagctc   120
ccaggaacag cccccaaact cctcatttat gacaataata gcgaccctc agggattcct    180
gaccgattct ctggctccaa gtctggcacg tcagccaccc tgggcatcac cggactccag   240
actgggacg aggccgatta ttactgcgga acatgggata gcagcctgag tgctgtggta    300
ttcggcggag ggaccaagct gaccgtccta                                    330

SEQ ID NO: 111                moltype = AA   length = 117
FEATURE                       Location/Qualifiers
source                        1..117
                              mol_type = protein
                              organism = Mus musculus
                              note = Monoclonal antibody 21K12A VH heavy chain variable
                              region
SEQUENCE: 111
EVQLVESGGG LVKPGGSLRL SCAASGFTFS NAWMSWVRQA PGKGLEWVGR IKSKTDGGTR    60
DYAAPVKGRF TISRDDSKNT LYLQMNSLKT EDTAVYYCTT GYGEGYWGQG TLVTVSS      117

SEQ ID NO: 112                moltype = AA   length = 8
```

| | |
|---|---|
| FEATURE | Location/Qualifiers |
| source | 1..8 |
| | mol_type = protein |
| | organism = Mus musculus |
| | note = 21K12A HC CDR1 |

SEQUENCE: 112
GFTFSNAW                                                              8

| | |
|---|---|
| SEQ ID NO: 113 | moltype = AA   length = 10 |
| FEATURE | Location/Qualifiers |
| source | 1..10 |
| | mol_type = protein |
| | organism = Mus musculus |
| | note = 21K12A HC CDR2 |

SEQUENCE: 113
IKSKTDGGTR                                                           10

| | |
|---|---|
| SEQ ID NO: 114 | moltype = AA   length = 8 |
| FEATURE | Location/Qualifiers |
| source | 1..8 |
| | mol_type = protein |
| | organism = Mus musculus |
| | note = 21K12A HC CDR3 |

SEQUENCE: 114
TTGYGEGY                                                              8

| | |
|---|---|
| SEQ ID NO: 115 | moltype = DNA   length = 351 |
| FEATURE | Location/Qualifiers |
| source | 1..351 |
| | mol_type = genomic DNA |
| | organism = Mus musculus |
| | note = Antibody 21K12A VH heavy chain variable region |

SEQUENCE: 115
gaggtgcagc tggtggagtc tgggggaggc ttggtaaagc ctggggggtc ccttagactc    60
tcctgtgcag cctctggatt cactttcagt aacgcctgga tgagctgggt ccgccaggct   120
ccagggaagg ggctgagtg gttggccgt attaaaagca aaactgatgg tgggacaaga    180
gactacgctg cacccgtgaa aggcagattc accatctcaa gagatgattc aaaaaacacg   240
ctgtatctgc aaatgaacag cctgaaaacc gaggacacag ccgtgtatta ctgtaccaca   300
ggctacggtg aaggctactg gggccaggga accctggtca ccgtctcctc a           351

| | |
|---|---|
| SEQ ID NO: 116 | moltype = AA   length = 110 |
| FEATURE | Location/Qualifiers |
| source | 1..110 |
| | mol_type = protein |
| | organism = Mus musculus |
| | note = Monoclonal antibody 21K12A VL light chain variable region |

SEQUENCE: 116
QSVLTQPPSA SGTPGQRVTI SCSGSSSNIK SNTVNWYQQL PGTAPKLLIY RNNQRPSGVP    60
DRFSGSKSGT SASLAISGLQ SEDEADYYCA AWDDSLKGVV FGGGTDLTVL              110

| | |
|---|---|
| SEQ ID NO: 117 | moltype = AA   length = 8 |
| FEATURE | Location/Qualifiers |
| source | 1..8 |
| | mol_type = protein |
| | organism = Mus musculus |
| | note = 21K12A LC CDR1 |

SEQUENCE: 117
SSNIKSNT                                                              8

| | |
|---|---|
| SEQ ID NO: 118 | moltype =    length = |
| SEQUENCE: 118 | |
| 000 | |

| | |
|---|---|
| SEQ ID NO: 119 | moltype = AA   length = 11 |
| FEATURE | Location/Qualifiers |
| source | 1..11 |
| | mol_type = protein |
| | organism = Mus musculus |
| | note = 21K12A LC CDR3 |

SEQUENCE: 119
AAWDDSLKGV V                                                         11

| | |
|---|---|
| SEQ ID NO: 120 | moltype = DNA   length = 330 |
| FEATURE | Location/Qualifiers |
| source | 1..330 |
| | mol_type = genomic DNA |
| | organism = Mus musculus |
| | note = Antibody 21K12A VL light chain variable region |

| | | |
|---|---|---|
| SEQUENCE: 120 | | |
| cagtctgtgc tgactcagcc accctcagcg tctgggaccc cggggcagag ggtcaccatc | | 60 |
| tcttgttctg gaagcagctc caacatcaaa agtaatactg tcaactggta ccagcagctc | | 120 |
| ccgggaacgg cccccaaact cctcatctat aggaataatc agcggccctc agggggtccct | | 180 |
| gaccgattct ctggctccaa gtctggcacc tcagcctccc tggccatcag tgggctccag | | 240 |
| tctgaggatg aggctgatta ttactgcgca gcatgggatg acagcctgaa gggtgtggta | | 300 |
| ttcggcggag ggaccgatct gaccgtccta | | 330 |
| | | |
| SEQ ID NO: 121 | moltype = AA length = 117 | |
| FEATURE | Location/Qualifiers | |
| source | 1..117 | |
| | mol_type = protein | |
| | organism = Mus musculus | |
| | note = Monoclonal antibody 21P22A VH heavy chain variable region | |
| SEQUENCE: 121 | | |
| EVQLVESGGG LVKPGGSLRL SCAASGFTFS NAWMSWVRQA PGKGLEWVGR IKSKTDGGTT | | 60 |
| DYAAPVKGRF TISRDDSKNT LYLQMNSLKT EDTAVYYCTT GYGEGYWGQG TLVTVSS | | 117 |
| | | |
| SEQ ID NO: 122 | moltype = AA length = 8 | |
| FEATURE | Location/Qualifiers | |
| source | 1..8 | |
| | mol_type = protein | |
| | organism = Mus musculus | |
| | note = 21P22A HC CDR1 | |
| SEQUENCE: 122 | | |
| GFTFSNAW | | 8 |
| | | |
| SEQ ID NO: 123 | moltype = AA length = 10 | |
| FEATURE | Location/Qualifiers | |
| source | 1..10 | |
| | mol_type = protein | |
| | organism = Mus musculus | |
| | note = 21P22A HC CDR2 | |
| SEQUENCE: 123 | | |
| IKSKTDGGTT | | 10 |
| | | |
| SEQ ID NO: 124 | moltype = AA length = 8 | |
| FEATURE | Location/Qualifiers | |
| source | 1..8 | |
| | mol_type = protein | |
| | organism = Mus musculus | |
| | note = 21P22A HC CDR3 | |
| SEQUENCE: 124 | | |
| TTGYGEGY | | 8 |
| | | |
| SEQ ID NO: 125 | moltype = DNA length = 351 | |
| FEATURE | Location/Qualifiers | |
| source | 1..351 | |
| | mol_type = genomic DNA | |
| | organism = Mus musculus | |
| | note = Antibody21P22A VH heavy chain variable region | |
| SEQUENCE: 125 | | |
| gaggtgcagc tggtggagtc tgggggaggc ttggtaaagc ctgggggggtc ccttagactc | | 60 |
| tcctgtgcag cctctggatt cactttcagt aacgcctggt tgagctgggt ccgccaggct | | 120 |
| ccagggaagg ggctggagtg ggttggccgt attaaaagca aaactgatgg tgggacaaca | | 180 |
| gactacgctg cacccgtgaa aggcagattc accatctcaa gagatgattc aaaaaacacg | | 240 |
| ctgtatctgc aaatgaacag cctgaaaacc gaggacacag ccgtgtatta ctgtaccaca | | 300 |
| ggctacggtg aaggctactg gggccaggga accctggtca ccgtctcctc a | | 351 |
| | | |
| SEQ ID NO: 126 | moltype = AA length = 110 | |
| FEATURE | Location/Qualifiers | |
| source | 1..110 | |
| | mol_type = protein | |
| | organism = Mus musculus | |
| | note = Monoclonal antibody 21P22A VL light chain variable region | |
| SEQUENCE: 126 | | |
| QSVLTQPPSA SGTPGQRVTI SCSGSSSNIK SNTVNWYQQL PGTAPKLLIY RNNQRPSGVP | | 60 |
| DRFSGSKSGT SASLAISGLQ SEDEADYYCA AWDDSLKGVV FGGGTDLTVL | | 110 |
| | | |
| SEQ ID NO: 127 | moltype = AA length = 8 | |
| FEATURE | Location/Qualifiers | |
| source | 1..8 | |
| | mol_type = protein | |
| | organism = Mus musculus | |
| | note = 21P22A LC CDR1 | |
| SEQUENCE: 127 | | |
| SSNIKSNT | | 8 |

```
SEQ ID NO: 128          moltype =   length =
SEQUENCE: 128
000

SEQ ID NO: 129          moltype = AA  length = 11
FEATURE                 Location/Qualifiers
source                  1..11
                        mol_type = protein
                        organism = Mus musculus
                        note = 21P22A LC CDR3
SEQUENCE: 129
AAWDDSLKGV V                                                          11

SEQ ID NO: 130          moltype = DNA  length = 330
FEATURE                 Location/Qualifiers
source                  1..330
                        mol_type = genomic DNA
                        organism = Mus musculus
                        note = Antibody 21P22A VL light chain variable region
SEQUENCE: 130
cagtctgtgc tgactcagcc accctcagcg tctgggaccc ccgggcagag ggtcaccatc    60
tcttgttctg gaagcagctc caacatcaaa agtaatactg tcaactggta ccagcagctc  120
ccaggaacgg cccccaaact cctcatctat aggaataatc agcggccctc aggggtccct  180
gaccgattct ctggctccaa gtctggcacc tcagcctccc tggccatcag tgggctccag  240
tctgaggatg aggctgatta ttactgtgca gcatgggatg acagcctgaa gggtgtggta  300
ttcggcggag ggaccgatct gaccgtccta                                    330

SEQ ID NO: 131          moltype = AA  length = 117
FEATURE                 Location/Qualifiers
source                  1..117
                        mol_type = protein
                        organism = Mus musculus
                        note = Monoclonal antibody 22D04A VH heavy chain variable
                         region
SEQUENCE: 131
EVQLVESGGG LVKPGGSLRL SCAASGFTFS NAWMSWVRQA PGKGLEWVGR IKSKTDGGTR    60
DYAAPVKGRF TISRDDSKNT LYLQMNSLKT EDTAVYYCTT GYGEGYWGQG TLVTVSS      117

SEQ ID NO: 132          moltype = AA  length = 8
FEATURE                 Location/Qualifiers
source                  1..8
                        mol_type = protein
                        organism = Mus musculus
                        note = 22D04A HC CDR1
SEQUENCE: 132
GFTFSNAW                                                              8

SEQ ID NO: 133          moltype = AA  length = 10
FEATURE                 Location/Qualifiers
source                  1..10
                        mol_type = protein
                        organism = Mus musculus
                        note = 22D04A HC CDR2
SEQUENCE: 133
IKSKTDGGTR                                                           10

SEQ ID NO: 134          moltype = AA  length = 8
FEATURE                 Location/Qualifiers
source                  1..8
                        mol_type = protein
                        organism = Mus musculus
                        note = 22D04A HC CDR3
SEQUENCE: 134
TTGYGEGY                                                              8

SEQ ID NO: 135          moltype = DNA  length = 351
FEATURE                 Location/Qualifiers
source                  1..351
                        mol_type = genomic DNA
                        organism = Mus musculus
                        note = Antibody 22D04A VH heavy chain variable region
SEQUENCE: 135
gaggtgcagc tggtggagtc tgggggaggc ttggtaaagc ctggggggtc ccttagactc    60
tcctgtgcag cctctggatt cactttcagt aacgcctgga tgagctgggt ccgccaggct  120
ccagggaagg ggctggagtg ggttggccgt attaaaagca aaactgatgg tggacaaga   180
gactacgctg cacccgtgaa aggcagattc accatctcaa gagatgattc aaaaacacg   240
ctgtatctgc aaatgaacag cctgaaaacc gaggacacag ccgtgtatta ctgtaccaca  300
ggctacggtg aaggctactg ggccaggga acctggtca ccgtctcctc a              351
```

| | |
|---|---|
| SEQ ID NO: 136 | moltype = AA   length = 110 |
| FEATURE | Location/Qualifiers |
| source | 1..110 |
| | mol_type = protein |
| | organism = Mus musculus |
| | note = Monoclonal antibody 22D04A VL light chain variable region |

SEQUENCE: 136
```
QSVLTQPPSA SGTPGQRVTI SCSGSSSNIK SNTVNWYQQL PGTAPKLLIY RNNQRPSGVP     60
DRFSGSKSGT SASLAISGLQ SEDEADYYCA AWDDSLKGVV FGGGTDLTVL               110
```

| | |
|---|---|
| SEQ ID NO: 137 | moltype = AA   length = 8 |
| FEATURE | Location/Qualifiers |
| source | 1..8 |
| | mol_type = protein |
| | organism = Mus musculus |
| | note = 22D04A LC CDR1 |

SEQUENCE: 137
```
SSNIKSNT                                                              8
```

| | |
|---|---|
| SEQ ID NO: 138 | moltype =    length = |

SEQUENCE: 138
000

| | |
|---|---|
| SEQ ID NO: 139 | moltype = AA   length = 11 |
| FEATURE | Location/Qualifiers |
| source | 1..11 |
| | mol_type = protein |
| | organism = Mus musculus |
| | note = 22D04A LC CDR3 |

SEQUENCE: 139
```
AAWDDSLKGV V                                                         11
```

| | |
|---|---|
| SEQ ID NO: 140 | moltype = DNA   length = 330 |
| FEATURE | Location/Qualifiers |
| source | 1..330 |
| | mol_type = genomic DNA |
| | organism = Mus musculus |
| | note = Antibody 22D04A VL light chain variable region |

SEQUENCE: 140
```
cagtctgtgc tgactcagcc accctcagcg tctgggaccc ccgggcagag ggtcaccatc     60
tcttgttctg gaagcagctc caacatcaaa agtaatactg tcaactggta ccagcagctc    120
ccaggaacgg ccccccaaac tcctcatcta taggaataat cagcggcctc aggggtccct    180
gaccgattct ctggctccaa gtctggcacc tcagcctccc tggccatcag tgggctccag    240
tctgaggatg aggctgatta ttactgtgca gcatgggatg acagcctgaa gggtgtggta    300
ttcggcggag ggaccgatct gaccgtccta                                     330
```

| | |
|---|---|
| SEQ ID NO: 141 | moltype = AA   length = 121 |
| FEATURE | Location/Qualifiers |
| source | 1..121 |
| | mol_type = protein |
| | organism = Mus musculus |
| | note = Monoclonal antibody 22H10A VH heavy chain variable region |

SEQUENCE: 141
```
EMQLVESGGG LVKPGGSLRL SCAASGFTFS SYSMNWVRQA PGKGLEWVSS ISTRKNYIYY     60
ADSVQGRFIF SRDNAKNALY LQMNSLRAED SAVYYCTRGG YIRSPNAFDI WGQGTMVTVS    120
S                                                                   121
```

| | |
|---|---|
| SEQ ID NO: 142 | moltype = AA   length = 8 |
| FEATURE | Location/Qualifiers |
| source | 1..8 |
| | mol_type = protein |
| | organism = Mus musculus |
| | note = 22H10A HC CDR1 |

SEQUENCE: 142
```
GFTFSSYS                                                              8
```

| | |
|---|---|
| SEQ ID NO: 143 | moltype = AA   length = 8 |
| FEATURE | Location/Qualifiers |
| source | 1..8 |
| | mol_type = protein |
| | organism = Mus musculus |
| | note = 22H10A HC CDR2 |

SEQUENCE: 143
```
ISTRKNYI                                                              8
```

| | |
|---|---|
| SEQ ID NO: 144 | moltype = AA   length = 14 |

| FEATURE | Location/Qualifiers |
|---|---|
| source | 1..14<br>mol_type = protein<br>organism = Mus musculus<br>note = 22H10A HC CDR3 |

SEQUENCE: 144
TRGGYIRSPN AFDI                                                         14

| SEQ ID NO: 145 | moltype = DNA  length = 362 |
|---|---|
| FEATURE | Location/Qualifiers |
| source | 1..362<br>mol_type = genomic DNA<br>organism = Mus musculus<br>note = Antibody 22H10A VH heavy chain variable region |

SEQUENCE: 145
gagatgcagc tggtggagtc tgggggaggc ctggtcaagc ctggggggtc cctgagactc    60
tcctgtgcag cctctggatt caccttcagt agttattcca tgaactgggt ccgccaggct   120
ccagggaagg gactggagtg gtctcttcc atcagtactc gtaaaaatta tatatactac   180
gcagactcag tccagggccg attcatcttc tccagagaca cgccaagaa cgcactgtat   240
ctgcaaatga cagcctgag agccgaggat tcggctgttt attactgtac gagagggggga   300
tatattagga gccccaatgc ttttgatatc tggggccaag gacaatggt caccgtctct   360
tc                                                                  362

| SEQ ID NO: 146 | moltype = AA  length = 109 |
|---|---|
| FEATURE | Location/Qualifiers |
| source | 1..109<br>mol_type = protein<br>organism = Mus musculus<br>note = Monoclonal antibody 22H10A VL light chain variable region |

SEQUENCE: 146
QTVVTQEPSL TVSPGGTVTL TCASSTGTVT SGYFPNWLQQ KPGQAPRALI YSINNKHFWT    60
PARFSGSLLG GKAALTLSGV QPEDEAEYYC LLYYGGAWVF GGGTKLTVL               109

| SEQ ID NO: 147 | moltype = AA  length = 9 |
|---|---|
| FEATURE | Location/Qualifiers |
| source | 1..9<br>mol_type = protein<br>organism = Mus musculus<br>note = 22H10A LC CDR1 |

SEQUENCE: 147
TGTVTSGYF                                                             9

| SEQ ID NO: 148 | moltype =   length = |
|---|---|
SEQUENCE: 148
000

| SEQ ID NO: 149 | moltype = AA  length = 9 |
|---|---|
| FEATURE | Location/Qualifiers |
| source | 1..9<br>mol_type = protein<br>organism = Mus musculus<br>note = 22H10A LC CDR3 |

SEQUENCE: 149
LLYYGGAWV                                                             9

| SEQ ID NO: 150 | moltype = DNA  length = 327 |
|---|---|
| FEATURE | Location/Qualifiers |
| source | 1..327<br>mol_type = genomic DNA<br>organism = Mus musculus<br>note = Antibody 22H10A VL light chain variable region |

SEQUENCE: 150
cagactgtgg tgactcagga gccctcactg actgtgtccc caggagggac agtcactctc    60
acctgtgctt ccagcactgg aacagtcacc agtggttact ttccaaactg gctccagcag   120
aaacctggac aagcacccag ggcactgatt tatagtataa ataacaaaca tttctggacc   180
cctgcccggt tctcaggctc cctccttggg ggcaaagctg ccctgacact gtcaggtgtg   240
cagcctgagg acgaggctga gtattactgc tgctctacta tggtggcgc ttgggtgttc   300
ggcggaggga ccaagctgac cgtccta                                       327

| SEQ ID NO: 151 | moltype = AA  length = 446 |
|---|---|
| FEATURE | Location/Qualifiers |
| source | 1..446<br>mol_type = protein<br>organism = synthetic construct<br>note = Chimeric antibody 17P04A(mIgG2a) Heavy Chain |

SEQUENCE: 151
EVQLVESGGG LVKPGGSLRL SCAASGFTLS SFSMNWVRQA PGKGLEWVSS ISSRRTYIYY    60
ADSAKGRFTF SRDNAKNSLY LQMNSLRAED SAVYYCARGG YIGSPNAYDI WGQGTMVTVS   120

```
SASTKGPSVF PLAPCSRSTS ESTAALGCLV KDYFPEPVTV SWNSGALTSG VHTFPAVLQS    180
SGLYSLSSVV TVPSSNFGTQ TYTCNVDHKP SNTKVDKTVE RKCPPCKCPA PNLLGGPSVF    240
IFPPKIKDVL MISLSPIVTC VVVDVSEDDP DVQISWFVNN VEVHTAQTQT HREDYNSTLR    300
VVSALPIQHQ DWMSGKEFKC KVNNKDLPAP IERTISKPKG SVRAPQVYVL PPPEEEMTKK    360
QVTLTCMVTD FMPEDIYVEW TNNGKTELNY KNTEPVLDSD GSYFMYSKLR VEKKNWVERN    420
SYSCSVVHEG LHNHHTTKSF SRTPGK                                        446

SEQ ID NO: 152          moltype = AA  length = 215
FEATURE                 Location/Qualifiers
source                  1..215
                        mol_type = protein
                        organism = synthetic construct
                        note = Chimeric antibody 17P04A(mIgG2a) Light chain
SEQUENCE: 152
QTVVTQEPSL TVSPGGTVTL TCASSTGAVT SDYYPNWFQQ KPGQAPRALI YSASTKHSWT     60
PARFSGSLLG GKAALTLSGV QPEDEADYYC LLYYGGAWVF GGGTKLTVLG QPKAAPSVTL    120
FPPSSEELQA NKATLVCLIS DFYPGAVTVA WKADSSPVKA GVETTTPSKQ SNNKYAASSY    180
LSLTPEQWKS HRSYSCQVTH EGSTVEKTVA PTECS                               215

SEQ ID NO: 153          moltype = AA  length = 451
FEATURE                 Location/Qualifiers
source                  1..451
                        mol_type = protein
                        organism = synthetic construct
                        note = Fully human antibody 17P04A(IgG1) Heavy Chain
SEQUENCE: 153
EVQLVESGGG LVKPGGSLRL SCAASGFTLS SFSMNWVRQA PGKGLEWVSS ISSRRTYIYY     60
ADSAKGRFTF SRDNAKNSLY LQMNSLRAED SAVYYCARGG YIGSPNAYDI WGQGTMVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPELLG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 154          moltype = AA  length = 215
FEATURE                 Location/Qualifiers
source                  1..215
                        mol_type = protein
                        organism = synthetic construct
                        note = Fully human antibody 17P04A(IgG1) Light chain
SEQUENCE: 154
QTVVTQEPSL TVSPGGTVTL TCASSTGAVT SDYYPNWFQQ KPGQAPRALI YSASTKHSWT     60
PARFSGSLLG GKAALTLSGV QPEDEADYYC LLYYGGAWVF GGGTKLTVLG QPKAAPSVTL    120
FPPSSEELQA NKATLVCLIS DFYPGAVTVA WKADSSPVKA GVETTTPSKQ SNNKYAASSY    180
LSLTPEQWKS HRSYSCQVTH EGSTVEKTVA PTECS                               215

SEQ ID NO: 155          moltype = AA  length = 446
FEATURE                 Location/Qualifiers
source                  1..446
                        mol_type = protein
                        organism = synthetic construct
                        note = Chimeric antibody 18P01A(mIgG2a)  Heavy Chain
SEQUENCE: 155
EVQLVESGGG LVQPGGSLKL SCAVSGFTFS GSAMHWVRQA SGKGLEWVGR IRSKANSYAT     60
AYAASVKGRF TISRDDSKNT AFLQMNSLKT EDTAVYYCTS HAPNFDAFDI WGQGTMVTVS    120
SASTKGPSVF PLAPCSRSTS ESTAALGCLV KDYFPEPVTV SWNSGALTSG VHTFPAVLQS    180
SGLYSLSSVV TVPSSNFGTQ TYTCNVDHKP SNTKVDKTVE RKCPPCKCPA PNLLGGPSVF    240
IFPPKIKDVL MISLSPIVTC VVVDVSEDDP DVQISWFVNN VEVHTAQTQT HREDYNSTLR    300
VVSALPIQHQ DWMSGKEFKC KVNNKDLPAP IERTISKPKG SVRAPQVYVL PPPEEEMTKK    360
QVTLTCMVTD FMPEDIYVEW TNNGKTELNY KNTEPVLDSD GSYFMYSKLR VEKKNWVERN    420
SYSCSVVHEG LHNHHTTKSF SRTPGK                                        446

SEQ ID NO: 156          moltype = AA  length = 216
FEATURE                 Location/Qualifiers
source                  1..216
                        mol_type = protein
                        organism = synthetic construct
                        note = Chimeric antibody 18P01A(mIgG2a) Light chain
SEQUENCE: 156
QSVLTQPPSV SAAPGQKVTI SCSGSSSNIG NHYVSWYQQL PGTAPKFFIY DNSKRPSGIP     60
DRFSGSKSGT SATLGITGLQ TGDEADYYCG TWDSSLSTYV FGTGTKVTVL GQPKAAPSVT    120
LPPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 157          moltype = AA  length = 451
FEATURE                 Location/Qualifiers
source                  1..451
                        mol_type = protein
```

```
                        organism = synthetic construct
                        note = Fully human antibody 18P01A(IgG1) Heavy Chain
SEQUENCE: 157
EVQLVESGGG LVQPGGSLKL SCAVSGFTFS GSAMHWVRQA SGKGLEWVGR IRSKANSYAT    60
AYAASVKGRF TISRDDSKNT AFLQMNSLKT EDTAVYYCTS HAPNFDAFDI WGQGTMVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 158          moltype = AA  length = 216
FEATURE                 Location/Qualifiers
source                  1..216
                        mol_type = protein
                        organism = synthetic construct
                        note = Fully human antibody 18P01A(IgG1) Light chain
SEQUENCE: 158
QSVLTQPPSV SAAPGQKVTI SCSGSSSNIG NHYVSWYQQL PGTAPKFFIY DNSKRPSGIP    60
DRFSGSKSGT SATLGITGLQ TGDEADYYCG TWDSSLSTYV FGTGTKVTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 159          moltype = AA  length = 446
FEATURE                 Location/Qualifiers
source                  1..446
                        mol_type = protein
                        organism = synthetic construct
                        note = Chimeric antibody 20007A(mIgG2a)  Heavy Chain
SEQUENCE: 159
EVQLVESGGG LVQPGGSLKL SCAVSGFTFS GSAIHWVRQA SGKGLEWVGR IRSKVNSYAT    60
VYAASVKGRF TISRDDSKNT AFLQMNSLKT EDTAVYYCTS HAPIFDAFDI WGQGTMVTVS   120
SASTKGPSVF PLAPCSRSTS ESTAALGCLV KDYFPEPVTV SWNSGALTSG VHTFPAVLQS   180
SGLYSLSSVV TVPSSNFGTQ TYTCNVDHKP SNTKVDKTVE RKCPPCKCPA PNLLGGPSVF   240
IFPPKIKDVL MISLSPIVTC VVVDVSEDDP DVQISWFVNN VEVHTAQTQT HREDYNSTLR   300
VVSALPIQHQ DWMSGKEFKC KVNNKDLPAP IERTISKPKG SVRAPQVYVL PPPEEEMTKK   360
QVTLTCMVTD FMPEDIYVEW TNNGKTELNY KNTEPVLDSD GSYFMYSKLR VEKKNWVERN   420
SYSCSVVHEG LHNHHTTKSF SRTPGK                                       446

SEQ ID NO: 160          moltype = AA  length = 227
FEATURE                 Location/Qualifiers
source                  1..227
                        mol_type = protein
                        organism = synthetic construct
                        note = Chimeric antibody 20007A(mIgG2a)  Light chain
SEQUENCE: 160
EVQLVESGGG LVQPGGSLKL SCAVSGFTFS GSAIHWVRQA SGKGLEWVGR IRSKVNSYAT    60
VYAASVKGRF TISRDDSKNT AFLQMNSLKT EDTAVYYCTS HAPIFDAFDI WGQGTMVTVS   120
SGQPKAAPSV TLFPPSSEEL QANKATLVCL ISDFYPGAVT VAWKADSSPV KAGVETTTPS   180
KQSNNKYAAS SYLSLTPEQW KSHRSYSCQV THEGSTVEKT VAPTECS                227

SEQ ID NO: 161          moltype = AA  length = 451
FEATURE                 Location/Qualifiers
source                  1..451
                        mol_type = protein
                        organism = synthetic construct
                        note = Fully human antibody 20007A(IgG1) Heavy Chain
SEQUENCE: 161
EVQLVESGGG LVQPGGSLKL SCAVSGFTFS GSAIHWVRQA SGKGLEWVGR IRSKVNSYAT    60
VYAASVKGRF TISRDDSKNT AFLQMNSLKT EDTAVYYCTS HAPIFDAFDI WGQGTMVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 162          moltype = AA  length = 227
FEATURE                 Location/Qualifiers
source                  1..227
                        mol_type = protein
                        organism = synthetic construct
                        note = Fully human antibody 20007A(IgG1) Light chain
SEQUENCE: 162
EVQLVESGGG LVQPGGSLKL SCAVSGFTFS GSAIHWVRQA SGKGLEWVGR IRSKVNSYAT    60
VYAASVKGRF TISRDDSKNT AFLQMNSLKT EDTAVYYCTS HAPIFDAFDI WGQGTMVTVS   120
SGQPKAAPSV TLFPPSSEEL QANKATLVCL ISDFYPGAVT VAWKADSSPV KAGVETTTPS   180
KQSNNKYAAS SYLSLTPEQW KSHRSYSCQV THEGSTVEKT VAPTECS                227
```

```
SEQ ID NO: 163          moltype = AA  length = 442
FEATURE                 Location/Qualifiers
source                  1..442
                        mol_type = protein
                        organism = synthetic construct
                        note = Chimeric antibody 22D04A(mIgG2a)  Heavy Chain
SEQUENCE: 163
EVQLVESGGG LVKPGGSLRL SCAASGFTFS NAWMSWVRQA PGKGLEWVGR IKSKTDGGTR     60
DYAAPVKGRF TISRDDSKNT LYLQMNSLKT EDTAVYYCTT GYGEGYWGQG TLVTVSSAST    120
KGPSVFPLAP CSRSTSESTA ALGCLVKDYF PEPVTVSWNS GALTSGVHTF PAVLQSSGLY    180
SLSSVVTVPS SNFGTQTYTC NVDHKPSNTK VDKTVERKCP PCKCPAPNLL GGPSVFIFPP    240
KIKDVLMISL SPIVTCVVVD VSEDDPDVQI SWFVNNVEVH TAQTQTHRED YNSTLRVVSA    300
LPIQHQDWMS GKEFKCKVNN KDLPAPIERT ISKPKGSVRA PQVYVLPPPE EEMTKKQVTL    360
TCMVTDFMPE DIYVEWTNNG KTELNYKNTE PVLDSDGSYF MYSKLRVEKK NWVERNSYSC    420
SVVHEGLHNH HTTKSFSRTP GK                                             442

SEQ ID NO: 164          moltype = AA  length = 216
FEATURE                 Location/Qualifiers
source                  1..216
                        mol_type = protein
                        organism = synthetic construct
                        note = Chimeric antibody 22D04A(mIgG2a)  Light chain
SEQUENCE: 164
QSVLTQPPSA SGTPGQRVTI SCSGSSSNIK SNTVNWYQQL PGTAPKLLIY RNNQRPSGVP     60
DRFSGSKSGT SASLAISGLQ SEDEADYYCA AWDDSLKGVV FGGGTDLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 165          moltype = AA  length = 447
FEATURE                 Location/Qualifiers
source                  1..447
                        mol_type = protein
                        organism = synthetic construct
                        note = Fully human antibody 22D04A(IgG1) Heavy Chain
SEQUENCE: 165
EVQLVESGGG LVKPGGSLRL SCAASGFTFS NAWMSWVRQA PGKGLEWVGR IKSKTDGGTR     60
DYAAPVKGRF TISRDDSKNT LYLQMNSLKT EDTAVYYCTT GYGEGYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                        447

SEQ ID NO: 166          moltype = AA  length = 216
FEATURE                 Location/Qualifiers
source                  1..216
                        mol_type = protein
                        organism = synthetic construct
                        note = Fully human antibody 22D04A(IgG1) Light chain
SEQUENCE: 166
QSVLTQPPSA SGTPGQRVTI SCSGSSSNIK SNTVNWYQQL PGTAPKLLIY RNNQRPSGVP     60
DRFSGSKSGT SASLAISGLQ SEDEADYYCA AWDDSLKGVV FGGGTDLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 167          moltype = AA  length = 442
FEATURE                 Location/Qualifiers
source                  1..442
                        mol_type = protein
                        organism = synthetic construct
                        note = Chimeric antibody 06E17A(mIgG2a)  Heavy Chain
SEQUENCE: 167
EVQLVESGGG LVKPGGSLRL SCAASGFSFS NAWMSWVRQA PGKGLEWVGR IKSKTDGGTI     60
DYAAPVKGRF TISRDDSKNT LYLQMNSLKT EDTAVYYCTT GYGEGYWGQG TLVTVSSAST    120
KGPSVFPLAP CSRSTSESTA ALGCLVKDYF PEPVTVSWNS GALTSGVHTF PAVLQSSGLY    180
SLSSVVTVPS SNFGTQTYTC NVDHKPSNTK VDKTVERKCP PCKCPAPNLL GGPSVFIFPP    240
KIKDVLMISL SPIVTCVVVD VSEDDPDVQI SWFVNNVEVH TAQTQTHRED YNSTLRVVSA    300
LPIQHQDWMS GKEFKCKVNN KDLPAPIERT ISKPKGSVRA PQVYVLPPPE EEMTKKQVTL    360
TCMVTDFMPE DIYVEWTNNG KTELNYKNTE PVLDSDGSYF MYSKLRVEKK NWVERNSYSC    420
SVVHEGLHNH HTTKSFSRTP GK                                             442

SEQ ID NO: 168          moltype = AA  length = 216
FEATURE                 Location/Qualifiers
source                  1..216
                        mol_type = protein
                        organism = synthetic construct
                        note = Chimeric antibody 06E17A(mIgG2a)  Light chain
```

```
SEQUENCE: 168
QSVLTQPPSA SGTPGQRVTI SCSGSSSNIK SNTVNWYQQL PGTAPKLLIY RNNQRPSGVP    60
DRFSGSKSGT SASLAISGLQ SEDEADYYCA AWDDSLKGVV FGGGTDLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 169          moltype = AA  length = 447
FEATURE                 Location/Qualifiers
source                  1..447
                        mol_type = protein
                        organism = synthetic construct
                        note = Fully human antibody 06E17A(IgG1) Heavy Chain
SEQUENCE: 169
EVQLVESGGG LVKPGGSLRL SCAASGFSFS NAWMSWVRQA PGKGLEWVGR IKSKTDGGTI    60
DYAAPVKGRF TISRDDSKNT LYLQMNSLKT EDTAVYYCTT GYGEGYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 170          moltype = AA  length = 216
FEATURE                 Location/Qualifiers
source                  1..216
                        mol_type = protein
                        organism = synthetic construct
                        note = Fully human antibody 06E17A(IgG1) Light chain
SEQUENCE: 170
QSVLTQPPSA SGTPGQRVTI SCSGSSSNIK SNTVNWYQQL PGTAPKLLIY RNNQRPSGVP    60
DRFSGSKSGT SASLAISGLQ SEDEADYYCA AWDDSLKGVV FGGGTDLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216
```

ANTI-AMYLOID BETA PROTOFIBRIL/OLIGOMER ANTIBODIES AND USES THEREOF

RELATED APPLICATIONS

This application claims benefit of priority to U.S. Provisional Application No. 63/440,345 entitled "ANTI-AMYLOID β OLIGOMER ANTIBODIES AND USES THEREOF" filed Jan. 20, 2023, the entire contents of which is hereby incorporated by reference in its entirety.

SEQUENCE LISTING

The instant application contains a Sequence Listing which has been submitted electronically in XML file format and is hereby incorporated by reference in its entirety. Said XML copy, created on Jan. 17, 2024, is named 1121-103US_SL.xml and is 187,256 bytes in size.

FIELD OF THE INVENTION

The present disclosure relates to antibodies and antibody fragments that preferentially bind soluble amyloid β (Aβ) protofibril/oligomer, and the use of anti-Aβ protofibril/oligomer antibodies and antibody fragments in therapy, prophylaxis, diagnosis, screening, and monitoring of conditions associated with Aβ protein aggregation, in particular Alzheimer's disease (AD).

BACKGROUND

Neurodegenerative conditions associated with amyloid β (Aβ) protein aggregation and deposition include Alzheimer's disease (AD) as a common type of neurodegenerative disease. AD patients eventually lose their ability to carry out daily activities due to memory loss, changes in mood/behavior and other disabilities. Over 6 million Americans live with AD in the US, and this number is projected to reach 14 million by 2060. Globally there are over 55 million people with dementia, and AD may contribute to 60-70% of the cases. In 2019, the global economic burden of AD and related dementias was an estimated $2.8 trillion. This number is projected to increase to $16.9 trillion by 2050. There are 7 FDA approved drugs for AD but none of them shows disease-changing benefit.

AD is categorized into familial AD (fAD) and late onset AD (LOAD). Mutations in APP and PSEN1 are reported to be the cause of fAD. Both genes are responsible for the production of Aβ peptides, which are released from amyloid-beta precursor protein (APP) by proteolytic cleavage involving presenilin 1 encoded by the PSEN1 gene. The cause of LOAD is unclear. Amyloid plaques and tau tangles are the most prominent pathological features of AD brain. Amyloid plaques are the aggregated deposits of Aβ and are generally formed before the appearance of tau tangles. The disease onset of LOAD is highly correlated to the appearance of amyloid deposition, and the severity or stage of the disease correlates with the level of Tau tangles. Therefore, the main efforts in AD therapeutic development have been focused on targeting Aβ deposits and Tau tangles. Aβ may be a better therapeutic target than Tau for AD because (1) Aβ exists in the extracellular space and may be more accessible to biologics than Tau tangles, and (2) Aβ pathology is upstream of Tau pathology.

Aβ peptides exist in different forms including monomer, aggregated forms including soluble protofibril/oligomer, and insoluble plaque. The soluble protofibril/oligomer form is considered to be toxic to neurons and the insoluble plaque form, resulting from deposition of aggregated Aβ fibrils, is considered to be inert. Aβ has been the main therapeutic target for AD drug discovery over the past 2 decades. Both the monomeric and aggregated forms of Aβ have been targeted. So far, monoclonal antibodies targeting the Aβ monomer have not been able to clear amyloid plaques or provide cognitive benefit. A total of five (5) mAbs (Aducanumab, Crenezumab, Lecanemab, Donanemab and Gantenerumab) targeting extracellular aggregated Aβ have been tested in phase 2 or 3 clinical trials. All but one (Crenezumab) of these antibodies were effective in clearing amyloid plaques in human patients in a dose-dependent manner (Crenezumab was of IgG4 isotype which may not have a strong effector function). Aducanumab and Lecanemab reportedly slowed cognitive decline in the Phase 3 trials. Donanemab reportedly slowed cognitive decline in the Phase 2 trials. These data confirmed that monoclonal antibodies can reach their targets in the brain when used at high doses, and that aggregated Aβ may be a reasonable target for AD. Lecanemab, which preferentially binds Aβ protofibril/oligomer, has a lower incidence rate of edema than Aducanumab and Gantenerumab which preferentially bind Aβ plaque.

SUMMARY

The present disclosure provides anti-Aβ protofibril/oligomer antibodies and antibody fragments that preferentially bind Aβ protofibril/oligomer, amino acid sequences of variable regions of anti-Aβ protofibril/oligomer antibodies and antibody fragments, nucleotide sequences encoding variable regions of anti-Aβ protofibril/oligomer antibodies and antibody fragments, and methods of identifying, making, and using anti-Aβ protofibril/oligomer antibodies and antibody fragments. Anti-Aβ protofibril/oligomer antibodies and antibody fragments as provided herein have a fully human variable region with fully human heavy chain variable region (VH) sequence and fully human light chain variable region (VL) sequence. The present disclosure further provides fully human anti-Aβ protofibril/oligomer antibodies and antibody fragments that preferentially bind Aβ protofibril/oligomer, with fully human heavy chain variable region and fully human light chain variable region sequence.

The present disclosure provides anti-Aβ protofibril/oligomer antibodies and antibody fragments thereof that preferentially bind soluble Aβ protofibril/oligomer, wherein the anti-Aβ protofibril/oligomer antibodies and antibody fragments can trigger antibody-dependent cell-mediated phagocytosis (ADCP) in cells including microglial cells exposed to the anti-Aβ protofibril/oligomer antibodies and antibody fragments bound to Aβ protofibril/oligomer. Anti-Aβ protofibril/oligomer antibodies and antibody fragments thereof are provided that can penetrate brain tissue after administration to a mammalian subject. Anti-Aβ protofibril/oligomer antibodies and antibody fragments thereof are provided that can reduce soluble Aβ oligomer/protofibril in brain tissue after administration to a mammalian subject. Anti-Aβ protofibril/oligomer antibodies and antibody fragments thereof are provided that can reduce insoluble Aβ fibril/plaque including both condensed plaque and diffuse plaque, in brain tissue after administration to a mammalian subject. The anti-Aβ protofibril/oligomer antibodies and antibody fragments having a fully human variable region as provided herein have a lower risk of adverse reactions or unwanted side effects triggered by immunogenicity when administered to a mammalian subject, in particular to a human subject.

The present disclosure provides anti-Aβ protofibril/oligomer antibodies and antibody fragments for use in methods of therapy, prophylaxis, prevention, diagnosis, screening, and monitoring of conditions associated with Aβ protein aggregation including, but not limited to Alzheimer's disease (AD).

The present disclosure provides anti-Aβ protofibril/oligomer antibodies and antibody fragments that include an amino acid sequence that is at least 85%, 90%, 92%, 95%, 97%, 98%, 99% or 100% identical to one of the following: SEQ ID NO: 1; SEQ ID NO: 2; SEQ ID NO: 3; SEQ ID NO: 4; SEQ ID NO: 6; SEQ ID NO: 7; SEQ ID NO: 9; SEQ ID NO: 11; SEQ ID NO: 12; SEQ ID NO: 13; SEQ ID NO: 14; SEQ ID NO: 16; SEQ ID NO: 17; SEQ ID NO: 19; SEQ ID NO: 21; SEQ ID NO: 22; SEQ ID NO: 23; SEQ ID NO: 24; SEQ ID NO: 26; SEQ ID NO: 27; SEQ ID NO: 29; SEQ ID NO: 31; SEQ ID NO: 32; SEQ ID NO: 33; SEQ ID NO: 34; SEQ ID NO: 36; SEQ ID NO: 37; SEQ ID NO: 39; SEQ ID NO: 41; SEQ ID NO: 42; SEQ ID NO: 43; SEQ ID NO: 44; SEQ ID NO: 46; SEQ ID NO: 47; SEQ ID NO: 49; SEQ ID NO: 51; SEQ ID NO: 52; SEQ ID NO: 53; SEQ ID NO: 54; SEQ ID NO: 56; SEQ ID NO: 57; SEQ ID NO: 59; SEQ ID NO: 61; SEQ ID NO: 62; SEQ ID NO: 63; SEQ ID NO: 64; SEQ ID NO: 66; SEQ ID NO: 67; SEQ ID NO: 69; SEQ ID NO: 71; SEQ ID NO: 72; SEQ ID NO: 73; SEQ ID NO: 74; SEQ ID NO: 76; SEQ ID NO: 77; SEQ ID NO: 79; SEQ ID NO: 81; SEQ ID NO: 82; SEQ ID NO: 83; SEQ ID NO: 84; SEQ ID NO: 86; SEQ ID NO: 87; SEQ ID NO: 89; SEQ ID NO: 91; SEQ ID NO: 92; SEQ ID NO: 93; SEQ ID NO: 94; SEQ ID NO: 96; SEQ ID NO: 97; SEQ ID NO: 99; SEQ ID NO: 101; SEQ ID NO: 102; SEQ ID NO: 103; SEQ ID NO: 104; SEQ ID NO: 106; SEQ ID NO: 107; SEQ ID NO: 109; SEQ ID NO: 111; SEQ ID NO: 112; SEQ ID NO: 113; SEQ ID NO: 114; SEQ ID NO: 116; SEQ ID NO: 117; SEQ ID NO: 119; SEQ ID NO: 121; SEQ ID NO: 122; SEQ ID NO: 123; SEQ ID NO: 124; SEQ ID NO: 126; SEQ ID NO: 127; SEQ ID NO: 129; SEQ ID NO: 131; SEQ ID NO: 132; SEQ ID NO: 133; SEQ ID NO: 134; SEQ ID NO: 136; SEQ ID NO: 137; SEQ ID NO: 139; SEQ ID NO: 141; SEQ ID NO: 142; SEQ ID NO: 143; SEQ ID NO: 144; SEQ ID NO: 146; SEQ ID NO: 147; and SEQ ID NO: 149.

The present disclosure provides anti-Aβ protofibril/oligomer antibodies and antibody fragments identified as follows: antibodies and antibody fragments that include the 06E17A variable region comprising a fully human heavy chain variable region (VH) having the amino acid sequence of SEQ ID NO: 1 and a fully human light chain variable region (VL) having the amino acid sequence of SEQ ID NO: 6; antibodies and antibody fragments that include the 15M13A variable region comprising a fully human VH having the amino acid sequence of SEQ ID NO: 11, and a fully human VL having the amino acid sequence of SEQ ID NO: 16; antibodies and antibody fragments that include the 17D08A variable region comprising a fully human VH having the amino acid sequence of SEQ ID NO: 21 and a fully human VL having the amino acid sequence of SEQ ID NO: 26; antibodies and antibody fragments that include the 17H05A variable region comprising a fully human VH having the amino acid sequence of SEQ ID NO: 31 and a fully human VL having the amino acid sequence of SEQ ID NO: 36; antibodies and antibody fragments that include the 17P04A variable region comprising a fully human VH having the amino acid sequence of SEQ ID NO: 41 and a fully human VL having the amino acid sequence of SEQ ID NO: 46; antibodies and antibody fragments that include the 18F06A variable region comprising a fully human VH having the amino acid sequence of SEQ ID NO: 51 and an fully human VL having the amino acid sequence of SEQ ID NO: 56; antibodies and antibody fragments that include the 18P01A variable region comprising a fully human VH having the amino acid sequence of SEQ ID NO: 61 and a fully human VL having the amino acid sequence of SEQ ID NO: 66; antibodies and antibody fragments that include the 20O07A variable region comprising a fully human VH having the amino acid sequence of SEQ ID NO: 71 and a fully human VL having the amino acid sequence of SEQ ID NO: 76; antibodies and antibody fragments that include the 20O11A variable region comprising a fully human VH having the amino acid sequence of SEQ ID NO: 81 and a fully human VL having the amino acid sequence of SEQ ID NO: 86; antibodies and antibody fragments that include the 21F12A variable region comprising a fully human VH having the amino acid sequence of SEQ ID NO: 91 and a fully human VL having the amino acid sequence of SEQ ID NO: 96; antibodies and antibody fragments that include the 21G10A variable region comprising a fully human VH having the amino acid sequence of SEQ ID NO: 101 and a fully human VL having the amino acid sequence of SEQ ID NO: 106; antibodies and antibody fragments that include the 21K12A variable region comprising a fully human VH having the amino acid sequence of SEQ ID NO: 111 and a fully human VL having the amino acid sequence of SEQ ID NO: 116; antibodies and antibody fragments that include the 21P22A variable region comprising a fully human VH having the amino acid sequence of SEQ ID NO: 121 and a fully human VL having the amino acid sequence of SEQ ID NO: 126; antibodies and antibody fragments that include the 22D04A comprising a fully human VH having the amino acid sequence of SEQ ID NO: 131 and a fully human VL having the amino acid sequence of SEQ ID NO: 136; antibodies and antibody fragments that include the 22H10A variable region comprising a fully human VH having the amino acid sequence of SEQ ID NO: 141 and a fully human VL having the amino acid sequence of SEQ ID NO: 146; and anti-Aβ oligomer antibodies and antibody fragments having at least 85% amino acid sequence identity to the VH and/or VL amino acid sequences recited above.

The present disclosure provides anti-Aβ protofibril/oligomer antibodies and antibody fragments as follows: (a) an antibody or antibody fragment comprising a heavy chain variable region (VH) comprising an HC CDR 1 having the amino acid sequence GFTLSSFS (SEQ ID NO: 42), an HC CDR2 having the amino acid sequence ISSRRTYI (SEQ ID NO: 43), and an HC CDR3 having the amino acid sequence ARGGYIGSPNAYDI (SEQ ID NO: 44), and a light chain variable region (VL) comprising an LC CDR1 having the amino acid sequence TGAVTSDYY (SEQ ID NO: 47), an LC CDR2 having the amino acid sequence SAS, and an LC CDR3 having the amino acid sequence LLYYGGAWV (SEQ ID NO: 49); (b) an antibody or antibody fragment comprising a VH comprising an HC CDR 1 having the amino acid sequence GFTFSGSA (SEQ ID NO: 62), an HC CDR2 having the amino acid sequence IRSKANSYAT (SEQ ID NO: 63), and an HC CDR3 having the amino acid sequence TSHAPNFDAFDI (SEQ ID NO: 64), and a VL comprising an LC CDR1 having the amino acid sequence SSNIGNHY (SEQ ID NO: 67), an LC CDR2 having the amino acid sequence DNS, and an LC CDR3 having the amino acid sequence GTWDSSLSTYV (SEQ ID NO: 69); (c) an antibody or antibody fragment comprising a VH comprising an HC CDR 1 having the amino acid sequence GFTFSGSA (SEQ ID NO: 72), an HC CDR2 having the amino acid sequence IRSKVNSYAT (SEQ ID NO: 73), and an HC CDR3 having the amino acid sequence TSHAPIFDAFDI (SEQ ID NO: 74), and a VL comprising an LC CDR1 having the amino acid sequence SSNIGNHY (SEQ ID NO: 77), an LC CDR2 having the amino acid sequence DNS, and an LC CDR3 having the amino acid sequence GTWDSSLSTYF (SEQ ID NO: 79); (d) an antibody or antibody fragment comprising a VH comprising an HC CDR 1 having the amino acid sequence GFTFSNAW (SEQ ID NO: 132), an HC CDR2 having the amino acid sequence IKSKTDGGTR (SEQ ID NO: 133), and an HC CDR3 having the amino acid sequence TTGYGEGY (SEQ ID NO: 134), and a VL comprising an LC CDR1 having the amino acid sequence SSNIKSNT (SEQ ID NO: 137), an LC CDR2 having the amino acid sequence RNN, and an LC CDR3 having the amino acid sequence AAWDDSLKGVV (SEQ ID NO: 139); and (e) an antibody or antibody fragment comprising a VH comprising an HC CDR 1 having the amino acid sequence GFSFSNAW (SEQ ID NO: 2), an HC CDR2 having the amino acid sequence IKSKTDGGTI (SEQ ID NO: 3), and an HC CDR3 having the amino acid sequence TTGYGEGY (SEQ ID NO: 4), and a VL comprising an LC CDR1 having the amino acid sequence SSNIKSNT (SEQ ID NO: 7), an LC CDR2 having the amino acid sequence RNN, and an LC CDR3 having the amino acid sequence AAWDDSLKGVV (SEQ ID NO: 9).

The present disclosure provides anti-Aβ protofibril/oligomer antibodies and antibody fragments with constant region sequence that includes fragment crystallizable region (Fc) sequence sufficient to enable Fc-mediated effector functions such as antibody dependent cellular phagocytosis (ADCP). The present disclosure provides anti-Aβ protofibril/oligomer antibodies and antibody fragments with Fc sequence from the IgG class of immunoglobulin molecules. The present disclosure provides anti-Aβ protofibril/oligomer antibodies and antibody fragments with a constant region Fc that may be mouse IgG1 Fc, human IgG1 Fc, mouse IgG2a Fc, and mouse IgG2b Fc.

The present disclosure provides pharmaceutical compositions containing at least one anti-Aβ protofibril/oligomer antibody or antibody fragment as disclosed herein, and a pharmaceutically acceptable carrier or excipient.

The present disclosure provides a method of reducing the amount of soluble Aβ protofibril/oligomer in a subject by administering to the subject a therapeutically effective amount of at least one anti-Aβ protofibril/oligomer antibody or antibody fragment disclosed herein. A method of reducing the amount of soluble Aβ protofibril/oligomer in a subject is provided wherein administering to the subject a therapeutically effective amount of at least one anti-Aβ protofibril/oligomer antibody or antibody fragment disclosed herein triggers antibody-dependent cell-mediated phagocytosis (ADCP) of complexes comprising the anti-Aβ protofibril/oligomer antibody or antibody fragment bound to Aβ protofibril/oligomer. ADCP mediated by responsive effector cells may occur in any tissue, including in at least one of blood, lymph, cerebrospinal fluid (CSF), nervous tissue, and brain.

The present disclosure provides a method of reducing the amount of soluble Aβ protofibril/oligomer in the brain of a mammalian subject by administering to the subject a therapeutically effective amount of at least one anti-Aβ protofibril/oligomer antibody or antibody fragment disclosed herein.

The present disclosure provides a method of reducing the amount of Aβ plaque in a subject, comprising administering to the subject a therapeutically effective amount of the anti-Aβ protofibril/oligomer antibody or antibody fragment disclosed herein. The present disclosure provides a method of reducing levels of Aβ plaque in the brain of the mammalian subject by administering to the subject a therapeutically effective amount of at least one anti-Aβ protofibril/oligomer antibody or antibody fragment disclosed herein. The present disclosure provides a method of reducing levels of condensed Aβ plaque in the brain of the mammalian subject by administering to the subject a therapeutically effective amount of at least one anti-Aβ protofibril/oligomer antibody or antibody fragment disclosed herein. The present disclosure provides a method of reducing levels of diffuse Aβ plaque in the brain of the mammalian subject by administering to the subject a therapeutically effective amount of at least one anti-Aβ protofibril/oligomer antibody or antibody fragment disclosed herein. Accordingly, the present disclosure provides a method of reducing the plaque burden in a subject, comprising administering to the subject a therapeutically effective amount of the anti-Aβ protofibril/oligomer antibody or antibody fragment disclosed herein. A method of reducing the amount of Aβ plaque in a subject is provided wherein administering to the subject a therapeutically effective amount of at least one anti-Aβ protofibril/oligomer antibody or antibody fragment disclosed herein is expected to trigger ADCP of complexes comprising the anti-Aβ protofibril/oligomer antibody or antibody fragment bound to Aβ protofibril/oligomer, with results that include reduction in the amount of Aβ plaque in the subject.

The present disclosure provides a method of treating at least one condition associated with Aβ protein aggregation by administering an effective amount of at least one anti-Aβ oligomer antibody or antibody fragment as disclosed herein, to a subject in need thereof. A method of treating at least one condition associated with Aβ protein aggregation by administering an effective amount of at least one anti-Aβ protofibril/oligomer antibody or antibody fragment thereof is provided, wherein the at least one condition associated with Aβ protein aggregation is Alzheimer's disease (AD).

The present disclosure provides a method of treating at least one condition associated with Aβ protein aggregation, wherein administering at least one anti-Aβ protofibril/oligomer antibody or antibody fragment disclosed herein to a subject in need thereof triggers antibody-dependent cell-mediated phagocytosis (ADCP) of complexes comprising the anti-Aβ protofibril/oligomer antibody or antibody fragment bound to Aβ protofibril/oligomer.

The present disclosure provides a method of preventing the onset or the further development of at least one condition associated with Aβ protein aggregation, by administering an effective amount of at least one anti-Aβ protofibril/oligomer antibody or antibody fragment as disclosed herein, to a subject in need thereof. A method of preventing the onset or the further development of at least one condition associated with Aβ protein aggregation is provided wherein administering the anti-Aβ protofibril/oligomer antibody or antibody fragment to a subject in need thereof triggers antibody-dependent cell-mediated phagocytosis (ADCP) of complexes comprising the anti-Aβ protofibril/oligomer antibody or antibody fragment bound to Aβ protofibril/oligomer, thereby substantially preventing Aβ protein aggregation in the subject and ultimately reducing plaque load. A method of treating, preventing the onset of, or preventing the further development of at least one condition associated with Aβ protein aggregation by administering an effective amount of at least one anti-Aβ protofibril/oligomer antibody or antibody fragment is provided, wherein the at least one condition associated with Aβ protein aggregation is Alzheimer's disease (AD).

The present disclosure provides a method of diagnosing at least one condition associated with Aβ protein aggregation in a subject by using at least one anti-Aβ protofibril/oligomer antibody or antibody fragment as disclosed herein, to detect Aβ protofibril/oligomer, in a sample from the subject, where the sample may be a soluble fraction or a fixed tissue sample.

The present disclosure provides a method of screening for at least one condition associated with Aβ protein aggregation in a subject by using the anti-Aβ protofibril/oligomer antibody or antibody fragment as disclosed herein to detect Aβ protofibril/oligomer in a sample from the subject.

The present disclosure provides a method of monitoring at least one condition associated with Aβ protein aggregation in a subject, comprising using at least one anti-Aβ protofibril/oligomer antibody or antibody fragment as disclosed herein to detect Aβ protofibril/oligomer in a sample from the subject.

The present disclosure provides an in vivo, ex vivo, or in vitro method for detecting soluble Aβ protofibril/oligomer in a sample by contacting the sample with at least one anti-Aβ protofibril/oligomer antibody or antibody fragment as disclosed herein, and detecting binding of the anti-Aβ protofibril/oligomer antibody or antibody fragment to Aβ protofibril/oligomer to indicate the presence of soluble Aβ protofibril/oligomer in the sample. The present disclosure provides an in vivo, ex vivo, or in vitro method for detecting soluble Aβ protofibril/oligomer in a sample by contacting the sample with at least one anti-Aβ protofibril/oligomer antibody or antibody fragment as disclosed where the wherein the Aβ peptide binding polypeptide is part of a fusion protein or conjugate, and detecting binding of the anti-Aβ protofibril/oligomer antibody or antibody fragment to Aβ protofibril/oligomer to indicate the presence of soluble Aβ protofibril/oligomer in the sample.

The present disclosure provides an in vivo, ex vivo, or in vitro method of reducing the amount of soluble Aβ protofibril/oligomer in a sample suspected to contain Aβ protofibril/oligomer, comprising contacting the sample with an effective amount of at least one anti-Aβ protofibril/oligomer antibody or antibody fragment as disclosed herein to form a mixture, and then recovering the anti-Aβ protofibril/oligomer antibody or antibody fragment from the mixture, thereby removing Aβ protofibril/oligomer bound to the anti-Aβ protofibril/oligomer antibody or antibody fragment from the sample.

The present disclosure provides a method for producing an anti-Aβ protofibril/oligomer antibody or antibody fragment that preferentially binds soluble Aβ protofibril/oligomer and has a lower risk of immunogenicity, i.e., a lower risk of adverse reactions or other unwanted side effects when administered to a subject, especially when administered to a human. The method as presently disclosed includes selecting a mammal that can generate antibodies with fully human variable regions, immunizing the mammal by introducing a preparation of purified Aβ protofibril into the mammal, collecting enriched B cells from spleen and lymph nodes of the mammal immunized with a preparation of purified Aβ protofibril, fusing the B cells with a myeloma fusion partner to create hybridomas, recovering antibodies from each of the hybridomas, conducting a primary screen of the recovered antibodies from each of the hybridomas comprising measuring binding to Aβ peptide in an ELISA-based assay, identifying and recovering any antibody with a sufficient level of detectable binding to Aβ peptide(s), conducting a confirmation screen of each recovered antibody after the primary screen comprising measuring competition of Aβ monomer and Aβ protofibril for binding to the recovered antibody using competitive ELISA, and measuring direct binding of each recovered antibody to Aβ monomer, Aβ protofibril and Aβ fibril by ELISA, and further comprising selecting each recovered antibody showing higher affinity for protofibril over monomer in competitive ELISA.

The present disclosure provides an isolated nucleic acid molecule that encodes at least a portion of an anti-Aβ protofibril/oligomer antibody or antibody fragment as disclosed herein, where the nucleotide sequence of isolated nucleic acid molecule incudes a nucleotide sequence that is at least 85%, 90%, 92%, 95%, 97%, 98%, 99% or 100% identical to one of the following: SEQ ID NO: 5, SEQ ID NO: 10, SEQ ID NO: 15, SEQ ID NO: 20, SEQ ID NO. 25, SEQ ID NO: 30, SEQ ID NO: 35, SEQ ID NO: 40, SEQ ID NO: 45, SEQ ID NO: 50, SEQ ID NO: 55, SEQ ID NO: 60, SEQ ID NO: 65, SEQ ID NO: 70, SEQ ID NO: 75, SEQ ID NO: 80, SEQ ID NO: 85, SEQ ID NO: 90, SEQ ID NO: 95, SEQ ID NO: 100, SEQ ID NO: 105, SEQ ID NO: 110, SEQ ID NO: 115, SEQ ID NO: 120, SEQ ID NO: 125, SEQ ID NO: 130, SEQ ID NO: 135, SEQ ID NO: 140, SEQ ID NO: 145, and SEQ ID NO: 150. The present disclosure provides a vector comprising an isolated nucleic acid molecule that encodes at least a portion of an anti-Aβ protofibril/oligomer antibody or antibody fragment as disclosed herein.

BRIEF DESCRIPTION OF THE FIGURES

FIG. 1 shows a superposition of the SEC results for the $A\beta_{1-42}$ monomer (dotted line) control sample, and the $A\beta_{1-42}$ protofibril & monomer mixture (solid black line), with the area % of $A\beta_{1-42}$ protofibril and $A\beta_{1-42}$ monomer peaks in each sample. Samples from the $A\beta_{1-42}$ protofibril peak were collected as purified $A\beta_{1-42}$ protofibril for immunization.

FIGS. 2A-2B show results from direct ELISA of reference antibodies rfmAb-1 and rfmAb-2 with respect to different Aβ conformations. Aβ monomers ($A\beta_{1-40}$ monomers), Aβ protofibrils ($A\beta_{1-42}$ protofibrils), or Aβ fibrils ($A\beta_{1-42}$ fibrils) were coated on an ELISA plate at 50 pmol per well. Dilutions of rfmAb-1 and rfmAb-2 were applied to the plate and the binding of antibody to Aβ in each well was detected by HRP-labeled secondary antibody and TMB substrate. FIG. 2A: as measured by direct ELISA, the EC50 of rfmAb-1 for Aβ monomer ($A\beta_{1-40}$ monomers, open circles) was 0.03 nM, the EC50 of rfmAb-1 for Aβ protofibril ($A\beta_{1-42}$ protofibrils, open squares) was 0.04 nM, and Aβ and the EC50 of rfmAb-1 for Aβ fibril ($A\beta_{1-42}$ fibrils, open triangles) was 1.1 nM. FIG. 2B: as measured by direct ELISA, the EC50 of rfmAb-2 for Aβ monomer ($A\beta_{1-40}$ monomers, open circles) was 0.05 mM, the EC50 of rfmAb-2 for Aβ protofibril ($A\beta_{1-42}$ protofibrils, open squares) was 0.05 nM, and the EC50 of rfmAb-2 for Aβ fibril ($A\beta_{1-42}$ fibrils, open triangles) was 0.08 nM.

FIGS. 3A-3B show results from competitive ELISA of reference antibodies rfmAb-1 and rfmAb-2 with respect to different Aβ conformations. Each antibody (0.12 nM for rfmAb-1 and 0.21 nM for rfmAb-2) was pre-incubated with diluents of Aβ monomer (Aβ$_{1-40}$ monomers), Aβ protofibril (Aβ$_{1-42}$ protofibrils), or Aβ fibril (Aβ$_{1-42}$ fibrils) for 1 h. The antibody-Aβ mixture was then applied to an ELISA plate coated with Aβ monomer for 10 min and binding to Aβ monomer was detected by HRP-labeled secondary antibody and TMB substrate. FIG. 3A: as calculated, the IC50 of Aβ monomer (Aβ$_{1-40}$ monomers, open circles) for rmAb-1 was 991.3 nM, the IC50 of Aβ protofibril (Aβ$_{1-42}$ protofibrils, open squares) for rmAb-1 was 1.0 nM, and the IC50 of Aβ fibril (Aβ$_{1-42}$ fibrils, open triangles) for rfmAb-1 was 128.7 nM. FIG. 3B: as calculated, the IC50 of Aβ monomer (Aβ$_{1-40}$ monomers, open circles) for rfmAb-2 was 1.5 nM, the IC50 of Aβ protofibril (Aβ$_{1-42}$ protofibrils, open squares) for rfmAb-2 was 5.4 nM, and the IC50 of Aβ fibril (Aβ$_{1-42}$ fibrils, open triangles) for rfmAb-2 was 179.5 nM.

FIG. 5A shows direct binding of antibodies to Aβ$_{1-42}$ protofibril, EC50 for 18P01A (open circle), 17P04A (open square), 20O07A (upward-pointing triangle), 22D04A (downward-pointing triangle), and 06E17A (open diamond) are 0.062 nM, 0.045 nM, 0.050 nM, 0.035 nM, and 0.052 nM, respectively. FIG. 5B shows binding of antibodies to Aβ$_{p3-42}$, where EC50 for all lead antibodies could not be measured indicating weak or no binding to Aβ$_{p3-42}$.

In FIG. 11B, results of one-way ANOVA followed by Sidak's test:  indicates $p<0.01$ for rfmAb-1 at 3, or 10 mg/kg vs. PBS vehicle (Veh); ** indicates $p<0.0001$ for 17P04A at 1, 3, or 10 mg/kg vs. PBS vehicle (Veh); #$p<0.05$ for rfmAb-1 at 3 mg/kg vs 17P04A at 3 mg/kg; ##$p<0.01$ indicates rfmAb-1 at 10 mg/kg vs 17P04A at 10 mg/kg.

In FIG. 12B, results of one-way ANOVA followed by Sidak's test: ** $p<0.01$ for rfmAb-1 at 1 mg/kg vs vehicle (Veh).

FIG. 14A, N=6-10; FIG. 14B, N=5-13. In FIG. 14A, results of one-way ANOVA followed by Sidak's test: * p<0.05 for 17P04 at 10 mg/kg vs vehicle (Veh).

FIGS. 15A-15B show Campbell-Switzer staining of brain sections of 11-month-old B6SJLF1/J (WT) mice, 11-month-old 5×FAD mice treated by weekly ip injection of PBS vehicle (Veh), 11-month-old 5×FAD mice treated with rfmAb-1 by weekly ip injection of rfmAb-1 at 1, 3, or 10 mg/kg for 4 months, and 11-month-old 5×FAD mice treated with 17P04A by weekly ip injection of 17P04A at 1, 3, or 10 mg/kg for 4 months (FIG. 15A), and calculated amounts of diffuse Aβ plaque and condensed Aβ plaque in brains (FIG. 15B). FIG. 15A, representative images of Campbell-Switzer stain on brain sections at around Bregma −1.30 mm.

FIG. 15B, calculated percentage area of condensed Aβ plaque (upper graph) and diffuse Aβ plaque (lower graph) in the brain of WT (B6SJLF1/J) and 5×FAD mice; percentage area in each brain was the average value of 4 brain sections at bregma −0.25, −1.30, −2.35, and −3.40 mm. N=10, 13, 8, 8, 10, 8, 9, 9. In FIG. 15B, results of one-way ANOVA followed by Sidak's test:  p<0.01 vs. vehicle (Veh); * p<0.001 vs vehicle (Veh); #p<0.05 rfmAb-1 vs 17P04 at the same dose; ##p<0.01 rfmAb-1 vs 17P04 at the same dose.

DETAILED DESCRIPTION

Figure 1:
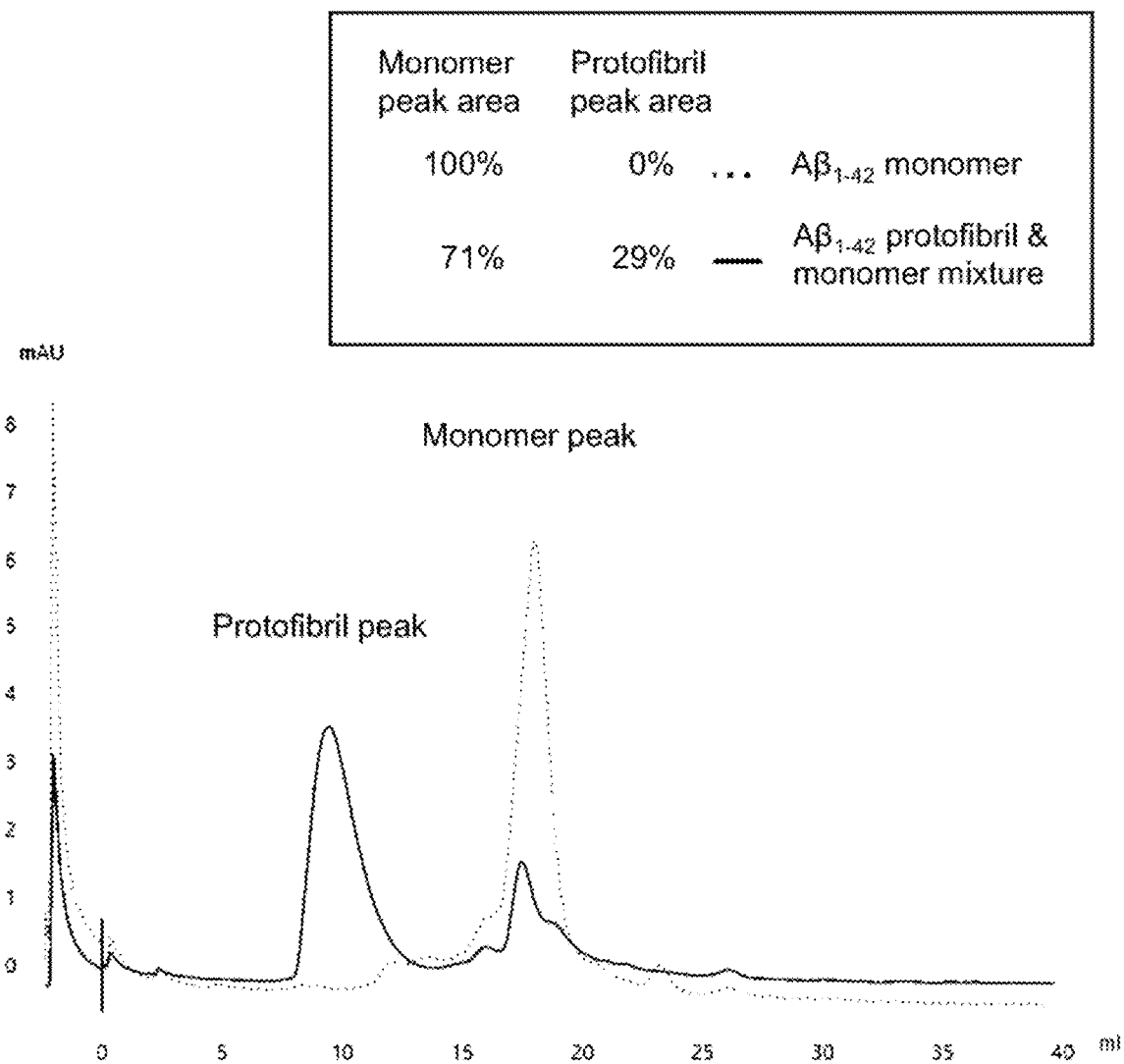
FIG. 1 shows analysis of $A\beta_{1-42}$ conformations by size exclusion chromatography (SEC), for purposes of recovering purified preparations of $A\beta_{1-42}$ protofibril. $A\beta_{1-42}$ monomer solution was incubated at 37° C. for 2 h to form an $A\beta_{1-42}$ protofibril & monomer mixture. A control solution of $A\beta_{1-42}$ monomer (dotted line) and the $A\beta_{1-42}$ protofibril & monomer mixture (solid black line) were analyzed by SEC on a SUPERDEX® 200 Increase 10/300 GL column.

The present disclosure relates to and provides novel anti-Aβ protofibril/oligomer antibodies and antibody fragments that preferentially bind soluble Aβ protofibril/oligomer and have a fully human variable region, wherein the anti-Aβ protofibril/oligomer antibodies and antibody fragments can trigger antibody-dependent cell-mediated phagocytosis (ADCP) in cells including microglial cells exposed to the anti-Aβ protofibril/oligomer antibodies and antibody fragments bound to Aβ protofibril/oligomer, and further wherein the anti-Aβ protofibril/oligomer antibodies and antibody fragments can penetrate brain tissue after administration to a mammalian subject and reduce soluble Aβ oligomer/protofibril levels and insoluble Aβ fibril/plaque in brain tissue, including both condensed plaque and diffuse plaque, measured in brain tissue after administration to the subject. Noting that both Aβ oligomer and Aβ protofibril are soluble neurotoxic Aβ aggregates formed by monomers, presumably in different structures and molecular weights, but without wishing to be bound by a specific model or mechanism of action, the present disclosure relates to and provides novel anti-Aβ protofibril/oligomer antibodies and antibody fragments that preferentially bind soluble Aβ protofibril/oligomer and provide therapeutic effects related to reducing soluble Aβ oligomer/protofibril levels in one or more tissues after administration to a subject.

Terminology/Definitions

Scientific and technical terms used in connection with the present invention shall have the meanings that are commonly understood by those of ordinary skill in the art, unless otherwise defined. Use of singular terms ("a" or "an" or "the" or other use of a term in the singular) include plural reference, and plural terms shall include the singular, unless the context clearly dictates otherwise. Thus, for example, reference to "an antibody" includes "one or more" antibodies or a "plurality" of such antibodies. All publications mentioned herein are hereby incorporated by reference in their entirety.

Generally, nomenclature and techniques of molecular biology, microbiology, cell and tissue culture, protein and nucleotide chemistry, and recombinant DNA techniques available to one of skill of the art can be employed for the antibodies, antigen-binding fragments, compositions, and methods disclosed herein. Techniques and procedures described herein are generally performed according to conventional methods well known in the art and as described in various general and more specific references, inter alia, Sambrook et al. (1989) MOLECULAR CLONING: A LABORATORY MANUAL (2nd ed., Cold Spring Harbor Laboratory Press, Cold Spring Harbor, N.Y.) and Ausubel et al. (1994) CURRENT PROTOCOLS IN MOLECULAR BIOLOGY, Volumes I-III (John Wiley & Sons, N.Y.). Enzymatic reactions and purification techniques are performed according to manufacturer's specifications or as commonly accomplished in the art or as described herein, unless otherwise specified herein. Techniques and methods for pharmaceutical preparation and formulation, and treatment of subjects, are described herein using conventional nomenclature.

"Antibody" and "antibody fragment" refer in the broadest sense to a polypeptide or combination of polypeptides that recognizes and binds to an antigen through one or more immunoglobulin variable regions, where the immunoglobulin variable regions may be naturally occurring or non-naturally occurring, e.g., as a result of engineering, chimerization, humanization, optimization, CDR-grafting, or affinity maturation. An antibody or antibody fragment as disclosed herein comprises at least sufficient complementarity determining regions (CDR), interspersed with framework regions (FR), for the antibody to recognize and bind to an antigen. An antibody or antibody fragment as disclosed herein may include additional peptides or other moieties, according to the desired function, such as sufficient constant region (also called constant domain) structure/sequence to elicit a desired reaction, e.g., ADCP in an effector cell, or regions that support labels, tags, linkers, conjugation, etc., to allow the antibody or antibody fragment to be detected, imaged, conjugated, tagged, cross-linked, immobilized, removed, etc.

A antibody or antibody fragment may be, but is not limited to, at least one of a monoclonal antibody, a recombinant monoclonal antibody, a polyclonal antibody, a humanized antibody, a chimeric antibody, a single chain antibody, a Fab fragment, a single-chain variable fragment (scFv), an aptamer, a single-domain antibody (VHH or nanobody), a recombinant antibody, a modified antibody having peptide/other moieties attached to antibody and/or additional amino acids added the N- or C-terminus, or other antigen-binding fragment or variant. The term "chimeric" antibody refers to an antibody in which a portion of the heavy chain (HC) and/or light chain (LC) is derived from a particular source or species, while the remainder of the HC and/or LC is derived from a different source or species, e.g., a target binding region (usually, the variable region) will be from one species (e.g., human, non-human primate, or mouse) and the constant region (especially the Fc) is from a different species. A chimeric antibody may be produced by a source engineered to produce antibodies with defined variable regions and defined constant regions, e.g., by a mouse engineered to express the entire human variable immunoglobulin region to produce antibodies with fully human variable regions, and constant regions that may include mouse constant region sequence, e.g., mouse Fc, and/or by cells engineered to produce antibodies with similar defined variable region/constant region formats. It is understood that the present disclosure is directed to providing antibodies with fully human variable regions, where in some embodiments antibodies may be naturally occurring chimeric antibodies produced by cells from a mouse (*Mus musculus*) engineered to produce antibodies with fully human variable regions. It is understood that in other embodiments, antibodies may be recombinant antibodies produced by cells expressing one or more constructs encoding antibodies with fully human variable regions in defined variable region/constant region formats such as fully human antibodies or chimeric antibodies, where constant region components including the Fc are from a class/subclass (isotype) selected for the particular use and target for which the antibody is intended. As used herein, the phrase "humanized antibody" refers to an antibody or antibody variant derived from a non-human antibody with a non-human variable region, typically a mouse monoclonal antibody, where CDRs from the parental non-human antibody are grafted (fused) in a framework comprising variable regions derived from a human immunoglobulin framework, in particular an acceptor human framework or a human consensus framework. Techniques and principles for designing, making, and testing humanized antibodies are known (Jones P T, Dear P H, Foote J, Neuberger M S, Winter G. Replacing the complementarity-determining regions in a human antibody with those from a mouse. *Nature*. 1986 May 29-Jun. 4; 321(6069): 522-5; Almagro J C, Fransson J. Humanization of antibodies. *Front Biosci*. 2008 Jan. 1; 13:1619-33). It is understood that changes can be made to an acceptor framework at multiple locations in order to develop a humanized antibody having improved features according to the desired use, e.g., high affinity for target, low clearance, low toxicity, etc. The constant region (constant domain) of an antibody or antibody fragment may be derived from one of five major classes of antibodies, viz., IgA, IgD, IgE, IgG, and IgM, and several of these may be further divided into subclasses (isotypes), e.g., IgG1, IgG2, IgG3, IgG4, IgA1, and IgA2, each of which is well characterized and known to confer functional specialization. Modified versions of each of these classes and isotypes are readily discernable and within the scope of the instant disclosure. While all immunoglobulin classes are within the scope of the present disclosure, the present disclosure will be directed largely to the IgG class of immunoglobulin molecules.

An anti-Aβ protofibril/oligomer antibody or antibody fragment as disclosed herein can be a whole (intact, full length) antibody, a single chain antibody, or an antibody fragment with one or two chains, and can be naturally occurring or non-naturally occurring. An antibody or antibody fragment as disclosed herein comprises at least sufficient complementarity determining regions (CDR), interspersed with framework regions (FR), for the antibody to recognize and bind to an antigen, preferably Aβ protofibril/oligomer. An anti-Aβ protofibril/oligomer antibody or antibody fragment as disclosed herein may have a partial or complete variable region portion comprising at least a sufficient amount of a fully human heavy chain variable region polypeptide (VH) and a sufficient amount of a fully human light chain variable region polypeptide (VL) that together form a structure with a binding domain that interacts with an antigen, preferably soluble Aβ protofibril/oligomer, and it is understood that the variable region of an anti-Aβ protofibril/oligomer antibody or antibody fragment disclosed herein may include two VH-VL structures. An anti-Aβ protofibril/oligomer antibody as disclosed herein may be a full length antibody, intact antibody, naturally occurring antibody, or equivalent terms which are understood to refer to a polypeptide comprising two full-length heavy chains (HCs) and two light chains (LCs) interconnected by disulfide bonds, forming a constant region and a variable region. It is understood that an anti-Aβ protofibril/oligomer antibody or antibody fragment disclosed herein, in particular an anti-Aβ protofibril/oligomer antibody fragment disclosed herein, may comprise HC polypeptides that would not necessarily be considered full-length HCs, especially in the constant region, but have sufficient structure/sequence for a desired function, e.g., sufficient constant region structure/sequence to elicit a desired reaction, in particular sufficient Fc structure/sequence to trigger ADCP in an effector cell, or sufficient constant region structure/sequence to support labels, tags, linkers, conjugation, etc., to allow the antibody or antibody fragment to be detected, imaged, tagged, conjugated, cross-linked, immobilized, removed, etc.

In an anti-Aβ protofibril/oligomer antibody or antibody fragment as disclosed herein, each of the VH and VL regions can be further subdivided into CDR regions characterized by hypervariability, interspersed with FR regions that are typically more conserved. Each VH and VL is typically composed of three CDRs and four FRs arranged from amino-terminus to carboxy-terminus in the following order: FR1, CDR1, FR2, CDR2, FR3, CDR3, FR4. The constant regions of the antibodies may mediate the binding of the immunoglobulin to host tissues or factors, including various cells of the immune system and the classical complement system, and/or may trigger functions in effector cells. Typically, an anti-Aβ protofibril/oligomer antibody or antibody fragment as disclosed herein at least heavy chain (HC)-CDR1, HC-CDR2, and HC-CDR3 and light chain (LC)-CDR1, LC-CDR2, and LC-CDR3 sequences. The VH and VL amino acid sequences of non-limiting embodiments of anti-Aβ protofibril/oligomer antibodies or antibody fragments are disclosed in Table 2 (VH) and Table 3 (VL), where the CDRs as identified using IMGT numbering (imgt.org) are indicated by underlining in each VH and VL region and provided as separate sequences. Nucleotide sequences encoding the VHs and VLs of non-limiting embodiments of anti-Aβ protofibril/oligomer antibodies or antibody fragments are disclosed in the sequence listing presently incorporated by reference. An antibody may comprise fewer CDR sequences, as long as the antibody can recognize and bind an antigen.

An anti-Aβ protofibril/oligomer antibody or antibody fragment disclosed herein may be a variant comprising at least one altered CDR or framework sequence, wherein CDR and/or framework sequences may by optimized by mutating a nucleic acid molecule encoding such framework sequence. An anti-Aβ protofibril/oligomer antibody or antibody fragment disclosed herein may have HC and LC portions derived independently from different sources. Techniques for generating variants include but are not limited to conservative amino acid substitution, computer modeling, screening candidate polypeptides alone or in combinations, and codon optimization, and it is understood that a skilled person is capable of generating antibody variants as may be needed. An anti-Aβ protofibril/oligomer antibody or antibody fragment disclosed herein may be a fragment, provided the fragment retains the ability to trigger ADCP when bound to Aβ protofibril/oligomer. Antigen binding functions of an antibody can be performed by fragments such as: a Fab fragment; a monovalent fragment consisting of the VL, VH, CL and CH1 domains; a F(ab)$_2$ fragment; a bivalent fragment comprising two Fab fragments linked by a disulfide bridge at the hinge region; an Fd fragment consisting of the VH and CH1 domains; a single-chain variable fragment (scFv) consisting of the VL and VH domains of a single arm of an antibody; a single domain antibody (dAb) fragment which consists of a VH domain; and an isolated CDR (VHH, nanobody), or an aptamer. Antigen binding portions can be incorporated into single domain antibodies, maxibodies, minibodies, nanobodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides to form monobodies (see, e.g., U.S. Pat. No. 6,703,199, which describes fibronectin polypeptide monobodies).

Terms including "conditions associated with Aβ protein aggregation" or "conditions associated with Aβ protein aggregation and deposition" or "Aβ peptide associated disorders" are understood to refer to a group of conditions, diseases, and disorders associated with Aβ plaque formation, in particular, extracellular Aβ plaque formation. Neurological conditions associated with Aβ protein aggregation and deposition include but are not limited to Alzheimer's disease (AD), mild cognitive impairment (MCI), Lewybody dementia, Down's syndrome, hereditary cerebral hemorrhage with amyloidosis, and other diseases which are based on or associated with amyloid-like proteins such as cerebral amyloid angiopathy, primary and secondary systemic amyloidosis, familial amyloid polyneuropathy 1, progressive supranuclear palsy, multiple sclerosis, Creutzfeld Jacob disease, Parkinson's disease, HIV-related dementia, ALS (amyotropic lateral sclerosis), inclusion-body myositis (IBM), type II diabetes, and senile cardiac amyloidosis; and various eye diseases including glaucoma, macular degeneration, drusen-related optic neuropathy, and cataract due to beta-amyloid deposition.

In the present disclosure, terms including "Aβ protofibril/oligomer" and "Aβ protofibril and/or oligomer Aβ" and similar language, are used with the understanding that Aβ oligomer and Aβ protofibril are recognized as soluble neurotoxic Aβ formed by monomers and would be expected to exist in samples, presumably in a variety different structures, conformations, associations, and molecular weights (e.g., protofibrils >75 kDa whereas oligomer <75 kDa), such that "Aβ protofibril/oligomer" can encompass Aβ protofibril, or Aβ oligomer, or a mixture of Aβ protofibril and Aβ oligomer, or complexes (associations) of Aβ protofibril with Aβ oligomer. Accordingly, terms such as "detecting Aβ protofibril/oligomer" are understood to encompass detecting any or all of Aβ protofibril, or Aβ oligomer, or both Aβ protofibril and Aβ oligomer, or complexes (associations) of Aβ protofibril with Aβ oligomer.

In the present disclosure, "preferential binding to Aβ protofibril/oligomer" or "preferentially binds soluble Aβ protofibril/oligomer" or similar language, is understood as showing selectivity or affinity for Aβ protofibril/oligomer, which can be measured by common methods known in the art, including those described herein. The calculated concentration at which approximately 50% of maximal binding (the calculated $EC_{50}$) occurs can often be used as an estimate of affinity. Because Aβ protein in a sample can be present in multiple conformations of Aβ secondary structure (monomer, oligomer/protofibril, fibril, etc.), it is understood that "preferential binding" or "selectivity" or similar language refers to measurably higher binding of an antibody or antibody fragment to Aβ oligomer/protofibril compared with binding of the same antibody or antibody fragment to Aβ monomer in the sample. One non-limiting approach to determining selectivity for Aβ oligomer/protofibril over Aβ monomer can be calculated as the ratio of $EC_{50}$ monomer measured in a capture ELISA assay to $IC_{50}$ oligomer measures in a competitive ELISA assay. This ratio is used to identify and rank anti-Aβ protofibril/oligomer antibodies and antibody fragments according to level of preferential binding to soluble Aβ oligomer/protofibril.

A "subject" is a mammal, where mammals include but are not limited to primates (e.g., humans and non-human primates such as monkeys), mammals commonly used for research such as rabbits and rodents (e.g., mice and rats), and domesticated animals (e.g., cows, sheep, cats, dogs, pigs, llamas, and horses). In certain embodiments, the subject is a human. The phrases "to a subject in need thereof" or "to a patient in need thereof" or "to a patient in need of treatment" or "a subject in need of treatment" may include subjects that would benefit from administration of the anti-Aβ protofibril/oligomer antibodies and antibody fragments disclosed herein, for treatment, prevention, diagnosis, screening, or monitoring of a condition associated with Aβ protein aggregation, in particular AD. It is understood that administration of anti-Aβ protofibril/oligomer antibodies or antibody fragments encompasses administration to "a subject in need thereof" can be interpreted as referring to a subject known or suspected to have a condition associated with Aβ protein aggregation, in particular AD. Anti-Aβ protofibril/oligomer antibodies or antibody fragments disclosed herein can be administered to a subject known or suspected to have a condition associated with Aβ protein aggregation, in particular AD, for therapeutic, preventative, or prophylactic purposes including but not limited to, for treating, for screening, for diagnostics, for monitoring, for research purposes, or to achieve results distinct from treating a disorder. It is further understood that anti-Aβ protofibril/oligomer antibodies or antibody fragments can be administered to a subject that is not known or suspected to have a condition associated with Aβ protein aggregation, for purposes that may include but are not limited to, preventative or prophylactic purposes, for screening, for diagnostics, for monitoring, for research purposes, or to achieve results distinct from treating a disorder.

Compositions

Anti-Aβ Protofibril/Oligomer Antibodies and Antibody Fragments that Show Selectivity for and Preferentially Bind to Soluble Aβ Protofibril/Oligomers, Trigger ACDP in Effector Cells, Penetrate Brain Tissue, Reduce Soluble Aβ Protofibril/Oligomer Levels in Brain Tissue, Reduce Insoluble Aβ Plaque in Brain Tissue Including Condense Plaque and Diffused Plaque, and Reduce Plaque Burden Antibodies and antigen-binding fragments are provided that show selectivity for, and preferentially bind to, soluble Aβ protofibril/oligomers. In particular, anti-Aβ antibodies and antigen-binding fragments are provided having sufficient constant region sequence that includes sufficient Fc structure/sequence such that complexes of the anti-Aβ protofibril/oligomer antibody or antibody fragment bound to Aβ protofibril/oligomer can trigger ADCP in effector cells with phagocytic potential, resulting in phagocytosis and thus removal of the complexes of the anti-Aβ protofibril/oligomer antibody or antibody fragment bound to Aβ protofibril/oligomer from solution surrounding the effector cell. Without wishing to be bound by a particular mechanism of action or hypothesis, ADCP-mediated removal of complexes of the anti-Aβ protofibril/oligomer antibody or antibody fragment bound to Aβ protofibril/oligomer from the solution surrounding the effector cell, may accomplish removal of soluble Aβ protofibril/oligomer from the solution. It is understood that ADCP-mediated removal of complexes of the anti-Aβ protofibril/oligomer antibody or antibody fragment bound to Aβ protofibril/oligomer from the solution surrounding the effector cell can occur in vivo, ex vivo, or in vitro. In vivo ADCP-mediated removal of complexes of the anti-Aβ protofibril/oligomer antibody or antibody fragment bound to Aβ protofibril/oligomer may occur in, inter alia, blood, lymph, cerebrospinal fluid (CSF), nervous tissue, or brain. Accordingly, in vivo ADCP-mediated removal of complexes of the anti-Aβ protofibril/oligomer antibody or antibody fragment bound to Aβ protofibril/oligomer may reduce soluble Aβ protofibril/oligomer levels in, inter alia, blood, lymph, cerebrospinal fluid (CSF), nervous tissue, or brain. Ex vivo or in vitro ADCP-mediated removal of complexes of the anti-Aβ protofibril/oligomer antibody or antibody fragment bound to Aβ protofibril/oligomer may occur in samples such as blood, lymph, cerebrospinal fluid (CSF) collected from a subject, or in other samples, and may reduce soluble Aβ protofibril/oligomer levels in such samples.

Anti-Aβ antibodies and antigen-binding fragments with fully human variable regions as provided herein, carry lower risk for inducing immune responses and are expected to present a reduced risk of adverse reactions or unwanted side effects when administered to a human subject. In contrast, humanized antibodies derived from a non-human antibody, such as lecanemab, a humanized IgG1 monoclonal antibody which preferentially binds Aβ protofibril/oligomer, may be expected to have a relatively higher risk for adverse reactions or unwanted side effects after administration.

Exemplary embodiments of antibodies and antigen-binding fragments that preferentially bind to soluble Aβ protofibril/oligomers and trigger ADCP include but are not limited to antibodies provided in the Examples and Tables 1, 2, 3, 4, and 5. In certain embodiments, anti-Aβ protofibril/oligomer antibodies with fully human variable regions produced by transgenic mice immunized with $A\beta_{1-42}$ protofibril, were recovered from hybridoma supernatants and screened as described in Example 1 to yield chimeric monoclonal antibodies having fully human F(ab')$_2$ and mouse CH2 and CH3 domains. In certain embodiments, thirty-three (33) lines chimeric monoclonal antibodies having fully human F(ab')$_2$ and mouse IgG1 CH2 and CH3 domains as listed in Table 1 were evaluated for their ability to preferentially bind to soluble Aβ protofibril/oligomers and trigger ADCP, and the VH and VL sequence of fifteen (15) antibodies of interest are provided in Tables 2 and 3. In certain embodiments, anti-Aβ protofibril/oligomer antibodies were prepared in different formats for different actual and potential uses, and evaluated for ability to preferentially bind to soluble Aβ protofibril/oligomers and trigger ADCP, including: chimeric monoclonal antibodies having fully human F(ab')$_2$ and mouse IgG1 CH2 and CH3 domains (i.e., chimeric human F(ab')$_2$/mouse IgG1 antibodies) tested as shown in Table 1, with variable region sequences presented in Tables 2 and 3; antibodies reformatted as fully human IgG1 lambda antibodies and tested as described in Example 5 and shown in Table 4; and antibodies reformatted as mouse IgG2a CH2-CH3/(fully human F(ab')$_2$ and mouse IgG2a CH2 and CH3 domains) and tested as described in Example 5 and shown in Table 5, and as used for Examples 6 and 7.

The sequence and format of anti-Aβ protofibril/oligomer antibodies and antibody fragments can be altered to develop antibodies or fragments having desired properties. In one non-limiting embodiment, an anti-Aβ protofibril/oligomer antibody or antibody fragment with desired properties for a particular use can be developed using suitable variable region frameworks comprising a VH comprising an HC CDR 1 having the amino acid sequence GFTLSSFS (SEQ ID NO: 42), an HC CDR2 having the amino acid sequence ISSRRTYI (SEQ ID NO: 43), and an HC CDR3 having the amino acid sequence ARGGYIGSPNAYDI (SEQ ID NO: 44), and a light chain variable region (VL) comprising an LC CDR 1 having the amino acid sequence TGAVTSDYY (SEQ ID NO: 47), an LC CDR2 having the amino acid sequence SAS, and an LC CDR3 having the amino acid sequence LLYYGGAWV (SEQ ID NO: 49), combined with constant region sequences that include Fc sequences selected to be suitable for that particular use. In another non-limiting embodiment, an anti-Aβ protofibril/oligomer antibody or antibody fragment with desired properties for a particular use can be developed using suitable variable region frameworks comprising a VH comprising an HC CDR 1 having the amino acid sequence GFTFSGSA (SEQ ID NO: 62), an HC CDR2 having the amino acid sequence IRSKANSYAT (SEQ ID NO: 63), and an HC CDR3 having the amino acid sequence TSHAPNFDAFDI (SEQ ID NO: 64), and a VL comprising an LC CDR 1 having the amino acid sequence SSNIGNHY (SEQ ID NO: 67), an LC CDR2 having the amino acid sequence DNS, and an LC CDR3 having the amino acid sequence GTWDSSLSTYV (SEQ ID NO: 69), combined with constant region sequences that include Fc sequences selected to be suitable for that particular use. In another non-limiting embodiment, an anti-Aβ protofibril/oligomer antibody or antibody fragment with desired properties for a particular use can be developed using suitable variable region frameworks comprising a VH comprising an HC CDR 1 having the amino acid sequence GFTFSGSA (SEQ ID NO: 72), an HC CDR2 having the amino acid sequence IRSKVNSYAT (SEQ ID NO: 73), and an HC CDR3 having the amino acid sequence TSHAPIFDAFDI (SEQ ID NO: 74), and a VL comprising an LC CDR1 having the amino acid sequence SSNIGNHY (SEQ ID NO: 77), an LC CDR2 having the amino acid sequence DNS, and an LC CDR3 having the amino acid sequence GTWDSSLSTYF (SEQ ID NO: 79), combined with constant region sequences that include Fc sequences selected to be suitable for that particular use. In another non-limiting embodiment, an anti-Aβ protofibril/oligomer antibody or antibody fragment with desired properties for a particular use can be developed using suitable variable region frameworks comprising a VH comprising an HC CDR 1 having the amino acid sequence GFTFSNAW (SEQ ID NO: 132), an HC CDR2 having the amino acid sequence IKSKTDGGTR (SEQ ID NO: 133), and an HC CDR3 having the amino acid sequence TTGYGEGY (SEQ ID NO: 134), and a VL comprising an LC CDR1 having the amino acid sequence SSNIKSNT (SEQ ID NO: 137), an LC CDR2 having the amino acid sequence RNN, and an LC CDR3 having the amino acid sequence AAWDDSLKGVV (SEQ ID NO: 139), combined with constant region sequences that include Fc sequences selected to be suitable for that particular use. In another non-limiting embodiment, an anti-Aβ protofibril/oligomer antibody or antibody fragment with desired properties for a particular use can be developed using suitable variable region frameworks comprising a VH comprising an HC CDR 1 having the amino acid sequence GFSFSNAW (SEQ ID NO: 2), an HC CDR2 having the amino acid sequence IKSKTDGGTI (SEQ ID NO: 3), and an HC CDR3 having the amino acid sequence TTGYGEGY (SEQ ID NO: 4), and a VL comprising an LC CDR1 having the amino acid sequence SSNIKSNT (SEQ ID NO: 7), an LC CDR2 having the amino acid sequence RNN, and an LC CDR3 having the amino acid sequence AAWDDSLKGVV (SEQ ID NO: 9), combined with constant region sequences that include Fc sequences selected to be suitable for that particular use. It is understood that "suitable variable region frameworks" are suitable human variable region frameworks that may be chosen or engineered for a particular property or use.

Anti-Aβ protofibril/oligomer antibodies and antibody fragments are provided that can penetrate brain tissue. In particular, anti-Aβ protofibril/oligomer antibodies and antibody fragments having fully human variable regions are provided that can penetrate brain tissue. It is understood that brain penetrance, i.e., an ability to cross the blood-brain barrier, allows an antibody or antibody fragment to act on targets within brain tissue. Without wishing to be bound by a particular mechanism of action or hypothesis, ADCP-mediated removal of complexes of the anti-Aβ protofibril/oligomer antibody or antibody fragment bound to Aβ protofibril/oligomer in brain tissue may have effects that can include to reduce levels of soluble Aβ protofibril/oligomer in brain tissue. Without wishing to be bound by a particular mechanism of action or hypothesis, ADCP in brain tissue triggered by anti-Aβ protofibril/oligomer antibodies or antibody fragment bound to targets, may have effects that may include to reduce the amount of Aβ plaque in brain tissue. It is understood that reducing the amount of Aβ plaque may encompass clearing Aβ plaque from tissues and fluids.

Exemplary embodiments of anti-Aβ protofibril/oligomer antibodies and antibody fragments that were tested as described in Example 6 can penetrate brain tissue include but are not limited to: 18P01A(mIgG2a) (HC amino acid sequence SEQ ID NO: 155; LC amino acid sequence SEQ ID NO: 156) including 18P01A fully human VH having the amino acid sequence of SEQ ID NO: 61, and 18P01A fully human VL having the amino acid sequence of SEQ ID NO: 66; and 17P04A(mIgG2a) (HC amino acid sequence SEQ ID NO: 151; LC amino acid sequence SEQ ID NO: 152_ including 17P04A fully human VH having the amino acid sequence of SEQ ID NO: 41, and 17P04A fully human VL having the amino acid sequence of SEQ ID NO: 46) Both embodiments show acceptable half-life in serum after dosing (FIG. 9) and are detectable in brain tissue after dosing (FIG. 10), where 18P01A(mIgG2a) has 0.3% brain penetrance and a half-life of 77.2 hrs in brain tissue, and 17P04A(mIgG2a) has 5.5% brain penetrance and a half-life of 92.4 hrs in brain tissue. Additional anti-Aβ protofibril/oligomer antibodies and antibody fragments provided here can be evaluated for serum half-life, brain penetrance, and brain half-life.

Figure 15B:
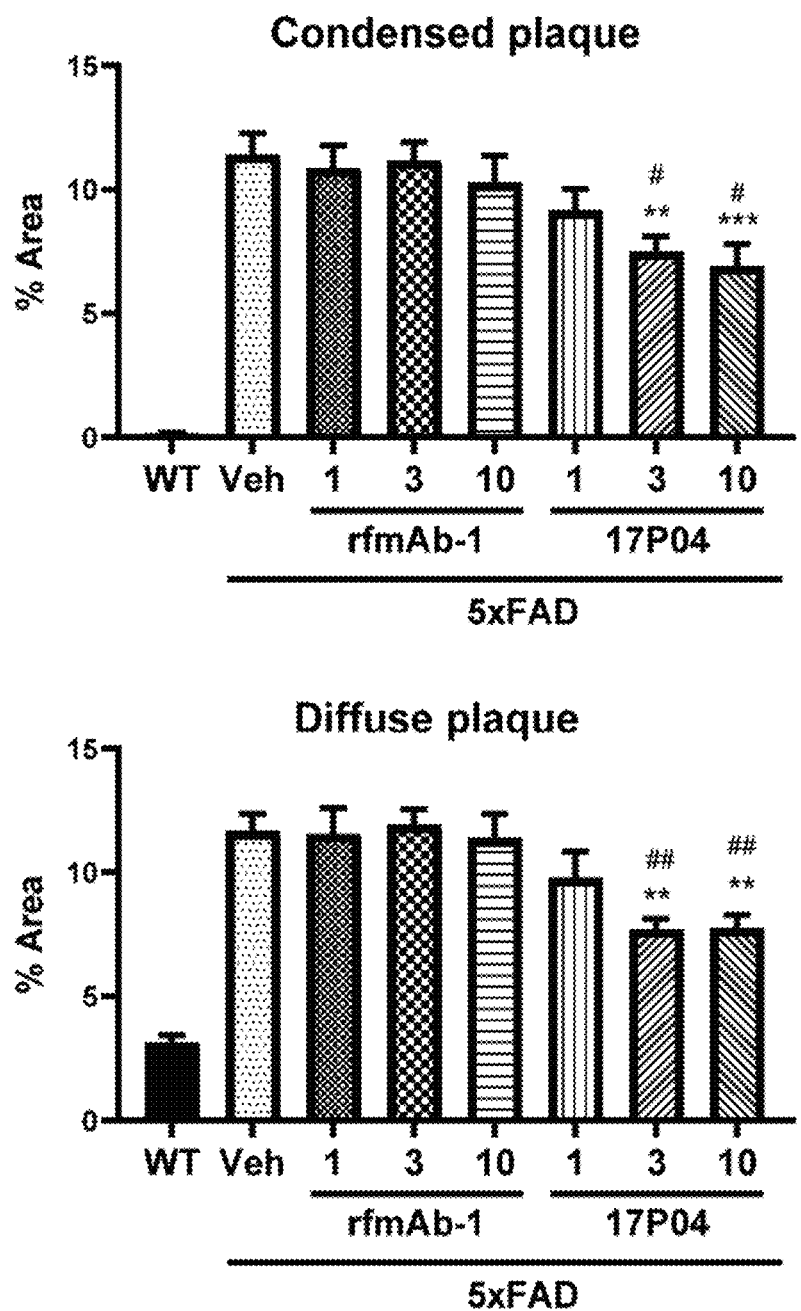

Anti-Aβ protofibril/oligomer antibodies and antibody fragments are provided that can reduce levels of soluble Aβ oligomer/protofibril and reduce levels of insoluble Aβ plaque, including condensed plaque and diffused plaque, in the brain of a mammalian subject after administration to the subject. In particular, anti-Aβ protofibril/oligomer antibodies and antibody fragments having fully human variable regions are provided that can reduce levels of soluble Aβ oligomer/protofibril and reduce levels of insoluble Aβ plaque, including condensed plaque and diffused plaque, in the brain of a mammalian subject after administration to the subject. Without wishing to be bound by a particular mechanism of action or hypothesis, reducing levels of insoluble Aβ plaque in brain tissue may encompass reducing or preventing or slowing Aβ protein aggregation and deposition as insoluble Aβ plaque. An animal model for a condition associated with Aβ protein aggregation was used to measure effects of anti-Aβ protofibril/oligomer antibodies and antibody fragments on soluble Aβ oligomer/protofibril and reduce levels of insoluble Aβ plaque in brain tissue after administration. In a non-limiting exemplary embodiment using 5×FAD mice as an AD mouse model to evaluate the long-term efficacy of an anti-Aβ protofibril/oligomer antibody (Example 7), results showed that administration of 17P04A(mIgG2a) can reduce levels of soluble Aβ oligomer/protofibril (FIG. 13) and reduce levels of insoluble Aβ plaque, including condensed plaque and diffused plaque, (FIGS. 15A-15B) in the brains of 5×FAD mice, compared with levels of soluble Aβ oligomer/protofibril and levels of insoluble Aβ plaque in control 5×FAD mice injected with vehicle (PBS) for the same amount of time. 17P04A (mIgG2a) (HC SEQ ID NO: 151, LC SEQ ID NO: 152) exerted effects on soluble Aβ oligomer/protofibril (FIG. 13) and insoluble Aβ plaque (FIG. 15B) in a dose-dependent manner, thereby providing an example of how to evaluate parameters such as antibody concentration, administration frequency, and treatment duration for an antibody, to find optimal conditions for maximizing therapeutic effectiveness and avoiding unwanted side effects. Additional anti-Aβ protofibril/oligomer antibodies and antibody fragments provided here can be evaluated for effects on soluble Aβ oligomer/protofibril and insoluble Aβ plaque in brain tissue after administration to a subject.

Compositions are provided that include the present anti-Aβ protofibril/oligomer antibody or antibody fragment and pharmaceutically acceptable carrier(s) or excipient(s) suitable for the intended use(s) of each composition. Such carriers include but are not limited to: saline, buffer, glucose, water, glycerol, ethanol, excipient, stabilizer, preservative, or combinations thereof. It is understood that the pharmaceutical preparation should match the administration mode.

Anti-Aβ protofibril/oligomer antibodies and antibody fragments disclosed herein can be administered to a subject by any suitable means, including but not limited to injection or parenteral administration. Parenteral administration can include intramuscular, intravenous, intraarterial, intraperitoneal ("ip"), subcutaneous, intraspinal (including epidural or intrathecal), intraocular, intracerebral, intracerebroventricular, intracardiac, intradermic/intradermal, intraarticular, intralymphatic, or intraosseous administration. Anti-Aβ oligomer antibodies and antibody fragments disclosed herein for introduction into the circulatory system by parenteral administration, in particular intraperitoneal administration. Anti-Aβ protofibril/oligomer antibodies and antibody fragments disclosed herein can be administered using a device, or as a depot, or in a sustained-release preparations (e.g., semipermeable matrices of solid hydrophobic polymers containing the antibody, or microcapsules) to allow slow and/or measured and/or localized delivery. Anti-Aβ protofibril/oligomer antibodies and antibody fragments disclosed herein can be formulated and administered using colloidal drug delivery systems (for example, liposomes, albumin microspheres, microemulsions, nano-particles and nanocapsules) or in macroemulsions.

Methods

Methods are provided for treating, preventing, diagnosing, screening for, or monitoring a condition associated with Aβ protein aggregation, in particular AD, using an effective amount of an anti-Aβ protofibril/oligomer antibody or antibody fragment disclosed herein. Without wishing to be bound by a particular mechanism of action, methods are provided for precise targeting and inhibition of the amounts and effects of Aβ protofibril/oligomer, in particular soluble Aβ protofibril/oligomer, using anti-Aβ protofibril/oligomer antibodies and antibody fragments disclosed herein. Methods for precise targeting and inhibition of soluble Aβ protofibril/oligomer can be methods for using routes of administration to target locations or systems involved in a disorder, methods for using timing of administration to target critical periods, and combinations of these methods.

Methods are provided for treating a condition associated with Aβ protein aggregation, in particular AD, by removing soluble Aβ protofibril/oligomer from tissue, fluids, or samples. Without wishing to be bound by a particular mechanism of action, methods are provided for treating a condition associated with Aβ protein aggregation by removing or reducing levels of precursors of Aβ protein aggregation, in particular by ADCP-mediated removal of complexes of the anti-Aβ protofibril/oligomer antibody or antibody fragment bound to Aβ protofibril/oligomer. Methods and compositions are provided for treating a disorder associated with Aβ protein aggregation, in particular AD, that can be used to remove soluble Aβ protofibril/oligomer from blood, lymph, cerebrospinal fluid (CSF) collected from a subject, or in samples of interest. It is understood that in vivo methods for treating a condition associated with Aβ protein aggregation involve administering a therapeutic amount of anti-Aβ protofibril/oligomer antibody or antibody fragment to a subject.

Methods and compositions provided herein allow strategic timing of treatments. Without wishing to be bound by a particular mechanism of action, anti-Aβ protofibril/oligomer antibodies and antibody fragments disclosed herein can be administered after screening or diagnosis indicates that a subject has or is suspected of having a condition associated with Aβ protein aggregation, in particular AD. Accordingly, anti-Aβ protofibril/oligomer antibodies and antibody fragments disclosed herein can be administered at a time where prevention or further development of a condition associated with Aβ protein aggregation, in particular AD, could be arrested or perhaps reversed. Without wishing to be bound by a particular mechanism of action, anti-Aβ protofibril/oligomer antibodies and antibody fragments disclosed herein can be administered to a subject identified as being at risk of having or developing a condition associated with Aβ protein aggregation, in particular AD. Accordingly, anti-Aβ protofibril/oligomer antibodies and antibody fragments disclosed herein can be administered at a time where onset or further development of a condition associated with Aβ protein aggregation, in particular AD, could be prevented or arrested. Furthermore, anti-Aβ protofibril/oligomer antibodies and antibody fragments disclosed herein can be administered prophylactically.

Methods and compositions provided herein allow control of the amount of therapeutic or prophylactic agent present at one or more time points during treatment. Without wishing to be bound by a particular mechanism of action, anti-Aβ protofibril/oligomer antibodies and antibody fragments disclosed herein can be administered and effects can be monitored, e.g., reactions such as edema or inflammation, indicators such as soluble Aβ protofibril/oligomer levels or levels of other Aβ conformations (monomers, fibrils, plaques), or clinical measurements of cognitive function. Without wishing to be bound by a particular mechanism of action, the dose or "effective amount" sufficient to produce at least one desired effect (e.g., reduced soluble Aβ protofibril/oligomer levels, reduced Aβ plaque levels, or improved cognitive function), with few or tolerable unwanted effects (e.g., edema or inflammation) may depend on factors specific to a subject in need thereof, such that treatment may comprise determining the dose of anti-Aβ protofibril/oligomer antibody or antibody fragment needed to constitute an effective amount for the subject, and administering that effective amount of anti-Aβ protofibril/oligomer antibody or antibody fragment to the subject.

Methods are provided for diagnosing or screening for at least one condition associated with Aβ protein aggregation in a subject by using at least one anti-Aβ protofibril/oligomer antibody or antibody fragment as disclosed herein, to detect the presence of soluble Aβ protofibril/oligomer, and optionally the amount of soluble Aβ protofibril/oligomer, in a sample from the subject. The sample may be a soluble fraction or a fixed tissue sample. It is understood that a method of diagnosing or screening includes comparing results such as the amount of soluble Aβ protofibril/oligomer in the sample, with at least one reference value related to the presence and/or amount of soluble Aβ protofibril/oligomer in other samples. Reference values can be based on samples from other subjects that may or may not be considered to have a condition associated with Aβ protein aggregation, in particular AD, or values in samples from the same subject taken at different points in time.

A method for producing an anti-Aβ protofibril/oligomer antibody or antibody fragment that preferentially binds soluble Aβ protofibril/oligomer and has a fully human variable region, using a functional screening approach. The method comprises immunizing a mammal that produces antibodies with human variable regions by introducing a preparation of purified Aβ protofibril (that may include oligomer) into the mammal, collecting enriched B cells and fusing the B cells with a myeloma fusion partner to create hybridomas, recovering antibodies from each of the hybridomas, conducting a primary screen of the recovered antibodies from each of the hybridomas comprising measuring binding to Aβ peptide in an ELISA-based assay, identifying and recovering any antibody with a sufficient level of detectable binding to Aβ peptide, conducting a confirmation screen of each recovered antibody after the primary screen comprising measuring competition of Aβ monomer and Aβ protofibril for binding to the recovered antibody using competitive ELISA, and measuring direct binding of each recovered antibody to Aβ monomer, Aβ protofibril and Aβ fibril by ELISA, and further comprising selecting each recovered antibody showing higher affinity for protofibril over monomer in competitive ELISA. It is understood that the mammal is engineered to produce antibodies with human variable regions, where mice are commonly engineered for such functions. Each anti-Aβ protofibril/oligomer antibody or antibody fragment can be formatted to specific tests or functions, e.g., by combining a constant region that includes an Fc region having a desired function and/or species compatibility, with a variable region (VH/VL) characterized having a desired level of selectivity for, and preferential binding to, soluble Aβ protofibril/oligomer. Further screening and characterization steps are provided that include measuring the ability of an anti-Aβ protofibril/oligomer antibody or antibody fragment to trigger ADCP-mediated removal of complexes of the anti-Aβ protofibril/oligomer antibody or antibody fragment bound to Aβ protofibril/oligomer, and assessing brain penetrance of an anti-Aβ protofibril/oligomer antibody or antibody fragment and subsequent reduction of plaque levels in brain tissue indicating ability to clear plaque. Suitable Fc regions for use with the anti-Aβ protofibril/oligomer antibody or antibody fragment provided herein can be, but are not limited to, complete or partial Fc regions of mouse IgG1, human IgG1, mouse IgG2a, human IgG3 and mouse IgG2b.

In a non-limiting exemplary embodiment, results of a long-term efficacy study show that treatment with an antibody having a fully human VH comprising 17P04A HC CDR1 having the sequence GFTLSSFS (SEQ ID NO: 42), 17P04A HC CDR2 having the sequence ISSRRTYI (SEQ ID NO: 43), and 17P04A HC CDR3 having the sequence ARGGYIGSPNAYDI (SEQ ID NO: 44), and a fully human VL comprising 17P04A LC CDR1 having the sequence TGAVTSDYY (SEQ ID NO: 47), 17P04A LC CDR2 having the sequence SAS, and 17P04A LC CDR3 having the sequence LLYYGGAWV (SEQ ID NO: 49), efficiently and effectively removes soluble Aβ oligomer/protofibril, and insoluble Aβ fibril/plaque (including both condensed and diffuse plaque) in brain thereby reducing the plaque burden in vivo in an AD disease model.

The following examples are offered to illustrate, but not to limit, the claimed invention.

EXAMPLES

Example 1: Generation and Identification of Antibodies that Bind Amyloid Beta (Aβ) Oligomer/Protofibril The production of novel monoclonal antibodies against amyloid beta (Aβ) oligomers was carried out under contract by AlivaMab Discovery Services, LLC (San Diego, CA). The AMX-KL mouse, a transgenic mouse line producing antibodies with fully-human F(ab')$_2$ and mouse CH2 and CH3 domains wherein the fully human F(ab')$_2$ comprises human VH and VL, and human CL and CH1, was licensed from Ablexis, LLC (ablexis.com; San Diego, CA) and used in immunization for the discovery of therapeutic antibodies. AMX-KL mice were immunized with freshly prepared Aβ protofibrils. Preparation of Aβ$_{1-42}$ protofibril followed the protocol detailed below and the chromatographic profile was illustrated in FIG. 1. Enriched B cells from spleen and lymph nodes of mice with sufficient plasma titers were fused with a myeloma fusion partner, triggering downstream antibody recovery and screening activities. Enzyme-linked immunosorbent assay (ELISA) techniques were used in a series of screening and characterization steps. Initially, 15662 hybridoma supernatants were subjected to a primary screen for binding to Aβ peptide in an ELISA-based assay. The top 186 hits with >6.9 million RLU binding to Aβ peptide were selected to move forward to a confirmation screen, which included measuring competition of Aβ monomer and protofibril, and direct binding with monomer, protofibril and fibril using ELISA. Thirty-three (33) hits showing higher affinity for protofibril over monomer in competitive ELISA were selected from the confirmation screen and purified. After purification, each of the 33 monoclonal antibodies (mAbs) were characterized and ranked in a panel of in vitro assays (results shown in Table 1) and the five (5) best-performing mAbs were identified as lead candidates. Fifteen (15) of the antibodies were subcloned and variable region sequence was obtained (see Table 2 and Table 3). The five (5) lead candidates were purified and characterized. The 5 lead candidates were then reformatted for further characterization and development as (a) fully human antibodies and (b) chimeric antibodies with different mouse isotypes)
Preparation of Different Aβ Conformations 1 mg of Aβ$_{1-42}$ monomer (rPeptide, A-1167-2; rpeptide-.com) was solubilized in 200 μL of 12 mM NaOH. The solution was neutralized with 1200 μL 10×PBS (final pH ~8.8) and incubated at 37° C. for 2 h to allow the formation of protofibril. The aggregation state of Aβ$_{1-42}$ was monitored by a Thioflavin T assay (Sigma, T3516; sigmaaldrich.com; as 10 UM of Thioflavin T in the sample solution). This method generated an protofibril/monomer mixture containing ~70% protofibril and ~30% monomer, as shown in in FIG. 1 presenting results of size exclusion chromatography (SUPERDEX™ 200 Increase 10/300 GL, Cytiva 28-9909-44) of the mixture. This protofibril/monomer mixture was freshly prepared on each immunization day. Experiments were conducted under the assumption that any Aβ$_{1-42}$ monomer in the mixture was not likely to trigger immune responses due to its small size (MW 4514 Da).

To prepare purified Aβ$_{1-42}$ protofibril for antibody screening, the fractions of protofibril peak in size exclusion chromatography was collected and stored at −80° C. This purified Aβ$_{1-42}$ protofibril stock is stable in −80° C. for at least 2 months and can resist several freeze and thaw cycles. Aβ$_{1-42}$ monomer was unstable and not suitable for antibody screening. Therefore, Aβ$_{1-40}$ monomer lacking two amino acid residues at C-terminus (rPeptide, A-1157-2) was used as the monomer conformation for antibody screening. Aβ$_{1-40}$ monomer was stable at 4° C. for at least 24 h and can be stored in −80° C. for at least 2 months. Aβ$_{1-42}$ fibril was purchased as preformed fibril from rPeptide (rPeptide, Catalog #AF-1002).

Example 2: Characterization and Ranking of Anti-Aβ Protofibril/Oligomer Monoclonal Antibodies A series of ELISA-based binding assays including direct ELISA, competitive ELISA, and capture ELISA were developed for the screening of hybridomas and characterization of mAbs. In addition, an antibody-dependent cell-mediated phagocytosis (ADCP) assay was developed to evaluate the ability (potential) of anti-Aβ antibodies to mediate the uptake of Aβ protofibril by microglia. Two control antibodies, an anti-Aβ protofibril/oligomer antibody reference antibody-1 (rfmAb-1) and non-conformation selective anti-Aβ antibody 6E10 (BioLegend, 803001), referred to as rfmAb-2, were used as references in those assays.
Direct ELISA High-binding 96-well plates (Corning, 9018) were coated with 0.5 μM of Aβ monomer or Aβ protofibril or Aβ fibril for 2 h at 4° C. After 3 washes with 1× Phosphate-Buffered Saline (PBS), 0.1% TWEEN® 20 (polyoxyethylene (20) sorbitan monolaurate) (PBST), each plate was blocked with 1% bovine serum albumin (BSA) in PBS for 1 h at room temperature (RT). Diluents of Aβ antibodies (3-fold serial dilutions with concentrations in the range of 0-100 nM) were added to plates. The plate was incubated for 1 h at RT and washed 3 times. The plate was then incubated with horseradish peroxidase (HRP) conjugated goat anti-mouse IgG (Thermo Fisher Scientific, G-21040; thermofisher.com) 1:5000 diluted in 1% BSA for 1 h at RT and washed 3 times. TMB (3,3',5,5;-tetramethylbenzidine) Stabilized Chromogen substrate solution (Life Technologies (Thermo Fisher Scientific) SB02) was added to the plate, and the reaction was stopped by adding 1M sulfuric acid. The absorbance at 450 nm was measured in a plate reader. Results for rfmAb-1 (oligomer/protofibril selective anti-Aβ antibody) and rfmAb-2 (non-conformation selective anti-Aβ antibody) showed similar affinities for Aβ monomers and protofibrils in the direct ELISA (FIG. 2). This suggests that direct ELISA can measure the general affinities of antibodies for Aβ peptide but cannot determine their selectivity for different Aβ conformations.
Competitive ELISA Aβ antibodies were pre-incubated with diluents of Aβ monomer or Aβ protofibril or Aβ fibril (3-fold serial dilutions with concentrations in the range of 0-3000 nM) for 1 h at 4° C. The concentration of Aβ antibody used in the antibodies-Aβ mixture was the EC90 of that antibody with Aβ monomers as measured in the direct ELISA experiments. The mixture was then applied to an ELISA plate pre-coated with 0.5 μM Aβ monomer. The plate was incubated for 10 min at RT and washed 3 times with PBST. The plate was then incubated with HRP conjugated goat anti-mouse IgG (Thermo Fisher Scientific, G-21040) 1:5000 diluted in 1% BSA for 1 h at RT and washed 3 times. TMB substrate solution (Life Technologies, SB02) was added to the plate, and the reaction was stopped by adding 1M sulfuric acid. The absorbance at 450 nm was measured in a plate reader. As shown in FIG. 3, rfmAb-1 mixed with Aβ protofibril has low binding with Aβ monomer while rfmAb-1 mixed with Aβ monomer or fibril has high binding with Aβ monomer (FIG. 3A), indicating that rfmAb-1 has high affinity for Aβ oligomer over Aβ monomer or fibril, which is consistent with its known binding profile. As shown in FIG. 3, rfmAb-2 showed similar affinities for Aβ monomer and Aβ protofibrils in competitive ELISA (FIG. 3B), which is also consistent with its known profile. These results suggest that competitive ELISA can distinguish the selectivity of anti-Aβ antibodies for different Aβ conformations.

Capture ELISA

Figure 4:
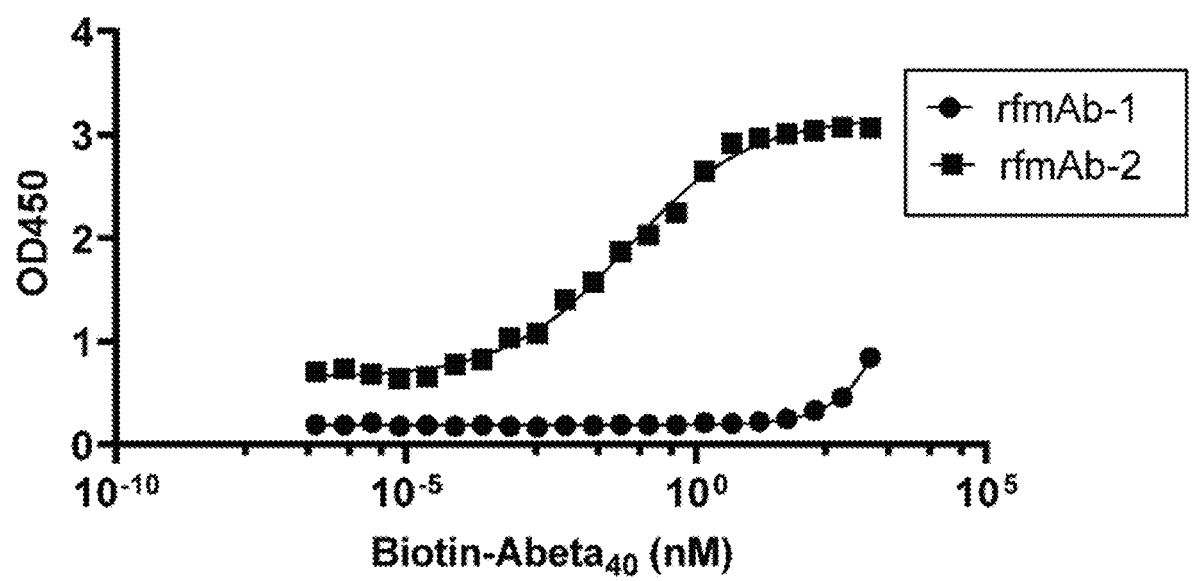
FIG. 4 shows results for capture ELISA of reference antibodies rfmAb-1 and rfmAb-2. Each antibody (at 100 ng per well) was coated on a 96-well plate. Diluents of biotin-conjugated Aβ$_{40}$ monomer was applied to the plate for 1 h and binding was detected by HRP-conjugated streptavidin and TMB substrate. The EC50 for rfmAb-1 (solid circles) could not be reliably measured and is considered unstable. The EC50 for rfmAb-2 (solid squares) is 0.067 nM.

High-binding 96-well plates (Corning, 9018) were coated with 5 μg/mL of Aβ antibodies overnight at RT and washed 3 times with PBST. Diluents of biotin-labelled $A\beta_{1-40}$ monomer (AnaSpec, AS-61483-01, 4-fold serial dilutions with concentrations in the range of 0-1000 nM) was then applied to the plate and captured by the immobilized antibody. The plate was incubated for 1 h at RT and washed 3 times with PBST. The plate was then incubated with HRP-conjugated streptavidin (Thermo Fisher Scientific, SNN2004) at 1:5000 diluted in 1% BSA for 20 min at RT and washed 3 times. TMB Stabilized Chromogen substrate solution (Life Technologies, SB02) was added to the plate, and the reaction was stopped by adding 1M sulfuric acid. The absorbance at 450 nm was measured in a plate reader. FIG. 4 illustrated that rfmAb-1 had weak binding with $A\beta_{1-40}$ monomer over the entire range of concentrations tested, while rfmAb-2 showed strong binding with $A\beta_{1-40}$ monomer in a concentration-dependent manner, consistent with the known affinities of each reference antibody for Aβ monomer. These results suggest that capture ELISA can determine the affinities of anti-Aβ antibodies for Aβ monomer.

Antibody-Dependent Cell-Mediated Phagocytosis (ADCP) Assay

Aβ protofibrils labelled with HILYTE™ 488 Fluorophore (AnaSpec, AS-60479-01; anaspec.com) were prepared as follows. First, 0.1 mg of HILYTE™ 488 labeled $A\beta_{1-42}$ monomers resuspended in 18 μL of 12 mM NaOH were mixed with 0.5 mg unlabeled $A\beta_{1-42}$ monomers (rPeptide, A-1167-1) resuspended in 90 μL of 12 mM NaOH. Next, 680 μL of 10×PBS pH7.4 (Gibco 70011-044) was then added to the mixture of labeled and unlabeled $A\beta_{1-42}$ monomers. The mixture was incubated at 37° C. for 2 h to form HILYTE™ 488 labelled $A\beta_{1-42}$ protofibrils. Protofibrils were then centrifuged at 16,000 g for 5 min at 4° C. to remove insoluble fibril. The supernatant was run in size exclusion chromatography (SUPERDEX® 200 Increase 10/300 GL, Cytiva 28-9909-44) and the protofibril peak similar to the protofibrils peak in FIG. 1 was separated.

Second, mouse microglia cell line BV-2 cells (AcceGen, ABC-TC212S; accegen.com) were seeded to 96-well cell culture plates at a density of 60,000 cells per well and incubated overnight. Cells were pre-treated with ADCP assay diluent which contains DMEM/F12 (Dulbecco's Modified Eagle Medium: Nutrient Mixture F-12) with HEPES ((4-(2-hydroxyethyl)-1-piperazineethanesulfonic acid) media (Gibco, 11039021), 1% BSA, and 100 μg/mL Fucoidan (Sigma-Aldrich, F8190) for 1 h at 37° ° C. before the ADCP assay. 2.25 μg/mL of HILYTE™ 488 oligomers were mixed with serial dilutions (800, 160, 32, and 6.4 ng/ml) of Aβ antibodies or mouse IgG2b (negative control) in ADCP assay diluent for 30 min. The mixture was added to BV-2 cells and incubated at 37° C. for 1.5 h to induce ADCP. Cell-surface-bound oligomer-antibody complex was removed by treatment with 0.25% trypsin for 20 min at 4° C. Cells were gently scraped from the culture plate and transferred to a conical bottom 96-well plate (Thermo Scientific, 249935). Cells were then rinsed twice with ice cold cell staining buffer (BioLegend, 420201), fixed for 20 min in ice cold fixation buffer (BioLegend, 420801), and rinsed once again. Finally, cells were analyzed by flow cytometry for fluorescence, which reflected the amount of HILYTE™ 488 labelled oligomers that were taken by the cells.

Ranking of Aβ Protofibril-Binding Monoclonal Antibodies

The 33 Aβ protofibril-binding mAbs described above (Example 1) were tested using direct ELISA, competitive ELISA, and capture ELISA to evaluate their affinities for different Aβ conformations, and in the ADCP assay for their ability to mediate the uptake of Aβ protofibril by microglia. The results are compiled in Table 1, in which the mAbs were ranked based on the ratio of $EC_{50}$ monomer in capture ELISA to $IC_{50}$ protofibril in competitive ELISA. This ratio reflects their selectivity for protofibril over monomer. Based on the totality of the data, mAbs 18P01A, 17P04A, 20O07A, 22D04A, and 06E17A were selected as lead candidates. For these lead candidates, mAbs 18P01A, 17P04A, 20O07A were selected as the top three antibodies on the basis of high Aβ protofibril selectivity, mAb 22D04A was selected for the highest ADCP activity among the candidates, and 06E17A was selected due to its highest affinity to fibril.

TABLE 1

Characterization and ranking of 33 anti-Amyloid beta monoclonal antibodies. The list was sorted by selectivity for protofibril over monomer calculated as the ratio of $EC_{50}$ monomer (capture ELISA) to $IC_{50}$ protofibril (competitive ELISA). rfmAb-1 is the reference antibody of this study. The 5 antibodies in bold (18P01A, 17P04A, 20O07A, 22D04A, and 06E17A) are identified as lead candidates for further testing and development. UND, undetermined value.

| | Direct ELISA | | Competitive ELISA | | | | Capture ELISA | | |
|---|---|---|---|---|---|---|---|---|---|
| Monoclonal Antibody Names | $EC_{50}$ Abeta 1-42 (nM) | $EC_{50}$ Abeta p3-42 (nM) | $IC_{50}$ oligomer (nM) | $IC_{50}$ monomer (nM) | $IC_{50}$ fibril (nM) | $IC_{50}$ monomer/ $IC_{50}$ oligomer | $EC_{50}$ monomer (nM) | $EC_{50}$ monomer/ $IC_{50}$ oligomer | ADCP (RFU) |
| 18P01A | 0.062 | UND | 3.5 | 4601.0 | 162.8 | 1311.2 | 67.00 | 19.094 | 479773 |
| 17P04A | 0.045 | UND | 3.1 | 8433.0 | 130 | 2758.6 | 35.19 | 11.511 | 283889 |
| rfmAb-1 | 0.043 | 21.6 | 2.0 | 4124.0 | 116.9 | 2062.0 | 7.72 | 3.860 | 355869 |
| 20O07A | 0.050 | UND | 3.0 | 934.9 | 67.3 | 313.3 | 2.57 | 0.861 | 334158 |
| 15M13A | 0.038 | UND | 1.5 | 3187.0 | 83 | 2058.8 | 0.78 | 0.505 | 273400 |
| 21K12A | 0.037 | UND | 1.9 | UND | 102 | UND | 0.87 | 0.462 | 523503 |
| 22D04A | 0.035 | UND | 2.5 | UND | 111 | UND | 1.05 | 0.421 | 546803 |

TABLE 1-continued

Characterization and ranking of 33 anti-Amyloid beta monoclonal antibodies. The list was sorted by selectivity for protofibril over monomer calculated as the ratio of $EC_{50}$ monomer (capture ELISA) to $IC_{50}$ protofibril (competitive ELISA). rfmAb-1 is the reference antibody of this study. The 5 antibodies in bold (18P01A, 17P04A, 20O07A, 22D04A, and 06E17A) are identified as lead candidates for further testing and development. UND, undetermined value.

| | Direct ELISA | | | | | | Capture ELISA | | |
|---|---|---|---|---|---|---|---|---|---|
| | $EC_{50}$ | $EC_{50}$ | | Competitive ELISA | | | | | |
| Monoclonal Antibody Names | Abeta 1-42 (nM) | Abeta p3-42 (nM) | $IC_{50}$ oligomer (nM) | $IC_{50}$ monomer (nM) | $IC_{50}$ fibril (nM) | $IC_{50}$ monomer/ $IC_{50}$ oligomer | $EC_{50}$ monomer (nM) | $EC_{50}$ monomer/ $IC_{50}$ oligomer | ADCP (RFU) |
| 21P22A | 0.40 | UND | 4.1 | 7493.0 | 216 | 1809.0 | 1.18 | 0.286 | 501805 |
| 17D08A | 0.075 | UND | 12.3 | 8280 | 340.8 | 675.9 | 0.34 | 0.028 | 193621 |
| 22H10A | 0.075 | UND | 6.1 | UND | 115.9 | UND | 0.07 | 0.012 | 99088 |
| 22C01A | 0.035 | UND | 1.2 | 143636 | 42.0 | 123717.5 | 0.01 | 0.012 | 239232 |
| 21G10A | 0.042 | UND | 2.3 | 4169 | 93.1 | 1780.9 | 0.02 | 0.010 | 244881 |
| 22H16A | 0.075 | UND | 4.8 | 2512 | 158.1 | 520.4 | 0.03 | 0.007 | 94682 |
| 06E17A | 0.052 | UND | 4.5 | 2579 | 38.6 | 569.4 | 0.02 | 0.005 | 301344 |
| 17H05A | 0.051 | UND | 3.6 | 29023 | 101.4 | 8019.6 | 0.02 | 0.005 | 279098 |
| 20O11A | 0.050 | UND | 2.7 | 671.6 | 112.3 | 248.3 | 0.01 | 0.004 | 257107 |
| 21F12A | 0.048 | UND | 2.3 | 16777 | 81.6 | 7403.8 | 0.01 | 0.004 | 261651 |
| 18F06A | 0.068 | UND | 7.8 | UND | 227.2 | UND | UND | UND | 126334 |
| 22G09A | 0.028 | UND | 1.1 | 1321.0 | 72 | 1180.5 | UND | UND | UND |
| 19C20A | 0.057 | UND | 7.7 | 5192.0 | 523 | 674.6 | UND | UND | UND |
| 21L19A | 0.087 | UND | 10.1 | 4673.0 | 302.7 | 464.1 | UND | UND | UND |
| 21P11A | 0.049 | 3.0 | 4.9 | 2026.0 | 284 | 415.0 | UND | UND | UND |
| 15C17A | 0.036 | 11.8 | 5.3 | 222.4 | 551 | 41.8 | UND | UND | UND |
| 22E23A | 0.058 | UND | 9.8 | 133.6 | 2060 | 13.6 | UND | UND | UND |
| 21J20A | 0.073 | UND | 13.2 | 172.3 | 5962 | 13.1 | UND | UND | UND |
| 15H10A | 0.040 | 0.3 | 15.0 | 35.9 | UND | 2.4 | 0.02 | 0.001 | UND |
| 15E19A | 0.065 | 0.6 | 80.7 | 62.4 | 2789 | 0.8 | UND | UND | UND |
| 07I22A | 0.041 | 0.3 | 68.6 | 51.2 | UND | 0.7 | UND | UND | UND |
| 21O12A | 0.039 | 0.4 | 47.4 | 34.1 | 4790 | 0.7 | 0.01 | UND | UND |
| 07M22A | 0.059 | 0.7 | 91.6 | 60.4 | UND | 0.7 | UND | UND | UND |
| 22A21A | 0.105 | 18.3 | 20.0 | 9.5 | 346.2 | 0.5 | UND | UND | UND |
| 21F06A | 0.093 | 0.5 | 151.4 | 66.9 | 34474 | 0.4 | UND | UND | UND |
| 18K24A | 0.063 | 0.7 | 67.9 | 26.3 | 3204 | 0.4 | UND | UND | UND |
| 22B14A | 0.072 | 1.4 | 33.1 | 12.0 | 2181 | 0.4 | UND | UND | UND |

Example 3: Heavy Chain and Light Chain Variable Region Sequences of 15 Anti-Amyloid Beta Monoclonal Antibodies Sequence was obtained for the variable regions of fifteen (15) anti-Aβ mAbs of interest from Table 1, and CDRs were identified using IMGT numbering (imgt.org/). Table 2 below provides the amino acid sequences of the heavy chain (HC) variable region (VH) of each of the 15 anti-Aβ mAbs of interest from Table 1. Table 3 provides the amino acid sequence of the light chain (LC) variable region (VL) of each of the 15 anti-Aβ mAbs of interest from Table 1.

TABLE 2

Sequences of the HC variable region (VH) of 15 mAbs of interest. CDRs 1-3 of each HC variable region are underlined in the complete VH amino acid sequence, where the CDRs were identified using IMGT numbering. Each CDR is also listed separately and identified by SEQ ID NO: assigned to the CDR.

| mAb name | HC variable region sequence; CDRs underlined in complete VH amino acid sequence |
|---|---|
| 06E17A | 06E17A VH<br>EVQLVESGGGLVKPGGSLRLSCAASGFSFSNAWMSWVRQAPGKGLEWVGRIKSKTDGGTIDYAAPVK<br>GRFTISRDDSKNTLYLQMNSLKTEDTAVYYCTTGYGEGYWGQGTLVTVSS (SEQ ID NO: 1)<br>06E17A HC CDR1 GFSFSNAW (SEQ ID NO: 2)<br>06E17A HC CDR2 IKSKTDGGTI (SEQ ID NO: 3)<br>06E17A HC CDR3 TTGYGEGY (SEQ ID NO: 4) |
| 15M13A | 15M13A VH<br>QVTLKESGPGILQPSQTLSLTCSFSGFSLSTFGMGVGWIRQPSGKGLEWLAHIWWDDDKYYNPALKS<br>RLTISKDTSKNQVFLKIANVDTADTATYYCARLGYYPYWFFDVWGTGTTVTVSS (SEQ ID NO: 11)<br>15M13A HC CDR1 GFSLSTFGMG (SEQ ID NO: 12)<br>15M13A HC CDR2 IWWDDDK (SEQ ID NO: 13)<br>15M13A HC CDR3 ARLGYYPYWFFDV (SEQ ID NO: 14) |

TABLE 2-continued

Sequences of the HC variable region (VH) of 15 mAbs of interest.
CDRs 1-3 of each HC variable region are underlined
in the complete VH amino acid sequence, where the CDRs
were identified using IMGT numbering. Each CDR is also
listed separately and identified by SEQ ID NO: assigned to the CDR.

| mAb name | HC variable region sequence; CDRs underlined in complete VH amino acid sequence |
|---|---|

17D08A  17D08A VH
EVQLVESGGGLVQPGGSLKLSCAASGFTFSGSAIHWVRQASGKGLEWVGRIRSKVNSYATAYAASVK
GRFTISRDDSKNTAYLQMNSLKTEDTAVYYCTRHAPNFDAFDIWGQGTMVTVSS (SEQ ID NO:
21)
17D08A HC CDR1 GFTFSGSA (SEQ ID NO: 22)
17D08A HC CDR2 IRSKVNSYAT (SEQ ID NO: 23)
17D08A HC CDR3 TRHAPNEDAFDI (SEQ ID NO: 24)

17H05A  17H05A VH
EVQLVESGGGSVQPGGSLRLSCAASGFTFSSYWMHWVRQVPGKGLVWVSRINSDGSITSYADSVKGR
FTISRDNAKNTLYLQMNSLRAENTAVYYCARGGGSLDYWGQGTLVTVSS (SEQ ID NO: 31)
17H05A HC CDR1 GFTFSSYW (SEQ ID NO: 32)
17H05A HC CDR2 INSDGSIT (SEQ ID NO: 33)
17H05A HC CDR3 ARGGGSLDY (SEQ ID NO: 34)

17P04A  17P04A VH
EVQLVESGGGLVKPGGSLRLSCAASGFTLSSFSMNWVRQAPGKGLEWVSSISSRRTYIYYADSAKGR
FTFSRDNAKNSLYLQMNSLRAEDSAVYYCARGGYIGSPNAYDIWGQGTMVTVSS (SEQ ID NO:
41)
17P04A HC CDR1 GFTLSSFS (SEQ ID NO: 42)
17P04A HC CDR2 ISSRRTYI (SEQ ID NO: 43)
17P04A HC CDR3 ARGGYIGSPNAYDI (SEQ ID NO: 44)

18F06A  18F06A VH
EVQLVESGGGLVQPGGSLRLSCAASGFTFSSYWMHWVRQAPGKGLVWVSRINRDGSTTSYADSVKGR
FTISRDNAKNTLYLQMNRLRAEDTAVYYCARGGGAFDIWGQGTMVTVSS (SEQ ID NO: 51)
18F06A HC CDR1 GFTFSSYW (SEQ ID NO: 52)
18F06A HC CDR2 INRDGSTT (SEQ ID NO: 53)
18F06A HC CDR3 ARGGGAFDI (SEQ ID NO: 54)

18P01A  18P01A VH
EVQLVESGGGLVQPGGSLKLSCAVSGFTFSGSAMHWVRQASGKGLEWVGRIRSKANSYATAYAASVK
GRFTISRDDSKNTAFLQMNSLKTEDTAVYYCTSHAPNFDAFDIWGQGTMVTVSS (SEQ ID NO:
61)
18P01A HC CDR1 GFTFSGSA (SEQ ID NO: 62)
18P01A HC CDR2 IRSKANSYAT (SEQ ID NO: 63)
18P01A HC CDR3 TSHAPNEDAFDI (SEQ ID NO: 64)

20O07A  20O07A VH
EVQLVESGGGLVQPGGSLKLSCAVSGFTFSGSAIHWVRQASGKGLEWVGRIRSKVNSYATVYAASVK
GRFTISRDDSKNTAFLQMNSLKTEDTAVYYCTSHAPIFDAFDIWGQGTMVTVSS (SEQ ID NO:
71)
20O07A HC CDR1 GFTFSGSA (SEQ ID NO: 72)
20O07A HC CDR2 IRSKVNSYAT (SEQ ID NO: 73)
20O07A HC CDR3 TSHAPIFDAFDI (SEQ ID NO: 74)

20O11A  20O11A VH
EVQLVESGGGLVQPGGSLRLSCAASGFTFSSYWMHWVRQAPGKGLAWVARINSDGSSTSYADSVKGR
FTISRDNAKNTLYLQMNSLRAEDTAVYYCARGGGLFDYWGQGTLVTVSS (SEQ ID NO: 81)
20O11A HC CDR1 GFTESSYW (SEQ ID NO: 82)
20O11A HC CDR2 INSDGSST (SEQ ID NO: 83)
20O11A HC CDR3 ARGGGLFDY (SEQ ID NO: 84)

21F12A  21F12A VH
EVQLAESGGGSVQPGGSLRLSCAASGFTFSSYWMHWVRQVPGKGLVWVSRINSDGSTTTYADSVKGR
FTISRDNAKNTLYLQMNSLRAEDTAVYYCARGGGSLDYWGQGTLVTVSS (SEQ ID NO: 91)
21F12A HC CDR1 GFTESSYW (SEQ ID NO: 92)
21F12A HC CDR2 INSDGSTT (SEQ ID NO: 93)
21F12A HC CDR3 ARGGGSLDY (SEQ ID NO: 94)

21G10A  21G10A VH
EVQLVESGGGSVQPGGSLRLSCAASGFTFSSYWMHWVRQAPGKGLVWVSRINSDGSITTYADSVKGR
FTISRDNAKNTLYLQMNSLRAEDTAVYYCARGGGSLDYWGQGTLVTVSS (SEQ ID NO: 101)
21G10A HC CDR1 GFTFSSYW (SEQ ID NO: 102)
21G10A HC CDR2 INSDGSIT (SEQ ID NO: 103)
21G10A HC CDR3 ARGGGSLDY (SEQ ID NO: 104)

21K12A  21K12A VH
EVQLVESGGGLVKPGGSLRLSCAASGFTFSNAWMSWVRQAPGKGLEWVGRIKSKTDGGTRDYAAPVK
GRFTISRDDSKNTLYLQMNSLKTEDTAVYYCTTGYGEGYWGQGTLVTVSS (SEQ ID NO: 111)

TABLE 2-continued

Sequences of the HC variable region (VH) of 15 mAbs of interest.
CDRs 1-3 of each HC variable region are underlined
in the complete VH amino acid sequence, where the CDRs
were identified using IMGT numbering. Each CDR is also
listed separately and identified by SEQ ID NO: assigned to the CDR.

| mAb name | HC variable region sequence; CDRs underlined in complete VH amino acid sequence |
|---|---|
| | 21K12A HC CDR1 GFTFSNAW (SEQ ID NO: 112)<br>21K12A HC CDR2 IKSKTDGGTR SEQ ID NO: 113)<br>21K12A HC CDR3 TTGYGEGY (SEQ ID NO: 114) |
| 21P22A | 21P22A VH<br>EVQLVESGGGLVKPGGSLRLSCAASGFTFSNAWMSWVRQAPGKGLEWVGRIKSKTDGGTTDYAAPVK<br>GRFTISRDDSKNTLYLQMNSLKTEDTAVYYCTTGYGEGYWGQGTLVTVSS (SEQ ID NO: 121)<br>21P22A HC CDR1 GFTFSNAW (SEQ ID NO: 122)<br>21P22A HC CDR2 IKSKTDGGTT (SEQ ID NO: 123)<br>21P22A HC CDR3 TTGYGEGY (SEQ ID NO: 124) |
| 22D04A | 22D04A VH<br>EVQLVESGGGLVKPGGSLRLSCAASGFTFSNAWMSWVRQAPGKGLEWVGRIKSKTDGGTRDYAAPVK<br>GRFTISRDDSKNTLYLQMNSLKTEDTAVYYCTTGYGEGYWGQGTLVTVSS (SEQ ID NO: 131)<br>22D04A HC CDR1 GFTFSNAW (SEQ ID NO: 132)<br>22D04A HC CDR2 IKSKTDGGTR (SEQ ID NO: 133)<br>22D04A HC CDR3 TTGYGEGY (SEQ ID NO: 134) |
| 22H10A | 22H10A VH<br>EMQLVESGGGLVKPGGSLRLSCAASGFTFSSYSMNWVRQAPGKGLEWVSSISTRKNYIYYADSVQGR<br>FIFSRDNAKNALYLQMNSLRAEDSAVYYCTRGGYIRSPNAFDIWGQGTMVTVSS (SEQ ID NO: 141)<br>22H10A HC CDR1 GFTFSSYS (SEQ ID NO: 142)<br>22H10A HC CDR2 ISTRKNYI (SEQ ID NO: 143)<br>22H10A HC CDR3 TRGGYIRSPNAFDI (SEQ ID NO: 144) |

TABLE 3

Sequences of the LC variable region (VL) of 15 mAbs. CDRs 1-3 of
each LC variable region is underlined in the
complete VL amino acid sequence, where the
CDRs were identified using IMGT numbering.
Each CDR is also listed separately and
identified by SEQ ID NO: assigned to the CDR.

| mAb name | LC variable region sequence, CDRs underlined in complete VL amino acid sequence |
|---|---|
| 06E17A | 06E17A VL<br>QSVLTQPPSASGTPGQRVTISCSGSSSNIKSNTVNWYQQLPGTAPKLLIYRNNQRPSGVPDRESGSK<br>SGTSASLAISGLQSEDEADYYCAAWDDSLKGVVFGGGTDLTVL (SEQ ID NO: 6)<br>06E17A LC CDR1 SSNIKSNT (SEQ ID NO: 7)<br>06E17A LC CDR2 RNN<br>06E17A LC CDR3 AAWDDSLKGVV (SEQ ID NO: 9) |
| 15M13A | 15M13A VL<br>QSVLTQPPSVSAAPGQKVTISCSGSSSNIGNHYVSWYQQLPGTAPKLLIYDNNKRPSGIPDRESGSK<br>SGTSATLGITGLQTGDEADYYCGTWDTSLSAVVFGGGTKLTVL (SEQ ID NO: 16)<br>15M13A LC CDR1 SSNIGNHY (SEQ ID NO: 17)<br>15M13A LC CDR2 DNN<br>15M13A LC CDR3 GTWDTSLSAVV (SEQ ID NO: 19) |
| 17D08A | 17D08A VL<br>QSVLTQPPSVSAAPGQKVTISCSGYSSNIGNHYVSWYQQLPGTAPKFFIYDNNKRPSGIPDRESGSK<br>SGTSATLGITGLQTGDEADYYCGTWDSSLITYVFGTGTKVTVL (SEQ ID NO: 26)<br>17D08A LC CDR1 SSNIGNHY (SEQ ID NO: 27)<br>17D08A LC CDR2 DNN<br>17D08A LC CDR3 GTWDSSLITYV (SEQ ID NO: 29) |
| 17H05A | 17H05A VL<br>QSVLTQPPSVSAAPGQKVTISCSGSSSNIGNYYVSWYQQLPGTAPKLLIYDNHKRPSGIPDRESGSK<br>SGTSATLGITGLQTGDEADYYCGTWDSSLSAVVFGGGTKLTVL (SEQ ID NO: 36)<br>17H05A LC CDR1 SSNIGNYY (SEQ ID NO: 37)<br>17H05A LC CDR2 DNH<br>17H05A LC CDR3 GTWDSSLSAVV (SEQ ID NO: 39) |

TABLE 3-continued

Sequences of the LC variable region (VL) of 15 mAbs. CDRs 1-3 of
each LC variable region is underlined in the
complete VL amino acid sequence, where the
CDRs were identified using IMGT numbering.
Each CDR is also listed separately and
identified by SEQ ID NO: assigned to the CDR.

mAb name | LC variable region sequence, CDRs underlined in complete VL amino acid sequence 17P04A 17P04A VL
QTVVTQE PSLTVSPGGTVTLTCASSTGAVTSDYYPNWFQQKPGQAPRALIYSASTKHSWTPARFSGS
LLGGKAALTLSGVQPEDEADYYCLLYYGGAWVFGGGTKLTVL (SEQ ID NO: 46)
17P04A LC CDR1 TGAVTSDYY (SEQ ID NO: 47)
17P04A LC CDR2 SAS
17P04A LC CDR3 LLYYGGAWV (SEQ ID NO: 49)

18F06A 18F06A VL
QSVLTQPPSVSAAPGQKVTISCSGSSSNIGNYYVSWYQQLPGTAPKLLIYDNNKRPSGIPDRFSASK
SGTSATLGITGLQTGDEADYYCGTWDDSLSAVVFGGGTKLTVL (SEQ ID NO: 56)
18F06A LC CDR1 SSNIGNYY (SEQ ID NO: 57)
18F06A LC CDR2 DNN
18F06A LC CDR3 GTWDDSLSAVV (SEQ ID NO: 59)

18P01A 18P01A VL
QSVLTQPPSVSAAPGQKVTISCSGSSSNIGNHYVSWYQQLPGTAPKFFIYDNSKRPSGIPDRESGSK
SGTSATLGITGLQTGDEADYYCGTWDSSLSTYVFGTGTKVTVL (SEQ ID NO: 66)
18P01A LC CDR1 SSNIGNHY (SEQ ID NO: 67)
18P01A LC CDR2 DNS
18P01A LC CDR3 GTWDSSLSTYV (SEQ ID NO: 69)

20O07A 20O07A VL
QSVLTQPPSVSAAPGQKVTISCSGSSSNIGNHYVSWYQQLPGTAPKFLIYDNSKRPSGIPDRESGSK
SGTSATLGITGLQTGDEADYYCGTWDSSLSTYFFGTGTKVTVL (SEQ ID NO: 76)
20O07A LC CDR1 SSNIGNHY (SEQ ID NO: 77)
20O07A LC CDR2 DNS
20O07A LC CDR3 GTWDSSLSTYF (SEQ ID NO: 79)

20O11A 20O11A VL
QSVLTQPPSVSAAPGQKVTISCSGSSSNIGNHYVSWYQQLPGTAPKLLIYDNNKRPSGIPDRESGSK
SGTSATLGITGLQTGDEADYYCGTWDSSLGAVLFGGGTKLTVL (SEQ ID NO: 86)
20O11A LC CDR1 SSNIGNHY (SEQ ID NO: 87)
20O11A LC CDR2 DNN
20O11A LC CDR3 GTWDSSLGAVL (SEQ ID NO: 89)

21F12A 21F12A VL
QSVLTQPPSVSAAPGQKVTISCSGSSSNIGNYYVSWYQQLPGTAPKLLIYDNNKRPSGIPDRESGSK
SGTSATLGITGLRTGDEADYYCGTWDSSLSAVVFGGGTKLTVL (SEQ ID NO: 96)
21F12A LC CDR1 SSNIGNYY (SEQ ID NO: 97)
21F12A LC CDR2 DNN
21F12A LC CDR3 GTWDSSLSAVV (SEQ ID NO: 99)

21G10A 21G10A VL
QSVLTQPPSVSAAPGQKVTISCSGSSSNIGNYYVSWYQQLPGTAPKLLIYDNNKRPSGIPDRESGSK
SGTSATLGITGLQTGDEADYYCGTWDSSLSAVVFGGGTKLTVL (SEQ ID NO: 106)
21G10A LC CDR1 SSNIGNYY (SEQ ID NO: 107)
21G10A LC CDR2 DNN
21G10A LC CDR3 GTWDSSLSAVV (SEQ ID NO: 109)

21K12A 21K12A VL
QSVLTQPPSASGTPGQRVTISCSGSSSNIKSNTVNWYQQLPGTAPKLLIYRNNQRPSGVPDRESGSK
SGTSASLAISGLQSEDEADYYCAAWDDSLKGVVFGGGTDLTVL (SEQ ID NO: 116)
21K12A LC CDR1 SSNIKSNT (SEQ ID NO: 117)
21K12A LC CDR2 RNN
21K12A LC CDR3 AAWDDSLKGVV (SEQ ID NO: 119)

21P22A 21P22A VL
QSVLTQPPSASGTPGQRVTISCSGSSSNIKSNTVNWYQQLPGTAPKLLIYRNNQRPSGVPDRESGSK
SGTSASLAISGLQSEDEADYYCAAWDDSLKGVVFGGGTDLTVL (SEQ ID NO: 126)
21P22A LC CDR1 SSNIKSNT (SEQ ID NO: 127)
21P22A LC CDR2 RNN
21P22A LC CDR3 AAWDDSLKGVV (SEQ ID NO: 129)

22D04A 22D04A VL
QSVLTQPPSASGTPGQRVTISCSGSSSNIKSNTVNWYQQLPGTAPKLLIYRNNQRPSGVPDRESGSK
SGTSASLAISGLQSEDEADYYCAAWDDSLKGVVFGGGTDLTVL (SEQ ID NO: 136)
22D04A LC CDR1 SSNIKSNT (SEQ ID NO: 137)
22D04A LC CDR2 RNN
22D04A LC CDR3 AAWDDSLKGVV (SEQ ID NO: 139)

TABLE 3-continued

Sequences of the LC variable region (VL) of 15 mAbs. CDRs 1-3 of
each LC variable region is underlined in the
complete VL amino acid sequence, where the
CDRs were identified using IMGT numbering.
Each CDR is also listed separately and
identified by SEQ ID NO: assigned to the CDR.

| mAb name | LC variable region sequence, CDRs underlined in complete VL amino acid sequence |
|---|---|
| 22H10A | 22H10A VL<br>QTVVTQEPSLTVSPGGTVTLTCAS<u>STGTVTSGYF</u>PNWLQQKPGQAPRALIY<u>SIN</u>NKHEWTPARFSGS<br>LLGGKAALTLSGVQPEDEAEYYC<u>LLYYGGAWV</u>EGGGTKLTVL (SEQ ID NO: 146)<br>22H10A LC CDR1 TGTVTSGYF (SEQ ID NO: 147)<br>22H10A LC CDR2 SIN<br>22H10A LC CDR3 LLYYGGAWV (SEQ ID NO: 149) |

Example 4: Characterization of Lead Antibodies

Detailed profiles of the 5 lead mAbs 18P01A, 17P04A, 20O07A, 22D04A, and 06E17A were developed and are described below.

Affinity for Aβ Peptide in Direct ELISA

Figure 5A:
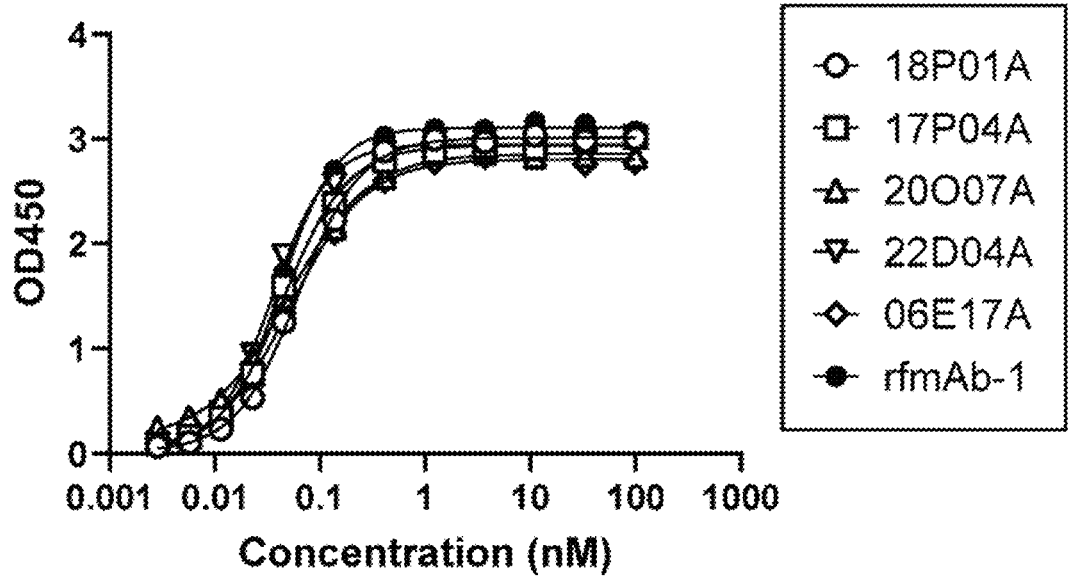
FIGS. 5A-5B show results for the 5 lead antibodies 18P01A, 17P04A, 20O07A, 22D04A, 06E17A, and reference antibody rfmAb-1 in direct ELISA. Aβ$_{1-42}$ (FIG. 5A) or Aβ$_{p3-42}$ (FIG. 5B) were coated on wells of an ELISA plate at 50 pmol per well. Diluents of antibodies were then applied to the plate. Binding was detected by HRP-labeled secondary antibody and TMB substrate.
Figure 5B:
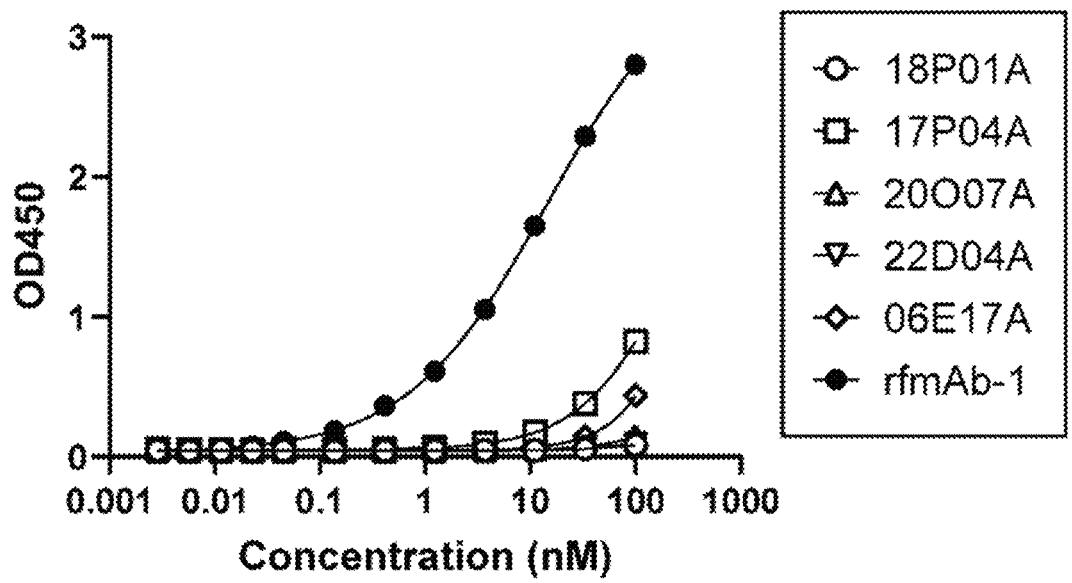
Figure 6A:
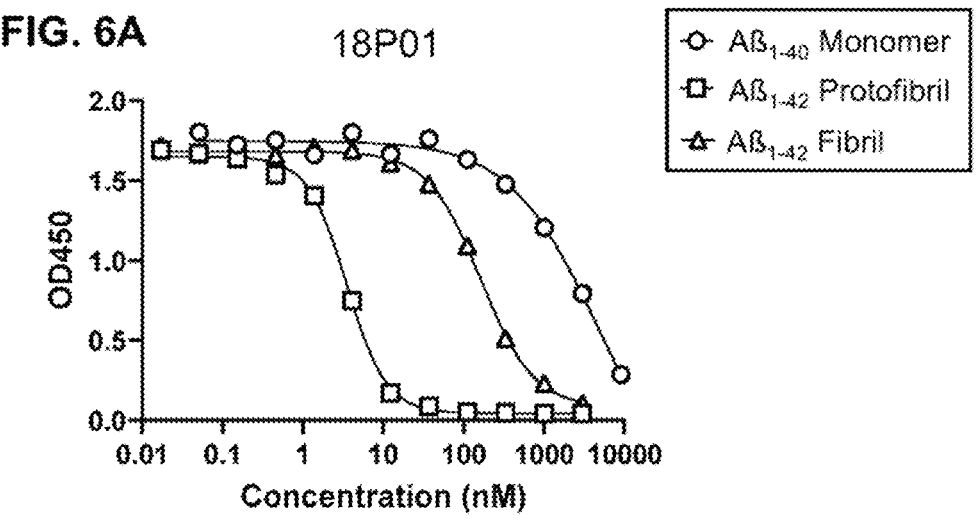
FIGS. 6A-6E show results for the 5 lead antibodies in competitive ELISA. Each antibody was pre-incubated with diluents of Aβ monomer (Aβ$_{1-40}$ monomers), Aβ protofibril (Aβ$_{1-42}$ protofibrils), or Aβ fibril (Aβ$_{1-42}$ fibrils) for 1 h. The antibody-Aβ mixture was then applied to an ELISA plate coated with Aβ monomer for 10 min and binding was detected by HRP-labeled secondary antibody and TMB substrate. Results are shown for each antibody for Aβ monomer (Aβ$_{1-40}$ monomers, open circles), Aβ protofibril (Aβ$_{1-42}$ protofibrils, open squares), Aβ fibril (Aβ$_{1-42}$ fibrils, open triangles), with FIG. 6A showing results for antibody 18P01A, FIG. 6B showing results for antibody 17P04A, FIG. 6C showing results for antibody 20O07A, FIG. 6D showing results for antibody 22D04A, and FIG. 6E showing results for antibody 06E17A.
Figure 6B:
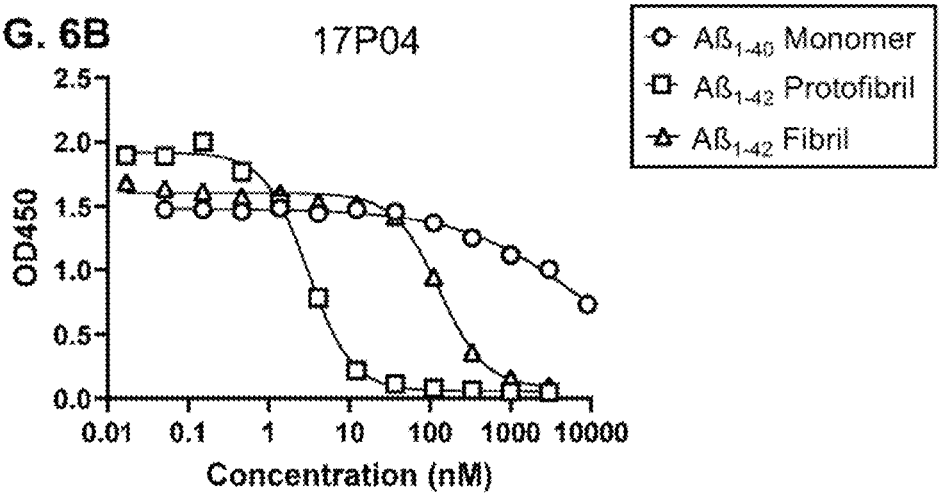
Figure 6C:
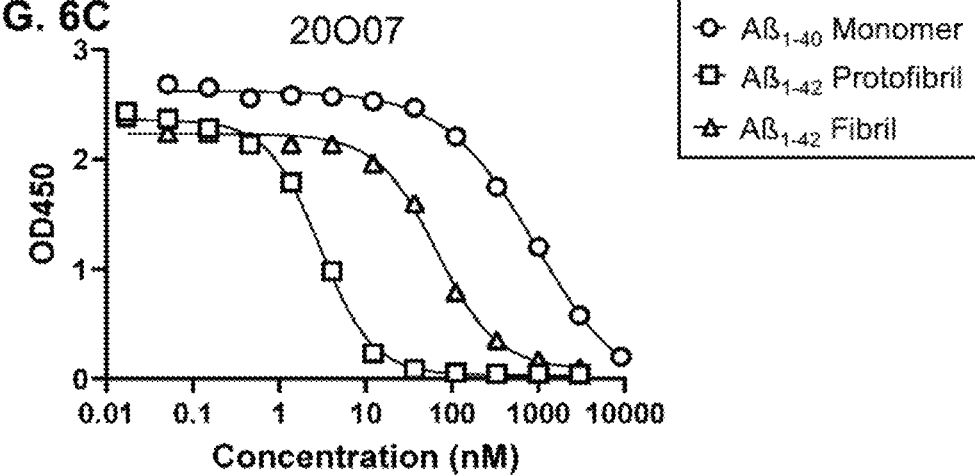
Figure 6D:
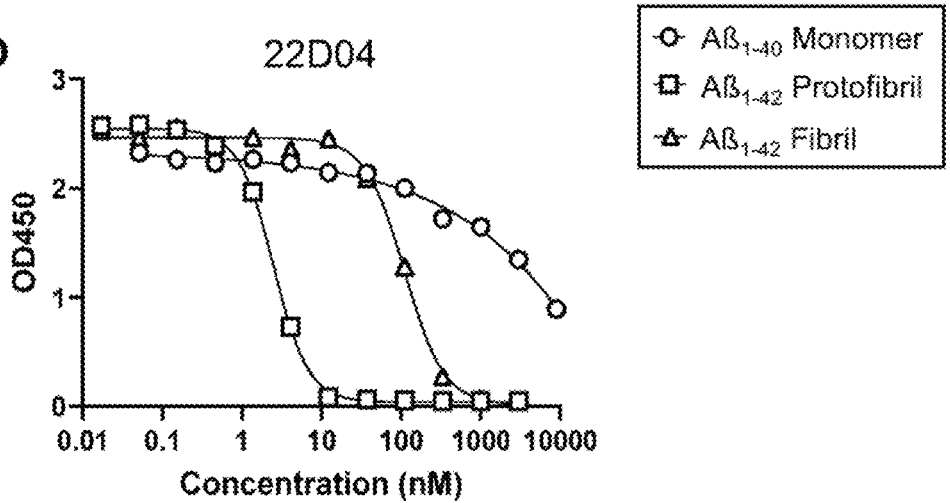
Figure 6E:
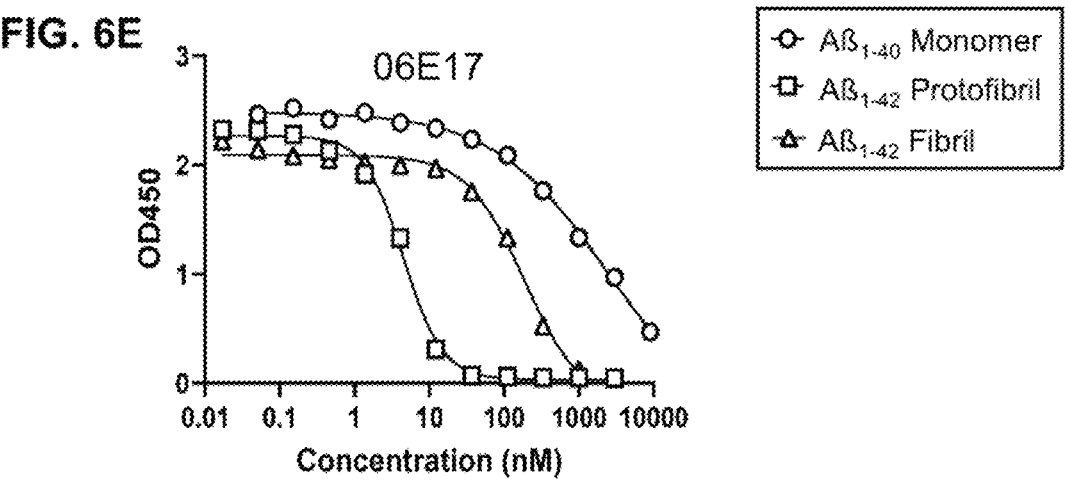

Direct ELISA was used to test each antibody's affinity for $A\beta_{1-42}$ and pyroglutamate-modified Aβ ($A\beta_{p3-42}$). Plates were coated with 0.5 UM of $A\beta_{1-42}$ (rPeptide, A-1167-2) or $A\beta_{p3-42}$ (AnaSpec, AS-29907-01) for 2 h at 4° C. Diluents of antibodies (3-fold serial dilutions with concentrations in the range of 0-100 nM) were added to the plate for 1 h at RT. Binding of antibody to immobilized Aβ on each plate was detected by HRP-labeled secondary antibody and TMB substrate, as described in Example 2. All 5 lead antibodies showed strong binding to $A\beta_{1-42}$ with a calculated $EC_{50}$<0.1 nM (FIG. 5A and Table 1), but showed weak binding to $A\beta_{p3-42}$ with a calculated $EC_{50}$>50 nM (FIG. 5B and Table 1).

Selectivity for Different Aβ Conformations in Competitive ELISA

Competitive ELISA was used to evaluate the relative affinities of antibodies for Aβ monomer, Aβ protofibril and Aβ fibril. The antibodies were subjected to monomer, protofibril or fibril competition on monomer coated plates. Antibodies were pre-incubated with diluents of Aβ monomer or Aβ protofibril or Aβ fibril (3-fold serial dilutions with a starting concentration of 3000 nM) for 1 h at 4° C. The concentration of Aβ antibody used in the antibodies-Aβ mixture was the $EC_{90}$ of that antibody with Aβ monomers in the direct ELISA. The antibody-Aβ mixture was then applied to an ELISA plate coated with 0.5 µM Aβ monomer for 10 min at RT. The binding was detected by HRP-labeled secondary antibody and TMB substrate, as described in Example 2. All 5 lead antibodies have high affinities for protofibril and low affinities for monomer in competitive ELISA (FIG. 6 and Table 1). The ratios of $IC_{50}$ monomer to $IC_{50}$ protofibril were >300-fold for all 5 antibodies and >1000-fold for 18P01 and 17P04. The affinities of the 5 antibodies for fibril were higher than the affinities for monomer but lower than that for protofibril Due to the low affinities of the antibodies for monomers, the $IC_{50}$ monomer in the competitive ELISA was not a reliable value. We further tested the 5 antibodies in capture ELISA to get their accurate affinities for monomer.

Affinities for Aβ Monomer in Capture ELISA

Figure 7:
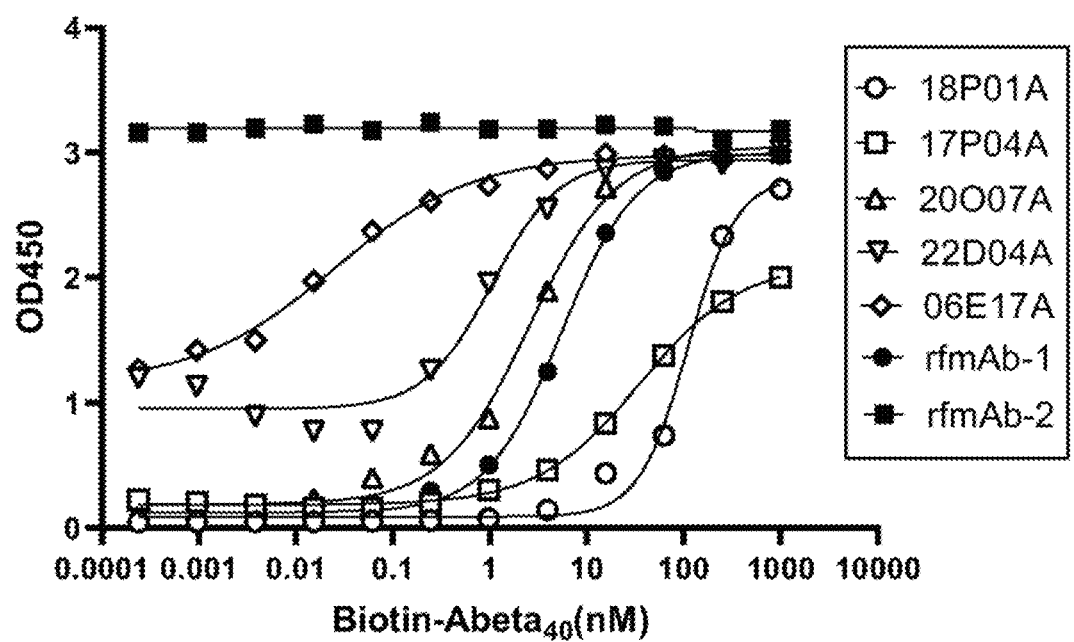
FIG. 7 shows results from capture of soluble biotin-Aβ monomer with immobilized antibodies (0.5 μg per well), for each of the 5 lead antibodies 18P01A (open circle), 17P04A (open square), 20O07A (upward-pointing triangle), 22D04A (downward-pointing triangle), and 06E17A (open diamond), and for the two reference antibodies rfmAb-1 having low affinity for monomer (solid circle) and rfmAb-2 having high affinity for monomer (solid square).

Capture ELISA can accurately measure the affinities of antibodies for Aβ monomer. A 96-well plate was coated with 5 µg/mL of antibodies overnight at RT. The plate was then treated with diluents of biotin-labelled $A\beta_{1-40}$ monomers (AnaSpec, AS-61483-01, 4-fold serial dilutions with concentrations in the range of 0-1000 nM) for 1 h at RT. The binding of biotin-labelled $A\beta_{1-40}$ monomers with immobilized antibody was detected by HRP-conjugated streptavidin and TMB, as described in Example 2. The EC50 of antibodies to Aβ monomer (EC50 monomer) was determined in this assay (FIG. 7 and Table 1). The ratio of EC50 monomer in the capture ELISA to IC50 oligomer in the competitive ELISA was then calculated. This ratio reflects the selectivity of antibodies for Aβ protofibril over Aβ monomer and was used to rank the antibodies as shown in Table 1.

Antibody-Dependent Cell-Mediated Phagocytosis (ADCP)

Figure 8:
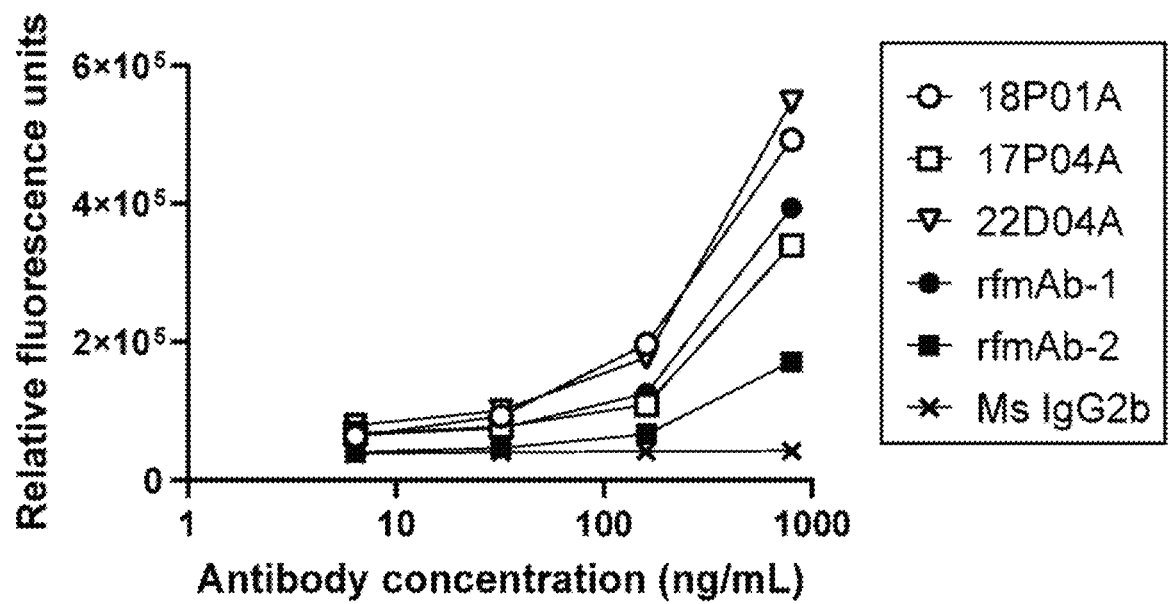
FIG. 8 shows results from an ADCP assay using BV2 microglial cells, for antibodies 18P01A (open circle), 17P04A (open square), 22D04A (downward-pointing triangle), rfmAb-1 (solid circle), rfmAb-2 (solid square), and mouse IgG2b as a negative control (cross). HILYTE™ 488-labeled protofibrils (2.25 μg/mL) were mixed with serial dilutions (800, 160, 32, 6.4 ng/ml) of antibodies for 30 min. Each mixture was added to BV-2 and incubated at 37 degrees C. for 1.5 h to induce ADCP. Positive fluorescence signals rendered by HILYTE™ 488 labeled protofibrils that were ingested were analyzed by flow cytometry and relative fluorescence values were calculated.

In accordance with the non-limiting hypothesis that anti-Aβ antibody can clear toxic Aβ protofibrils/plaque in brain by inducing ADCP of Aβ in microglia, the ability of lead antibodies to mediate the phagocytosis of Aβ protofibril by microglia was evaluated with HILYTE™ 488 labeled Aβ protofibrils and murine microglia cell line BV-2 cells. HILYTE™ 488 labeled Aβ 1-42 monomers were mixed with unlabeled $A\beta_{1-42}$ monomers at a 1:5 ratio, and incubated at 37° ° C. for 2 h to form HILYTE™ 488 labelled protofibrils, followed by purification by SEC separation and collection of the protofibril peak. BV-2 cells were seeded to 96-well cell culture plates at a density of 60,000 cells per well and incubated overnight. The BV-2 cells were then pre-treated with ADCP assay diluent (DMEM/F12 with HEPES media, 1% BSA, and 100 µg/mL Fucoidan) for 1 h before the ADCP assay. Next, 2.25 µg/mL of HILYTE™ 488 labeled Aβ oligomers were mixed with serial dilutions (800, 160, 32, and 6.4 ng/ml) of each of the lead antibodies or mouse IgG2b (negative control) in ADCP assay diluent for 30 min. The mixture of HILYTE™ 488 labeled Aβ protofibrils and antibodies was added to BV-2 cells and incubated at 37° C. for 1.5 h to induce ADCP. Cell-surface bound oligomer-antibody complex was removed by treatment with 0.25% trypsin for 20 min at 4° C. Cells were transferred to a conical bottom 96-well plate, rinsed twice with ice cold cell staining buffer (BioLegend #420201), fixed for 20 min in ice cold fixation buffer (BioLegend #420801), and washed once again. Finally, cells were analyzed by flow cytometry for positive FITC signals, which proportionally reflected the amount of HILYTE™ 488 labeled Aβ protofibrils that BV-2 cells had taken up (FIG. 8). Raw RFU (relative fluorescence unit) values were used to report ADCP response (Table 1), and the ability of each lead antibody candidate to trigger ADCP can be evaluated relative to ADCP response of rfmAb-1. Antibodies 18P01A, 17P04A, 20O07A, 22D04A, and 06E17A had relative ADCP of 1.36, 0.79, 1.05, 1.39, and 0.95, respectively.

Example 5: Reformatting and Recombinant Expression

Reformatting as Fully Human Antibodies

The 5 lead antibodies 18P01A, 17P04A, 20O07A, 22D04A, and 06E17A were originally isolated from hybridoma supernatants, subcloned, and purified as described in Example 1, yielding chimeric monoclonal antibodies having human F(ab')$_2$ and mouse IgG1 CH2 and CH3 domains (i.e., chimeric human F(ab')$_2$/mouse IgG1 antibodies as described above). As shown in Tables 2 and 3: 18P01A has the heavy chain variable region (VH) amino acid sequence of SEQ ID NO:61, and the light chain variable region (VL) amino acid sequence of SEQ ID NO: 66; 17P04A has the VH amino acid sequence of SEQ ID NO: 41 and the VL amino acid sequence of SEQ ID NO: 46; 20O07A has the VH amino acid sequence of SEQ ID NO: 71 and the VL amino acid sequence of SEQ ID NO: 76; 22D04A has the VH amino acid sequence of SEQ ID NO: 131 and the VL amino acid sequence of SEQ ID NO: 136; and 06E17A has the VH amino acid sequence of SEQ ID NO: 1 and the VL amino acid sequence of SEQ ID NO: 6. The original chimeric lead antibodies can be identified as 18P01A (mIgG1), 17P04A (mIgG1), 20O07A (mIgG1), 22D04A (mIgG1), and 06E17A (mIgG1), as in Tables 4 and 5.

Each of the 5 original chimeric human F(ab')$_2$/mouse IgG1 lead antibodies was then reformatted to fully human IgG1 lambda by replacing the heavy chain constant region of each antibody with a human IgG1 heavy chain constant region including CH1, hinge region, CH2 and CH3 through de novo gene synthesis. Thus, the heavy chain (HC) amino acid sequence of each reformatted fully human antibody includes the VH amino acid sequence (including HC CDRs 1-3) of the source mAb, and the light chain (LC) amino acid sequence of each reformatted fully human includes the VL amino acid sequence (including the LC CDRs 1-3) of the source mAb.

Fully human antibody 18P01A(hIgG1) has the HC amino acid sequence of SEQ ID NO: 157 including the 18PO1A VH amino acid sequence of SEQ ID NO: 61, and the LC amino acid sequence of SEQ ID NO: 158 including the 18PO1A VL amino acid sequence of SEQ ID NO: 66. Fully human antibody 17P04A(hIgG1) has the HC amino acid sequence of SEQ ID NO: 153 including the 17P04A VH amino acid sequence of SEQ ID NO: 41, and the LC amino acid sequence of SEQ ID NO: 154 including the 17P04A VL amino acid sequence of SEQ ID NO: 46. Fully human antibody 20O07A(hIgG1) has the HC amino acid sequence of SEQ ID NO: 161 including the 20O07A VH amino acid sequence of SEQ ID NO: 71, and the LC amino acid sequence of SEQ ID NO: 162 including the 20O07A VL amino acid sequence of SEQ ID NO: 76. Fully human antibody 22D04A(hIgG1) has the HC amino acid sequence of SEQ ID NO: 165 including the 22D04A VH amino acid sequence of SEQ ID NO: 131, and the LC amino acid sequence of SEQ ID NO: 166 including the 22D04A VL amino acid sequence of SEQ ID NO: 136. Fully human antibody 06E17A(hIgG1) has the HC amino acid sequence of SEQ ID NO: 169 including the 06E17A VH amino acid sequence of SEQ ID NO: 1, and the LC amino acid sequence of SEQ ID NO: 169 including the 06E17A VL amino acid sequence of SEQ ID NO: 6.

The reformatted fully human antibodies were expressed in CHO cells via transient transfection using EXPICHO™ expression system, and purified using a Protein A column. The purified fully human antibodies were then tested in a series of in vitro assays including direct ELISA, competitive ELISA, and capture ELISA, and the results were compared with the original chimeric antibodies having human F(ab')$_2$/mouse IgG1CH2-CH3. Results are illustrated in Table 4.

For the 17P04A, 20O07A, 22D04A, and 06E17A antibodies, there was no difference in their profiles between the fully human version and the original chimeric human F(ab')$_2$/mouse IgG1 version. However, fully human 18P01A showed dramatically reduced affinity for Aβ in all three conformations tested by competitive ELISA. Results from direct ELISA showed that the EC$_{50}$ Aβ 1-42 for fully human 18P01A increased >800 fold to a value of 49.96 nM, compared to 0.062 mM for the original chimeric 18P01A.

TABLE 4

Comparison of the anti-AB antibodies in fully human version and in mouse IgG1/human chimeric version. UND, undetermined value.

| | Direct ELISA | | Competitive ELISA | | | Capture ELISA | |
|---|---|---|---|---|---|---|---|
| Monoclonal Antibody Names | EC$_{50}$ Abeta 1-42 (nM) | EC$_{50}$ Abeta p3-42 (nM) | IC$_{50}$ oligomer (nM) | IC$_{50}$ monomer (nM) | IC$_{50}$ fibril (nM) | EC$_{50}$ monomer (nM) | EC$_{50}$ monomer/ IC$_{50}$ oligomer |
| Chimeric mouse 18P01A (mIgG1) | 0.062 | 57.6 | 3.5 | 4601 | 163 | 67.0 | 19.094 |
| Fully human 18P01A (hIgG1) | 49.960 | 196.0 | UND | UND | UND | 916.7 | UND |
| Chimeric mouse 17P04A (mIgG1) | 0.045 | 202.6 | 3.1 | 8433 | 130 | 35.2 | 11.511 |
| Fully human 17P04A (hIgG1) | 0.062 | 38.7 | 2.5 | 716 | 174 | 33.8 | 13.319 |
| Chimeric mouse 20O07A (mIgG1) | 0.050 | 335.8 | 3.0 | 935 | 67 | 2.57 | 0.861 |
| Fully human 20O07A (hIgG1) | 0.086 | UND | 4.3 | 586 | 88 | 4.57 | 1.068 |
| Chimeric mouse 22D04A (mIgG1) | 0.035 | 51.2 | 2.5 | UND | 111 | 1.0 | 0.421 |

TABLE 4-continued

Comparison of the anti-AB antibodies in fully human version and in mouse IgG1/human chimeric version. UND, undetermined value.

|  | Direct ELISA | | Competitive ELISA | | | Capture ELISA | |
| --- | --- | --- | --- | --- | --- | --- | --- |
|  | EC$_{50}$ | EC$_{50}$ | | | | | |
| Monoclonal Antibody Names | Abeta 1-42 (nM) | Abeta p3-42 (nM) | IC$_{50}$ oligomer (nM) | IC$_{50}$ monomer (nM) | IC$_{50}$ fibril (nM) | EC$_{50}$ monomer (nM) | EC$_{50}$ monomer/ IC$_{50}$ oligomer |
| Fully human 22D04A | 0.065 | 18.5 | 2.5 | 16038 | 168 | 0.2 | 0.089 |
| Chimeric mouse 06E17A (mIgG1) | 0.052 | UND | 4.5 | 2579 | 39 | 0.02 | 0.005 |
| Fully human 06E17A | 0.062 | 321.1 | 3.0 | 1718 | 359 | 0.15 | 0.051 |

Reformatting as Human F(Ab')$_2$/Mouse IgG2a CH2-CH3 Chimeric Antibodies

Converting a mAb from mouse IgG1 to mouse IgG2a may enhance its ADCP activity. To test effects on ADCP, the original lead antibodies 18P01A, 17P04A, 20O07A, 22D04A, and 06E17A were reformatted from the original mouse IgG1/human chimeric version (mouse IgG1/human F(ab')$_2$) to a mouse IgG2a/human chimeric version (mouse IgG2a CH2-CH3/human F(ab')$_2$) for animal studies. Reformatted antibody 18P01A(mIgG2a) has the heavy chain (HC) amino acid sequence of SEQ ID NO: 155 including the 18P01A VH amino acid sequence of SEQ ID NO: 61, and the LC amino acid sequence of SEQ ID NO: 156 including the 18P01A VL amino acid sequence of SEQ ID NO: 66. Reformatted antibody 17P04A(mIgG2a) has the HC amino acid sequence of SEQ ID NO: 151 including the 17P04A VH amino acid sequence of SEQ ID NO: 41, and the LC amino acid sequence of SEQ ID NO: 152 including the 17P04A VL amino acid sequence of SEQ ID NO: 46. Reformatted antibody 20O07A(mIgG2a) has the HC amino acid sequence of SEQ ID NO: 159 including the 20O07A VH amino acid sequence of SEQ ID NO: 71, and the LC amino acid sequence of SEQ ID NO: 160 including the 20O07A VL amino acid sequence of SEQ ID NO: 76. Reformatted antibody 22D04A(mIgG2a) has the HC amino acid sequence of SEQ ID NO: 163 including the 22D04A VH amino acid sequence of SEQ ID NO: 131, and the LC amino acid sequence of SEQ ID NO: 164 including the 22D04A VL amino acid sequence of SEQ ID NO: 136. Reformatted antibody 06E17A(mIgG2a) has the HC amino acid sequence of SEQ ID NO: 167 including the 06E17A VH amino acid sequence of SEQ ID NO: 1, and the LC amino acid sequence of SEQ ID NO: 168 including the 06E17A VL amino acid sequence of SEQ ID NO: 6.

Reformatted antibody 17P04A(mIgG2a) and reformatted antibody 18P01A(mIgG2a) were recombinantly expressed and purified at large scale. Antibody 17P04A(mIgG2a) and antibody 18P01A(mIgG2a) were then tested in a series of assays including direct ELISA, competitive ELISA, capture ELISA, and ADCP. Compared to the original human F(ab')$_2$/mouse IgG1 chimeric antibodies, no significant difference was observed with the human F(ab')$_2$/mouse IgG2a CH2-CH3 chimeric version in terms of selectivity for different Aβ conformations and ability to induce ADCP (Table 5).

TABLE 5

Comparison of 17P04A and 18P01A in original human F(ab')$_2$/mouse IgG1 chimeric version and in reformatted human F(ab')$_2$/mouse IgG2a CH2-CH3 version. UND, undetermined value.

|  | Direct ELISA | | Competitive ELISA | | | Capture ELISA | | |
| --- | --- | --- | --- | --- | --- | --- | --- | --- |
|  | EC$_{50}$ | EC$_{50}$ | | | | | | |
| Monoclonal Antibody Names | Abeta 1-42 (nM) | Abeta p3-42 (nM) | IC$_{50}$ oligomer (nM) | IC$_{50}$ monomer (nM) | IC$_{50}$ fibril (nM) | EC$_{50}$ monomer (nM) | EC$_{50}$ monomer/ IC$_{50}$ oligomer | ADCP (RFU) |
| Original 18P01A (mIgG1) | 0.062 | 57.6 | 3.5 | 4601.0 | 162.8 | 67.0 | 19.094 | 673053 |
| Reformatted 18P01A (mIgG2a) | 0.087 | UND | 27.5 | 4236.0 | 700 | 248.0 | 9.018 | 488095 |
| Original 17P04A (mIgG1) | 0.045 | 202.6 | 3.1 | 8433.0 | 130 | 35.2 | 11.511 | 328327 |
| Reformatted 17P04A (mIgG2a) | 0.057 | 19.4 | 1.6 | 2024.0 | 158 | 59.0 | 36.875 | 375215 |

Example 6: Pharmacokinetics of 17P04A and 18P01A in Mice

Figure 9:
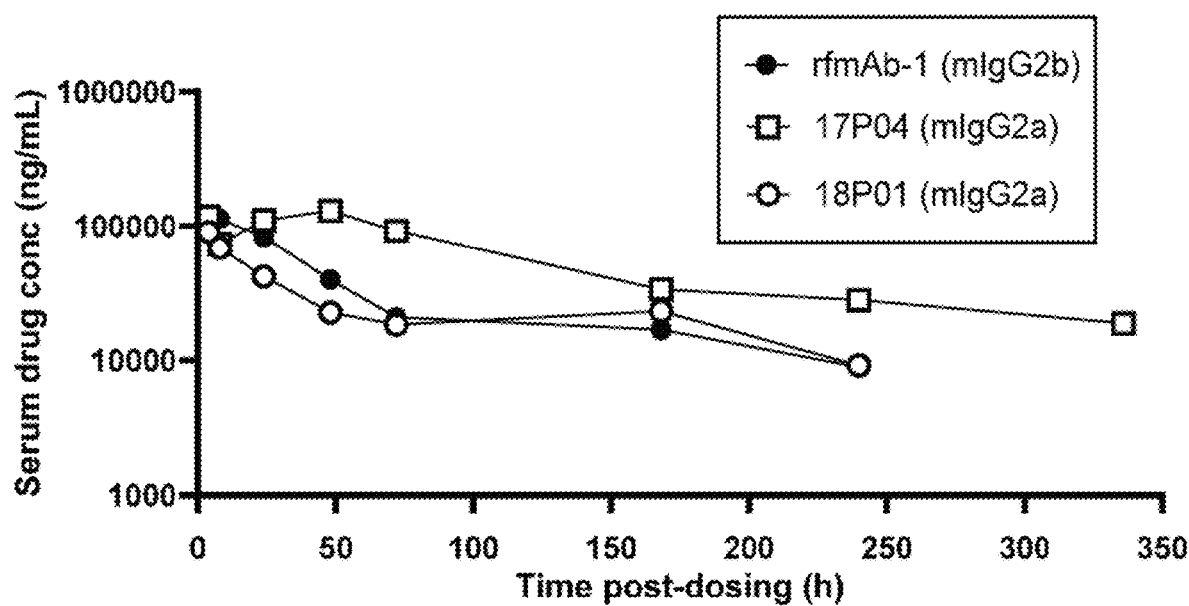
FIG. 9 shows PK data in serum for antibody 17P04A (open square), antibody 18P01A (open circle), and rfmAb-1 (solid circle) in the serum of B6SJLF1 mice. Values at each time point were the average values of the samples from 2-3 animals. Table shows calculated PK parameters for each antibody in serum.
Figure 10:
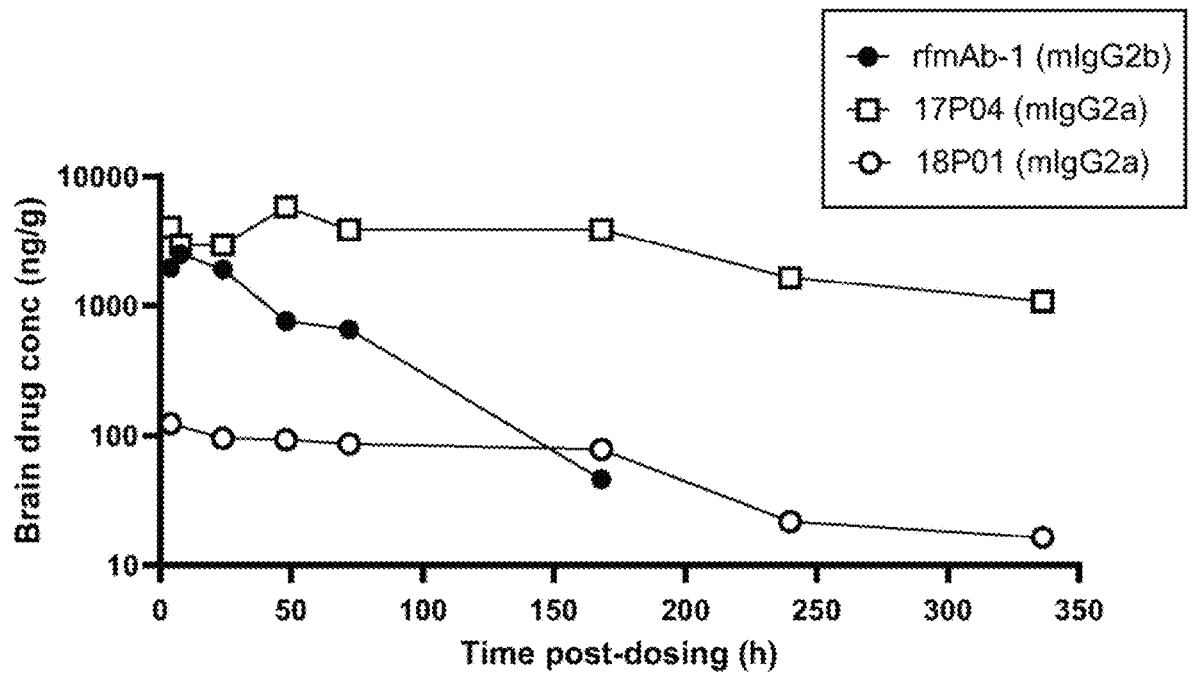
FIG. 10 shows PK data in brain for antibody 17P04A (open square), antibody 18P01A (open circle), and rfmAb-1 (solid circle) in the brain of B6SJLF1 mice. Values at each time point were the average values of the samples from 2-3 animals. Table shows calculated PK parameters for each antibody in brain.

17P04A and 18P01A in the human F(ab')$_2$/mouse IgG2a CH2-CH3 chimeric version as 17P04A(mIgG2a) and 18P01A(mIgG2a) were selected for pharmacokinetic studies based on high levels of preferential binding to Aβ protofibril and ability to trigger ADCP. Antibodies 17P04A(mIgG2a)

and 18P01A(mIgG2a) were injected intraperitoneally (ip) in B6SJLF1 mice (The Jackson Laboratory, JAX #100012, jax.org; MPD ID: 178, phenome.jax.org/strains/178) at a dose of 10 mg/kg. For use as a control, rfmAb-1 as rfmAB01 (mIgG2b) was also administered ip at the same dose to a group of B6SJLF1 mice (The Jackson Laboratory, JAX #100012). Serum and brain tissue were collected at 4, 8 hours, 1, 2, 3, 7, 10, and 14 days after the injection. Whole-animal perfusion with PBS was performed before the brain tissue collection. Brain tissue was homogenized in 3 volumes (300 μL per 100 mg tissue) of Tris-Buffered Saline (TBS) with protease inhibitor cocktail (Thermo Fisher Scientific, 78429; thermofisher.com) using BULLET BLENDER® 5E Gold (Next Advance, BB5E-AU) with zirconium oxide beads (Next Advance, PINK5E100). Homogenate was transferred to a 2 mL tube and centrifuged at 16,000×g for 20 min at 4° C. to remove the pellet. Whole blood was allowed to clot at room temperature for 30 min before centrifuging and collecting the separate serum. Drug concentration in the supernatant of the brain homogenate and serum was measured by direct ELISA with $A\beta_{1-42}$ peptides as the coated antigen. Plates were coated with 0.5 μM of $A\beta_{1-42}$ (rPeptide, A-1167-2; rpeptide.com) overnight at 4° C., washed 3 times with TBST, and blocked with protein-free blocking buffer (Thermo Fisher 37572) for 1 h at RT. Diluents of brain homogenate (2-fold series dilutions with an initial dilution of 1:4, triplicate per concentration) or serum (2-fold series dilutions with an initial dilution of 1:200, triplicate per concentration) were applied to the plate for 1 h at RT. Binding of antibody in brain homogenate or in serum to immobilized $A\beta_{1-42}$ was detected by HRP-labeled secondary antibody and TMB substrate, as described in the direct ELISA protocol in Example 2. Non-compartmental pharmacokinetics (PK) analysis was conducted via an online PK calculator (Noncompartmental Pharmacokinetics Analysis calculator available at dash.gallery/dash-pk-calc/). The half-life of rfmAb-1(mIgG2a), 17P04A (mIgG2a), and 18P01A(mIgG2a) in serum was 140.9, 199.7, and 183.2 h, respectively (FIG. 9). The half-life of rfmAb-1(mIgG2a), 17P04A(mIgG2a), and 18P01A (mIgG2a) in brain was 28.2, 92.4, and 77.2 h, respectively (FIG. 10). Brain penetration, which is calculated as the ratio of AUC (area under the curve) in brain to AUC in serum, was 1.9% for rfmAb-1(mIgG2a), 5.5% for 17P04A (mIgG2a), and 0.3% for 18P01A(mIgG2a) (FIG. 10). Comparably, 17P04A(mIgG2a) has longer half-life in serum and brain, and better brain penetration, than 18P01A(mIgG2a) or rfmAb-1(mIgG2a). Despite long half-life in serum and brain, 18P01A(mIgG2a) demonstrated lower brain penetration, which should be considered for the potential to limit its efficacy to clear Aβ in the brains of AD patients and in an AD mouse model.

Example 7: Long-Term Efficacy Study of 17P04A in 5xFAD Mice

5xFAD transgenic mice overexpress both mutant human amyloid beta precursor protein (APP) with the Swedish (K670N, M67IL), Florida (1716V), and London (V717I) Familial Alzheimer's Disease (FAD) mutations and human presenilin 1 (PSEN1) with two FAD mutations, M146L and L286V. These mice develop many AD-related phenotypes at a relatively early age. Here we used 5xFAD mice as an AD mouse model to evaluate and compare the long-term efficacy of an antibody having the 17P04A variable region (17P04A Fab) with high selectively for Aβ oligomer/protofibril (see above), and rfmAb-1. 5xFAD mice in B6SJLF1/J background (The Jackson Laboratory, JAX #034840; jax.org; RRID:MMRRC_034840-JAX) at 7 months of age were injected ip weekly with 1, 3, and 10 mg/kg of 17P04A (mIgG2a) or 1, 3, and 10 mg/kg of rfmAb-1(mIgG2a) for 16 weeks. 5xFAD mice injected ip weekly with 1xPBS (vehicle) and naïve B6SJLF1/J mice (wild-type) at the same age were used as the control. There are 10-15 mice in each treatment group.

Measurement of $A\beta_{1-42}$ Levels, $A\beta_{1-40}$ Levels, and Aβ Oligomer/Protofibril Levels in Fractions of Brain Homogenates At three (3) days following the last injection, mice were anesthetized with 250 mg/kg Tribromoethanol and transcardially perfused with ~15 mL 1xPBS (pH 7.4). A half cerebellum of each of the PBS-perfused mice was homogenized in 600 μL of 1xTris-Buffered Saline (TBS) (pH 7.4) with protease and phosphatase inhibitor cocktail (Thermo Scientific, 78444) using a BULLET BLENDER® (Next Advance, BB5E-AU). 250 μL of the homogenate was centrifuged at 20,000×g for 20 min at 4° C. The supernatant is the TBS-soluble fraction. 250 μL of the remaining homogenate was added with equal volume of RIPA (radioimmunoprecipitation assay) buffer (Thermo Scientific, 89901) and centrifuged at 20,000×g for 20 min at 4° C. The supernatant is the RIPA-soluble fraction. The pellet was resuspended in 100 μL of 8 M guanidine-HCl and incubated at room temperature for 2 hours. The resuspension was diluted by adding 400 μL of 1xTBS and centrifuged again at 20,000×g for 20 min at 4°C. The supernatant is the guanidine soluble fraction.

Figure 11A:
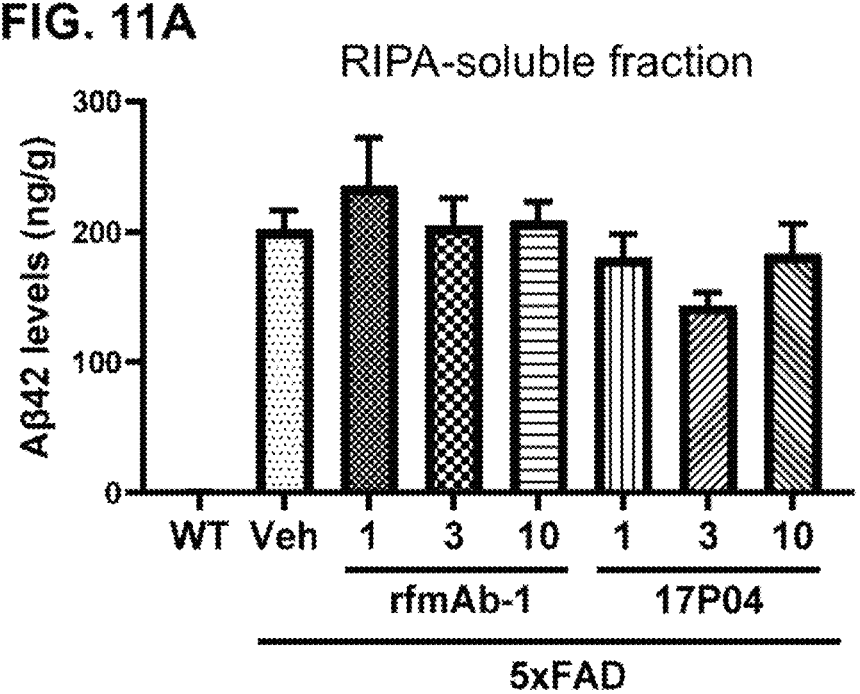
FIGS. 11A-11B show Aβ1-42 levels in the RIPA soluble fraction (FIG. 11A) and guanidine soluble fraction (FIG. 11B) of brain homogenate from naïve (untreated) 11-month-old B6SJLF1/J (WT) mice, 11-month-old 5×FAD mice treated by weekly ip injection of PBS vehicle (Veh), 11-month-old 5×FAD mice treated with rfmAb-1 by weekly ip injection of rfmAb-1 at 1, 3, or 10 mg/kg for 16 weeks, and 11-month-old 5×FAD mice treated with 17P04A by weekly ip injection of 17P04A at 1, 3, or 10 mg/kg for 16 weeks. N=13, 14, 8, 8, 10, 8, 9, 9.
Figure 11B:
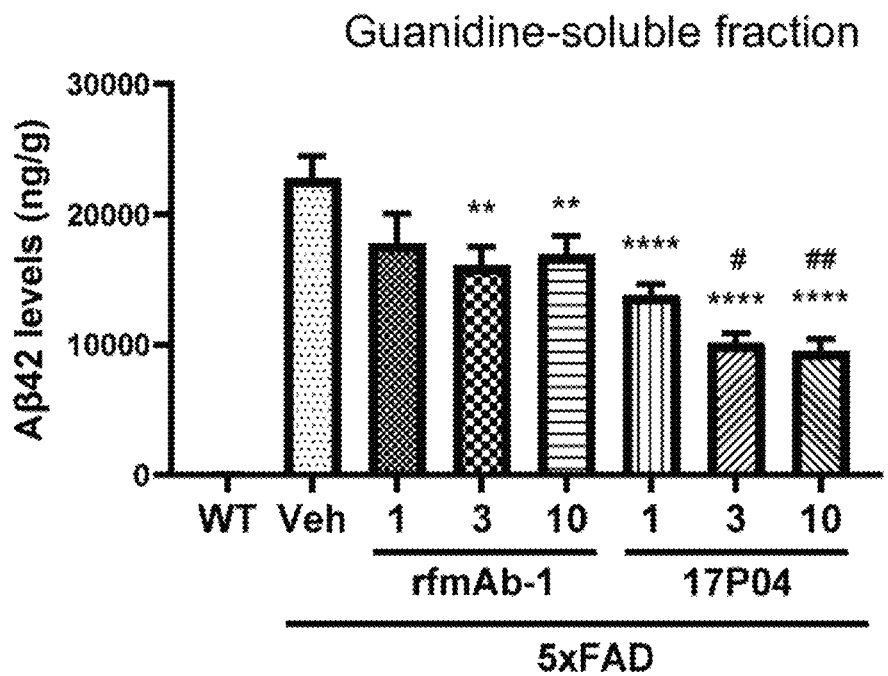

$A\beta_{1-42}$ levels in the RIPA-soluble fraction and guanidine-soluble fraction were measured using Human Amyloid β (aa1-42) QUANTIKINE® ELISA kit (R&D Systems, DAB142; mndsystems.com) following the manufacturer's instructions. Results are shown in FIGS. 11A and 11B. As shown in FIG. 11A, $A\beta_{1-42}$ levels in the RIPA soluble fraction (mostly Aβ monomers) were not affected by 17P04A(mIgG2a) or rfmAb-1 at any doses. FIG. 11B shows that $A\beta_{1-42}$ levels in the guanidine-soluble soluble fraction, a fraction that contains mostly insoluble Aβ fibrils and plaque, were significantly reduced with 17P04A(mIgG2a) injection at 1, 3, and 10 mg/kg and with mAb 158 injection at 3 and 10 mg/kg. Importantly, FIG. 11B shows that $A\beta_{1-42}$ levels in mice treated with 17P04(mIgG2a) were significantly lower than levels in mice treated with rfmAb-1 at the same doses (p<0.05 rfmAb-1 at 3 mg/kg vs 17P04A (mIgG2a) at 3 mg/kg; p<0.01 rfmAb-1 at 10 mg/kg vs 17P04A(mIgG2a) at 10 mg/kg), suggesting that 17P04A (mIgG2a) removes Aβ plaque more effectively than the reference antibody rfmAb-1.

Figure 12A:
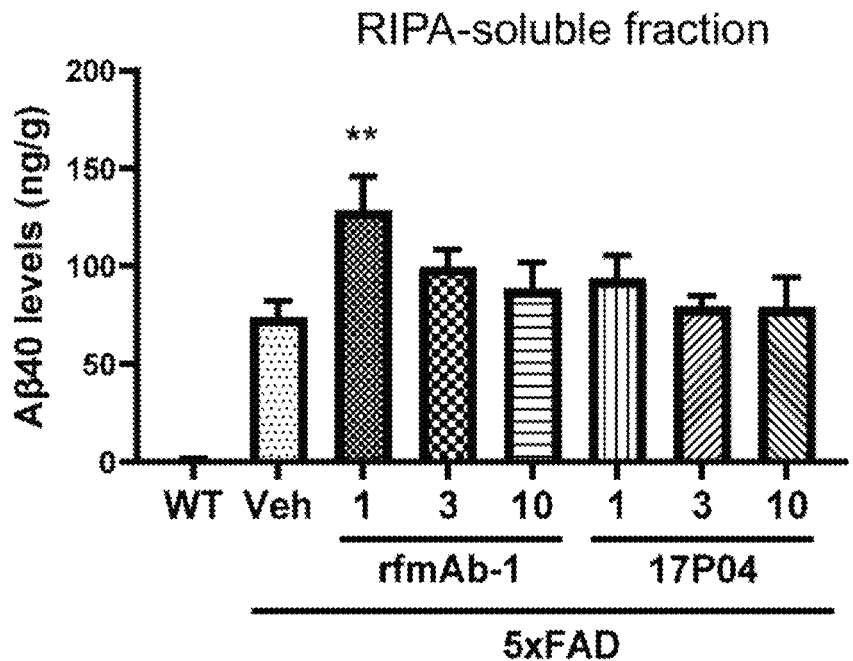
FIGS. 12A-12B show Aβ1-40 levels in the RIPA soluble fraction (FIG. 12A) and guanidine soluble fraction (FIG. 12B) of brain homogenate from naïve (untreated) 11-month-old B6SJLF1/J (WT) mice, 11-month-old 5×FAD mice treated by weekly ip injection of PBS vehicle (Veh), 11-month-old 5×FAD mice treated with rfmAb-1 by weekly ip injection of rfmAb-1 at 1, 3, or 10 mg/kg for 16 weeks, and 11-month-old 5×FAD mice treated with 17P04 by weekly ip injection of 17P04A at 1, 3, or 10 mg/kg for 16 weeks. N=13, 14, 8, 8, 10, 8, 9, 9.
Figure 12B:
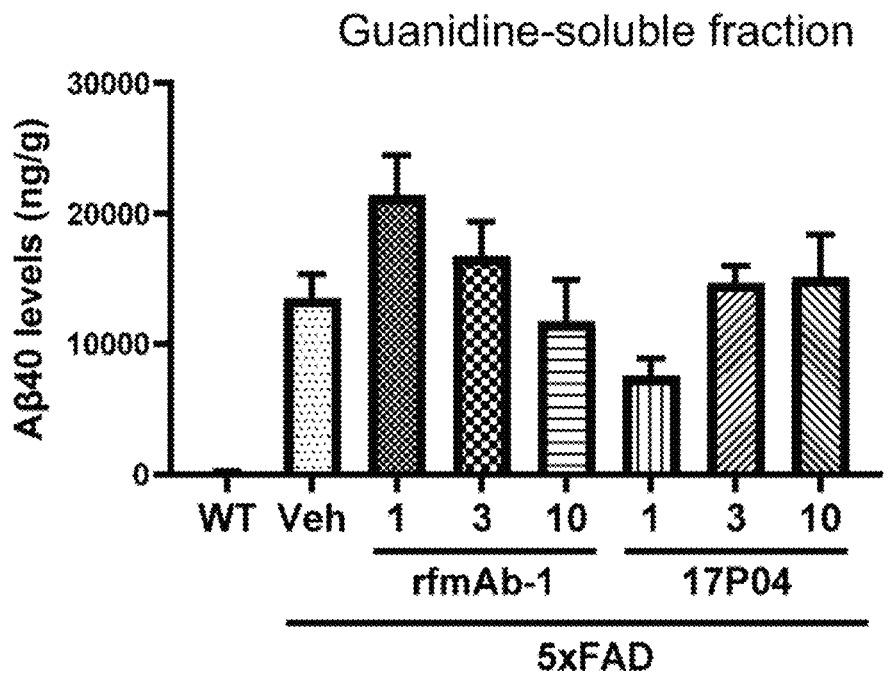

$A\beta_{1-40}$ is the abundant Aβ isoform in the brain. It is considered non-toxic as it is not prone to aggregate. The $A\beta_{1-40}$ levels in the RIPA-soluble fraction and Guanidine-soluble fraction were measured using Human Amyloid β (aa1-40) QUANTIKINE® ELISA kit (R&D systems, DAB140; mndsystems.com) following the manufacturer's instruction. Results are shown in FIGS. 12A and 12B. $A\beta_{1-40}$ levels in both the RIPA-soluble fraction (FIG. 12A) and guanidine-soluble fraction (FIG. 12B) of each sample were not affected by weekly ip injection with 17P04(mIgG2a) at 1, 3, or 10 mg/kg, or rfmAb-1 at 3 or 10 mg/kg. Treatment with rfmAb-1 at 1 mg/kg significantly increased $A\beta_{1-40}$ levels in RIPA-soluble fraction for an unknown reason.

Figure 13:
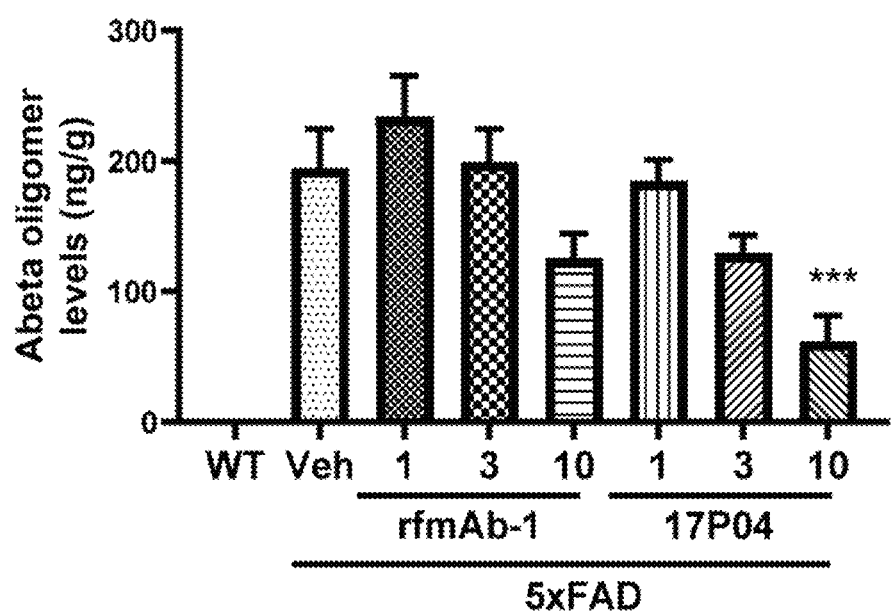
FIG. 13 shows Aβ oligomer/protofibril levels in TBS-soluble fraction of brain homogenate from naïve (untreated) 11-month-old B6SJLF1/J (WT) mice, 11-month-old 5×FAD mice treated by weekly ip injection of PBS vehicle (Veh), 11-month-old 5×FAD mice treated with rfmAb-1 by weekly ip injection of rfmAb-1 at 1, 3, or 10 mg/kg for 16 weeks, and 11-month-old 5×FAD mice treated with 17P04A by weekly ip injection of 17P04 at 1, 3, or 10 mg/kg for 16 weeks. Aβ oligomer levels were measured using a sandwich ELISA, where the capture Ab for the sandwich ELISA was rfmAb-1 and the detection Ab is biotin-18P01A. N=13, 14, 8, 8, 10, 8, 9, and 9. Results of one-way ANOVA followed by Sidak's test: *** $p<0.001$ for 17P04 at 10 mg/kg vs vehicle (Veh).

Aβ oligomer/protofibril levels in the TBS-soluble fraction of brain were measured using a sandwich ELISA with rfmAb-1 as the capture antibody and biotin-labeled 18P01 as the detection antibody. Results are shown in FIG. 13. For the assay, 96-well plates were coated at 4° C. overnight with 100

μL per well of 2 μg/mL rfmAb-1 in PBS. Plates were blocked with 1% BSA in PBS at RT for 1 h. 100 μL per well of TBS-soluble fractions (diluted 1/40) or purified $A\beta_{1-42}$ oligomers (2-fold serial dilutions with concentration in the range of 0-2000 pg/mL) was then added to plates. The plates were incubated for 1 h at RT and washed 3 times. The plates were incubated with 100 μL per well of 1 μg/mL biotinylated 18P01 in 1% BSA for 1 h at RT and washed 3 times. The plates were then incubated with 100 μL per well of HRP-conjugated streptavidin (Molecular Probes, SNN2004) diluted 1:5000 in 1% BSA for 1 h at RT and washed 3 times. TMB Stabilized Chromogen substrate solution was added to the plate, and the reaction was stopped by adding 1M sulfuric acid. The absorbance at 450 nm was measured in a plate reader. The Aβ oligomer levels in the WT mice were considered as the background signal, and the value was deducted from all groups. The result showed that treatment with 17P04 reduced Aβ oligomer in the brain in a dose dependent manner (5%, 34%, and 68% reduction at 1, 3, and 10 mg/kg, respectively) (FIG. 13). The Aβ oligomer/protofibril level with 17P04A(mIgG2a) treatment at 10 mg/kg was significantly lower than that with vehicle treatment (Veh), i.e., control. rfmAb-1 treatment at 10 mg/kg reduced Aβ oligomer by 36% as compared with vehicle treatment group (control) but there was no significant difference. This result demonstrates that 17P04A(mIgG2a) removes Aβ oligomer/protofibril in the brain. This result suggests that 17P04A(mIgG2a) removes Aβ oligomer/protofibril in the brain more effectively than rfmAb-1.

Figure 14A:
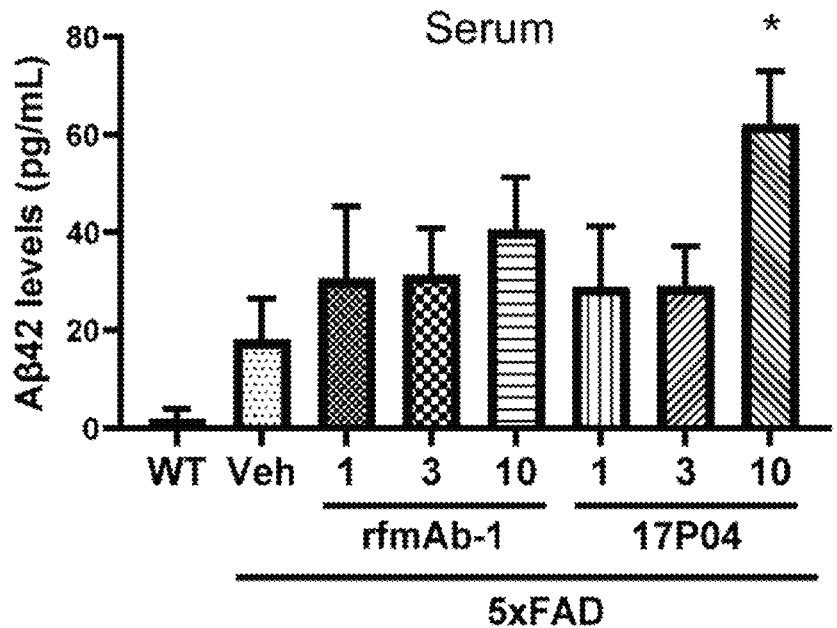
FIGS. 14A-14B show levels of Aβ$_{1-42}$ (FIG. 14A) and Aβ$_{1-40}$ in the serum (FIG. 14B) of naïve (untreated) 11-month-old B6SJLF1/J (WT) mice, 11-month-old 5×FAD mice treated by weekly ip injection of PBS vehicle (Veh), 11-month-old 5×FAD mice treated with rfmAb-1 by weekly ip injection of rfmAb-1 at 1, 3, or 10 mg/kg for 16 weeks, and 11-month-old 5×FAD mice treated with 17P04A by weekly ip injection of 17P04 at 1, 3, or 10 mg/kg for 16 weeks.
Figure 14B:
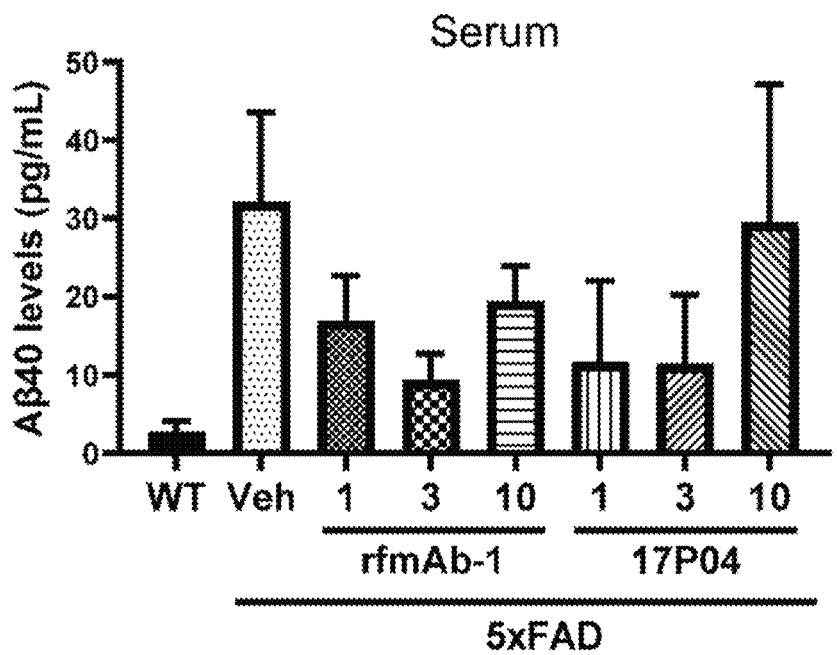

$A\beta_{1-40}$ and $A\beta_{1-42}$ exists in serum mostly as monomers. $A\beta_{1-42}$ levels in the serum of treated mice were measured using LEGEND MAX™ Human Amyloid Beta (1-42) ELISA Kit (BioLegend, 448707) following the kit instruction (FIG. 14). $A\beta_{1-42}$ levels were not changed in the serum of mice treated with 17P04A(mIgG2a) at 1 or 3 mg/kg or rfmAb-1 at 1, 3 or 10 mg/kg. $A\beta_{1-42}$ levels were significantly increased in the serum of mice treated with 10 mg/kg 17P04A(mIgG2a) for an unknown reason. $A\beta_{1-40}$ levels in the serum of treated mice were measured using LEGEND MAX™ Human Amyloid Beta (1-40) ELISA Kit (BioLegend, 449007) (FIG. 14). $A\beta_{1-40}$ levels in the serum were not affected by rfmAb01 or 17P04A(mIgG2a) treatment at any doses.

Measurement of Plaque in Fixed Brain Tissue

The other half of the cerebrum from each PBS-perfused mouse was fixed in 4% PFA in PBS for 1 day and incubated in 1×PBS for 1 day before sending to NeuroScience Associates (neuroscienceassociates.com) for Campbell-Switzer Alzheimer Stain to reveal Aβ plaques. Twenty-five (25) brain hemispheres were embedded together into a single block, and freeze-sectioned at 35 μm in the coronal plane through the cortical section of the mouse brain hemisphere. Campbell-Switzer staining was performed through the cerebrum on every 6th section spaced at 210 μm intervals. Slides (25 brain sections on each slide) were washed in $dH_2O$ three times, placed in 2% $NH_4OH$ for 5 min, and washed in $dH_2O$ one more time. Slides were then placed in silver-pyridine-carbonate solution (Neuroscience Associates) for 40 min, and washed in 1% citric acid for 3 min. Slides were placed in 4.99 pH acetate buffer working solution (Neuroscience Associates) and then developed in fresh physical developer ABS solution (Neuroscience Associates). The developing time is consistent among slides. The development was stopped by placing slides in 4.99 pH acetate buffer working solution briefly. The slides were washed in $dH_2O$ for 30 seconds and placed into 0.5% sodium thiosulfate solution for 45 seconds. After final washes in $dH_2O$ (3×2 min), the slides were covered by coverslip. Next, the slides were imaged under a bright-field microscope. Representative images of Campbell-Switzer stain are shown in FIG. 15. The percentage area of condensed and diffused plaque in each brain section was quantified using the ImageJ software for image processing and analysis (imagej.net). The cortical and hippocampal area in each brain section was outlined and the total area was measured. To measure the condensed plaque, the threshold of the image was adjusted to 0, 20. To measure the condensed plus diffuse plaque, the threshold of the image was adjusted to 0, 50. Plaque area was measured using the Analyze Particle function in ImageJ. The size of the particle was set at 10 to infinity. Percentage area was calculated as plaque area divided by total area. The percentage area of 4 brain sections at bregma −0.25, −1.30, −2.35, and −3.40 mm in each brain was measured and averaged. 8 to 13 brains for each treatment group were analyzed. The results in FIG. 15 showed that treatment of 5×FAD mice with 17P04A(mIgG2a) at 3 and 10 mg/kg significantly reduced condensed plaque and diffuse plaque in the brain of 5×FAD mice. rfmAb-1 treatment at any dose had no significant effect on levels of condensed or diffuse plaque.

The results of the long-term efficacy study showed that treatment with 17P04A(mIgG2a) results in a statistically significant reduction in soluble Aβ oligomer/protofibril in brains of 5×FAD mice, compared with the level in control 5×FAD mice treated with vehicle (PBS) for the same amount of time (FIG. 13). This suggests that 17P04A(mIgG2a) effectively removes soluble Aβ oligomer/protofibril in brains in an in vivo AD disease model.

The results of the long-term efficacy study showed that treatment with 17P04A(mIgG2a) results in a statistically significant reduction in the amount of condensed plaque and insoluble plaque in the brains of 5×FAD mice, compared with the amounts in control 5×FAD mice treated with vehicle (PBS) for the same amount of time (FIG. 15). These results showed that 17P04A(mIgG2a) removed condensed and diffuse plaque more efficiently than the reference antibody rfmAb-1 in the brain of 5×FAD mice. This suggests that 17P04A(mIgG2a) effectively removes both condensed and insoluble Aβ fibril/plaque in brains in an in vivo AD disease model. These results show that treatment with 17P04A(mIgG2a) can effectively remove and/or reduce Aβ plaque in the brain, and thereby reduce the plaque burden, in animals suffering from at least one condition associated with Aβ protein aggregation, particular AD.

What is claimed is:

1. An anti-amyloid β (Aβ) protofibril/oligomer antibody that preferentially binds soluble Aβ protofibril/oligomer, wherein a complex comprising the anti-Aβ protofibril/oligomer antibody bound to Aβ protofibril/oligomer can trigger antibody-dependent cell-mediated phagocytosis (ADCP) by a microglial cell after exposure of the microglial cell to the complex, wherein the anti-Aβ protofibril/oligomer antibody has a fully human variable region and is selected from one of (a) an antibody comprising a fully human heavy chain variable region (VH) comprising an heavy chain (HC) complementarity determining region (CDR)1 having the amino acid sequence GFTLSSFS (SEQ ID NO: 42), an HC CDR2 having the amino acid sequence ISSRRTYI (SEQ ID NO: 43), and an HC CDR3 having the amino acid sequence ARGGYIGSPNAYDI (SEQ ID NO: 44), and a fully human light chain variable region (VL) comprising a light chain (LC) CDR1 having the amino acid sequence TGAVTSDYY (SEQ ID NO: 47), an LC CDR2 having the amino acid sequence SAS, and an LC CDR3 having the amino acid sequence LLYYGGAWV (SEQ ID NO: 49), (b) an antibody comprising a fully human VH comprising an HC CDR 1 having the amino acid sequence GFTFSGSA (SEQ ID NO: 62), an HC CDR2 having the amino acid sequence IRSKANSYAT (SEQ ID NO: 63), and an HC CDR3 having the amino acid sequence TSHAPNFDAFDI (SEQ ID NO: 64), and a fully human VL comprising an LC CDR1 having the amino acid sequence SSNIGNHY (SEQ ID NO: 67), an LC CDR2 having the amino acid sequence DNS, and an LC CDR3 having the amino acid sequence GTWDSSLSTYV (SEQ ID NO: 69), (c) an antibody comprising a fully human VH comprising an HC CDR 1 having the amino acid sequence GFTFSGSA (SEQ ID NO: 72), an HC CDR2 having the amino acid sequence IRSKVNSYAT (SEQ ID NO: 73), and an HC CDR3 having the amino acid sequence TSHAPIFDAFDI (SEQ ID NO: 74), and a fully human VL comprising an LC CDR1 having the amino acid sequence SSNIGNHY (SEQ ID NO: 77), an LC CDR2 having the amino acid sequence DNS, and an LC CDR3 having the amino acid sequence GTWDSSLSTYF (SEQ ID NO: 79), (d) an antibody comprising a fully human VH comprising an HC CDR 1 having the amino acid sequence GFTFSNAW (SEQ ID NO: 132), an HC CDR2 having the amino acid sequence IKSKTDGGTR (SEQ ID NO: 133), and an HC CDR3 having the amino acid sequence TTGYGEGY (SEQ ID NO: 134), and a fully human VL comprising an LC CDR1 having the amino acid sequence SSNIKSNT (SEQ ID NO: 137), an LC CDR2 having the amino acid sequence RNN, and an LC CDR3 having the amino acid sequence AAWDDSLKGVV (SEQ ID NO: 139), and (e) an antibody comprising a fully human VH comprising an HC CDR 1 having the amino acid sequence GFSFSNAW (SEQ ID NO: 2), an HC CDR2 having the amino acid sequence IKSKTDGGTI (SEQ ID NO: 3), and an HC CDR3 having the amino acid sequence TTGYGEGY (SEQ ID NO: 4), and a fully human VL comprising an LC CDR1 having the amino acid sequence SSNIKSNT (SEQ ID NO: 7), an LC CDR2 having the amino acid sequence RNN, and an LC CDR3 having the amino acid sequence AAWDDSLKGVV (SEQ ID NO: 9).

2. The anti-Aβ protofibril/oligomer antibody of claim 1, wherein the anti-Aβ protofibril/oligomer antibody can penetrate brain tissue of a mammalian subject after administration to the mammalian subject.

3. The anti-Aβ protofibril/oligomer antibody of claim 2, wherein the anti-Aβ protofibril/oligomer antibody can reduce levels of soluble Aβ oligomer/protofibril in the brain of the mammalian subject after administration.

4. The anti-Aβ protofibril/oligomer antibody of claim 2, wherein the anti-Aβ protofibril/oligomer antibody can reduce levels of Aβ plaque in the brain of the mammalian subject after administration.

5. The anti-Aβ protofibril/oligomer antibody of claim 1 wherein constant region sequence involved in triggering ADCP comprises sequence from an IgG fragment crystallizable region (Fc), optionally selected from mouse IgG1 Fc, human IgG1 Fc, and mouse IgG2a Fc.

6. A pharmaceutical composition comprising the anti-Aβ protofibril/oligomer antibody of claim 1 and a pharmaceutically acceptable carrier or excipient.

7. A method of reducing the amount of soluble Aβ protofibril/oligomer in a subject, comprising administering to the subject a therapeutically effective amount of the anti-Aβ protofibril/oligomer antibody of claim 1.

8. The method of claim 7, wherein administering the anti-Aβ protofibril/oligomer antibody reduces the amount of soluble Aβ protofibril/oligomer in brain tissue of the subject.

9. A method of reducing the amount of Aβ plaque in a subject, comprising administering to said subject a therapeutically effective amount of the anti-Aβ protofibril/oligomer antibody of claim 1.

10. A method of preventing or slowing the development of at least one condition associated with Aβ protein aggregation comprising administering an effective amount of the anti-Aβ protofibril/oligomer antibody of claim 1 to a subject in need thereof.

11. The method of claim 10, wherein the condition associated with Aβ protein aggregation is Alzheimer's disease (AD).

12. The anti-Aβ oligomer antibody of claim 1, wherein the anti-Aβ oligomer antibody is one of
- an antibody comprising a fully human heavy chain variable region (VH) having the amino acid sequence of SEQ ID NO: 41 and a fully human light chain variable region (VL) having the amino acid sequence of SEQ ID NO: 46,
- an antibody comprising a fully human VH having the amino acid sequence of SEQ ID NO: 61, and a fully human VL having the amino acid sequence of SEQ ID NO: 66,
- an antibody comprising a fully human VH having the amino acid sequence of SEQ ID NO: 71 and a fully human VL having the amino acid sequence of SEQ ID NO: 76,
- an antibody comprising a fully human VH having the amino acid sequence of SEQ ID NO: 131 and a fully human VL having the amino acid sequence of SEQ ID NO: 136, and
- an antibody comprising a fully human VH having the amino acid sequence of SEQ ID NO: 1 and a fully human VL having the amino acid sequence of SEQ ID NO: 6.

* * * * *